(12) United States Patent
Hyde et al.

(10) Patent No.: US 8,058,872 B2
(45) Date of Patent: Nov. 15, 2011

(54) SYSTEMS, DEVICES, METHODS, AND COMPOSITIONS INCLUDING FUNCTIONALIZED FERROMAGNETIC STRUCTURES

(75) Inventors: Roderick A. Hyde, Redmond, WA (US); Jordin T. Kare, Seattle, WA (US); Wayne R. Kindsvogel, Seattle, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 279 days.

(21) Appl. No.: 12/455,298

(22) Filed: May 29, 2009

(65) Prior Publication Data

US 2010/0301856 A1 Dec. 2, 2010

(51) Int. Cl.
*G01V 3/00* (2006.01)
(52) U.S. Cl. .......................... 324/307; 324/309; 324/318
(58) Field of Classification Search .......... 324/300–322; 600/410–435
See application file for complete search history.

(56) References Cited

U.S. PATENT DOCUMENTS

| | | | |
|---|---|---|---|
| 4,184,110 A * | 1/1980 | Hinshaw ....................... 324/300 |
| 5,175,499 A | 12/1992 | Davies |
| 5,506,053 A | 4/1996 | Hubbard |
| 5,532,667 A | 7/1996 | Haertling et al. |
| 5,801,221 A | 9/1998 | Tanaka et al. |
| 5,804,563 A | 9/1998 | Still et al. |
| 5,831,012 A | 11/1998 | Nilsson et al. |
| 6,255,461 B1 | 7/2001 | Mosbach et al. |
| 6,275,722 B1 | 8/2001 | Martin et al. |
| 6,660,176 B2 | 12/2003 | Tepper et al. |
| 6,670,427 B1 | 12/2003 | Ulbricht et al. |
| 6,797,522 B1 | 9/2004 | Still et al. |
| 6,873,153 B2 | 3/2005 | Frydman |
| 6,879,160 B2 | 4/2005 | Jakab |
| 6,977,503 B2 | 12/2005 | Prado |
| 7,075,302 B2 | 7/2006 | Zhu |
| 7,095,230 B2 | 8/2006 | Blümich et al. |
| 7,096,057 B2 | 8/2006 | Hockett et al. |
| 7,236,142 B2 | 6/2007 | Amyotte et al. |
| 7,236,821 B2 | 6/2007 | Cates et al. |
| 7,258,734 B2 | 8/2007 | Lin et al. |
| 7,271,589 B2 | 9/2007 | Melzi et al. |
| 7,276,904 B2 | 10/2007 | Busse et al. |
| 7,288,415 B2 | 10/2007 | Huang |
| 7,309,986 B2 | 12/2007 | Epstein et al. |
| 7,319,038 B2 | 1/2008 | Southard |
| 7,319,326 B2 | 1/2008 | Balcom et al. |
| 7,358,734 B2 | 4/2008 | Blümich et al. |
| 7,371,977 B1 | 5/2008 | Preonas |
| 7,418,289 B2 | 8/2008 | Hyde et al. |
| 7,442,754 B2 | 10/2008 | Tepper et al. |

(Continued)

FOREIGN PATENT DOCUMENTS

WO    WO 2005/101045 A1    10/2005

(Continued)

OTHER PUBLICATIONS

"A Guide to Silane Solutions"; Dow Corning; 30 pages.

(Continued)

*Primary Examiner* — Dixomara Vargas

(57) ABSTRACT

Magnetic resonance systems, devices, methods, and compositions are provided. A nuclear magnetic resonance imaging composition includes, but is not limited to, a plurality of functionalized ferromagnetic microstructures configured to generate a time-invariant magnetic field within at least a portion of one or more internal surface-defined voids.

20 Claims, 42 Drawing Sheets

U.S. PATENT DOCUMENTS

| | | | |
|---|---|---|---|
| 7,483,732 | B2 | 1/2009 | Zhong et al. |
| 7,495,439 | B2 | 2/2009 | Wiggins |
| 2002/0061599 | A1* | 5/2002 | Elling et al. ............... 436/518 |
| 2004/0018508 | A1 | 1/2004 | Friedman |
| 2005/0171434 | A1 | 8/2005 | Madden et al. |
| 2006/0204442 | A1 | 9/2006 | Tapolsky et al. |
| 2007/0020701 | A1 | 1/2007 | Menon et al. |
| 2007/0078376 | A1 | 4/2007 | Smith |
| 2007/0194788 | A1 | 8/2007 | Pines et al. |
| 2007/0200085 | A1 | 8/2007 | Matsui et al. |
| 2008/0024130 | A1* | 1/2008 | Schlueter et al. ............ 324/309 |
| 2008/0206146 | A1 | 8/2008 | Akhtari et al. |
| 2008/0206152 | A1 | 8/2008 | Hoffmann et al. |
| 2008/0213181 | A1 | 9/2008 | Harris |
| 2008/0279765 | A1 | 11/2008 | Chettibi et al. |
| 2008/0306377 | A1 | 12/2008 | Piron et al. |
| 2009/0015256 | A1 | 1/2009 | Bottomley et al. |
| 2009/0029392 | A1 | 1/2009 | Josephson et al. |

FOREIGN PATENT DOCUMENTS

| | | |
|---|---|---|
| WO | WO 2006/040725 A1 | 4/2006 |
| WO | WO 2007/075891 A3 | 7/2007 |
| WO | WO 2007/111382 A1 | 10/2007 |
| WO | WO 2009/027973 A1 | 3/2009 |
| WO | WO 2009/029880 A2 | 3/2009 |
| WO | WO 2009/029896 A1 | 3/2009 |

OTHER PUBLICATIONS

Allen et al.; "Ligand-Mediated Targeting: An Update"; Proceedings of the 2004 International Conference on MEMS, NANO and Smart Systems; 2004; 2 pages; IEEE.

Bartlett et al.; "Impact of Tumor-Specific Targeting on the Biodistribution and Efficacy of siRNA Nanoparticles Measured by Multimodality in Vivo Imaging"; PNAS, Pharmacology; bearing a date of Sep. 25, 2007; pp. 15549-15554; vol. 104, No. 39; PNAS.

Baskin et al.; "Copper-Free Click Chemistry for Dynamic in Vivo Imaging"; PNAS: Cell Biology, Chemistry; bearing a date of Oct. 23, 2007; pp. 16793-16797; vol. 104, No. 43; PNAS; located at: www.pnas.org/cgi/doi/10.1073/pnas.0707090104.

Bird et al.; "Single-Chain Antigen-Binding Proteins"; Science, Reports; bearing a date of Oct. 21, 1988; pp. 423-426; vol. 242.

Blancafort et al.; "Rational Design, Selection and Specificity of Artificial Transcription Factors (ATFs): The Influence of Chromatin in Target Gene Regulation"; Combinatorial Chemistry & High Throughput Screening; 2008; pp. 146-158; vol. 11; Bentham Science Publishers Ltd.

Bonetto et al.; "Identification of Cyclic Peptides able to Mimic the Functional Epitope of IgG1-Fc for Human FcγRI"; The FASEB Journal, Research Communication; bearing a date of Feb. 2009; pp. 575-585; vol. 23.

Bowtell et al.; "News and Views: A Colorful Future for MRI"; Nature: Medical Imaging; bearing a date of Jun. 2008; pp. 993-994; vol. 453, No. 19.

Brunner et al.; "Travelling-wave Nuclear Magnetic Resonance"; Nature: Letters; bearing a date of Feb. 19, 2009; pp. 994-999; vol. 457; Macmillan Publishers Limited.

Cao et al.; "Molecular Beacon Aptamers for Protein Monitoring in Real-Time and in Homogeneous Solutions"; Current Proteomics; 2005; pp. 31-40; vol. 2.

Caruso et al.; "Nanoengineering of Inorganic and Hybrid Hollow Spheres by Colloidal Templating"; Science; bearing a date of Nov. 6, 1998; pp. 1111-1114; vol. 282; located at: www.science.org.

Chen et al.; "Aptamer from Whole-Bacterium SELEX as new Therapeutic Reagent Against Virulent Mycobacterium Tuberculosis"; Science Direct. Biochemical and Biophysical Research Communications; 2007; pp. 743-748; vol. 357.

Chopra et al.; "Monoclonal Antibody Against Antigen A7 Coupled to Ferromagnetic Lignosite Particles"; Molecular Imaging & Contrast Agent Database; pp. 1-4.

Crawford et al.; "Technique Review: Peptide Aptamers: Tools for Biology and Drug Discovery"; Briefings in Functional Genomics and Proteomics; bearing a date of Apr. 2003; pp. 72-79; vol. 2, No. 1; Henry Stewart Publications.

Degen et al.; "Nanoscale Magnetic Resonance Imaging"; PNAS Early Edition; bearing a date of 2009; pp. 1-5; located at: www.pnas.org/cgi/doi/10.1073/pnas.0812068106.

Epstein et al.; "Magnetic Resonance Imaging in Inhomogeneous Fields"; Inverse Problems; bearing a date of 2004; pp. 753-780; vol. 20; IOP Publishing.

Farokhzad et al.; "Drug Delivery Systems in Urology—Getting 'Smarter'"; NIH Public Access: Author Manuscript; Urology; bearing a date of Sep. 2006; pp. 1-13; vol. 68, No. 3.

Fougere et al.; "New Non-External Field Inductive Conductivity Sensor (NXIC) for Long Term Deployments in Biologically Active Regions"; bearing a date of 2000; pp. 623-630; IEEE.

Godeau et al.; "Letter: Lipid-Conjugated Oligonucleotides via 'Click Chemistry' Efficiently Inhibit Hepatitis C Virus Translation"; Journal of Medicinal Chemistry; 2008; pp. 4374-4376; vol. 51, No. 15; American Chemical Society.

Harmsen et al.; "Mini-Review: Properties, Production, and Applications of Camelid Single-Domain Antibody Fragments"; Appl. Microbiology Biotechnology; 2007; pp. 13-22; vol. 77; Springer.

Harris et al.; "NMR Nomenclature, Nuclear Spin Properties and Conventions for Chemical Shifts"; International Union of Pure and Applied Chemistry; bearing a date of 2001; pp. 1795-1818; vol. 73, No. 11; IUPAC.

Hein et al.; "Expert Review: Click Chemistry, A Powerful Tool for Pharmaceutical Sciences"; Pharmaceutical Research; bearing a date of Oct. 2008; pp. 2216-2230; vol. 25, No. 10; Springer Science and Business Media, LLC.

Heverhagen et al.; "Science to Practice: Smart Near-Infrared Imaging Probes—A Quantum Leap for Early Detection of Colorectal Cancer?"; Science to Practice: Radiology; bearing a date of Jul. 2007; pp. 1-2; vol. 244, No. 1.

Holliger et al.; "'Diabodies': Small Bivalent and Bispecific Antibody Fragments"; Proc. Natl. Acad. Sci.; bearing a date of Jul. 1993; pp. 6444-6448; vol. 90.

Huston et al.; Protein Engineering of Antibody Binding Sites: Recovery of Specific Activity in an Anti-Digoxin Single-Chain Fv Analogue Produced in *Escherichia Coli*; Proc. Natl. Acad. Sci.; bearing a date of Aug. 1988; pp. 5879-5883; vol. 85.

Ishikawa et al.; "Amyloid Imaging Probes are Useful for Detection of Prion Plaques and Treatment of Transmissible Spongiform Encephalopathies"; Journal of General Virology; 2004; pp. 1785-1790; vol. 85.

Jaiswal et al.; "Research Article: Long-Term Multiple Color Imaging of Live Cells Using Quantum Dot Bioconjugates"; Nature Biotechnology; bearing a date of Jan. 2003; pp. 47-51; vol. 21.

Jayasena; "Aptamers: An Emerging Class of Molecules That Rival Antibodies in Diagnostics"; Clinical Chemistry; 1999; pp. 1628-1650; vol. 45, No. 9; American Association for Clinical Chemistry.

Jorge et al.; "Review: Optical Fiber Sensing Using Quantum Dots"; Sensors; 2007; pp. 3489-3534; vol. 7; MDPI.

Josephson et al.; "High-Efficiency Intracellular Magnetic Labeling with Novel Superparamagnetic-Tat Peptide Conjugates"; Bioconjugate Chem.; bearing a date of Feb. 26, 1999; pp. 186-191; vol. 10; American Chemical Society.

Kageyama et al.; "Weak Ferrinmagnetism, Compensation Point, and Magnetization Reversal in $Ni(HCOO)_2 \cdot 2H_2O$"; Physical Review; 2003; pp. 224422-1 to 224422-7; vol. 67; The American Physical Society.

Kamruzzaman et al.; "Surface Modification of Magnetite Nanoparticles Using Lactobionic Acid and Their Interaction with Hepatocytes"; Science Direct, Biomaterials; bearing a date of 2007; pp. 710-716; vol. 28; Elsevier Ltd.; located at: www.elsevier.com/locate/biomaterials.

Kim et al.; "Hepatocyte-Targeted Nuclear Imaging Using $^{99m}$Tc-Galactosylated Chitosan: Conjugation, Targeting, and Biodistribution"; pp. 141-145.

Kipriyanov et al.; "Single-Chain Antibody Streptavidin Fusions: Tetrameric Bifunctional scFv-Complexes with Biotin Binding Activity and Enhanced Affinity to Antigen"; Hum Antibodies Hybridomas; 1995; vol. 6, No. 3; Only the Abstract is being provided.

Kipriyanov et al.; "Recombinant Single-Chain Fv Fragments Carrying C-Terminal Cysteine Residues: Production of Bivalent and Biotinylated Miniantibodies"; Molecular Immunology; 1994; pp. 1047-1058; vol. 31, No. 14; Elsevier Science Ltd.

Knappik et al.; "Fully Synthetic Human Combinatorial Antibody Libraries (HuCAL) Based on Modular Consensus Frameworks and CDRs Randomized with Trinucleotides"; JMB; 2000; pp. 57-86; vol. 296; Academic Press.

Krag et al.; "Research Article: Selection of Tumor-Binding Ligands in Cancer Patients with Phage Display Libraries"; Cancer Research; bearing a date of Aug. 1, 2006; pp. 7724-7733; vol. 66, No. 15.

Kranz et al.; "Conjugates of Folate and Anti-T-Cell-Receptor Antibodies Specifically Target Folate-Receptor-Positive Tumor Cells for Lysis"; Proc. Natl. Acad. Sci.; bearing a date of Sep. 1995; pp. 9057-9061; vol. 92.

Kupper et al.; "Research article: Generation of Human Antibody Fragments Against Streptococcus Mutans Using a Phage Display Chain Shuffling Approach"; BMC Biotechnology; bearing a date of Jan. 25, 2005; pp. 1-12; vol. 5, No. 4; Kupper et al.

Lavanya; "Effects of Electromagnetic Radiation on Biological Systems: A Short Review of Case Studies"; Proceedings of INCEMIC; 2003; pp. 87-90.

Leamy; "Preparation, Characterization, and In Vitro Testing of Poly (Lactide-Co-Glycolide) and Dextran Magnetic Microspheres for In Vivo Applications"; A Dissertation Presented to the Graduate School of the School of the University of Florida in Partial Fulfillment of the Requirements for the Degree of Doctor of Philosophy; University of Florida; 2003; pp. 1-134.

Lee et al.; "Artificially Engineered Magnetic Nanoparticles for Ultra-Sensitive Molecular Imaging"; Nature Medicine; bearing a date of Jan. 2007; pp. 95-99; vol. 13, No. 1; Nature Publishing Group; located at: http://www.nature.com/naturemedicine.

Liu et al.; "Supramolecular Chemistry on Water-Soluble Carbon Nanotubes for Drug Loading and Delivery"; ACS NANO; 2007; pp. 50-56; vol. 1, No. 1; American Chemical Society.

"Magnetic Resonance Imager: What are its Primary Applications? What are the Benefits to Utilities?"; Project Fact Sheet; Superconductivity Partnership with Industry; 1 page.

"Magnetic Resonance Imager: What is the Market Potential? What are the Projects Accomplishments to Date?"; Project Fact Sheet; Superconductivity Partnership with Industry; 1 page.

Matsushita et al.; "Photo-Acceleration of Protein Release from Endosome in the Protein Transduction System"; FEBS Letters; 2004; pp. 221-226; vol. 572; Elsevier B.V.

Michaelis et al.; "Covalent Linkage of Apolipoprotein E to Albumin Nanoparticles Strongly Enhances Drug Transport into the Brain"; The Journal of Pharmacology and Experimental Therapeutics; bearing a date of 2006; pp. 1246-1253; vol. 317, No. 3; The American Society for Pharmacology and Experimental.

Ming et al.; "Azide-Alkyne "Click" Reaction Performed on Oligonucleotides with the Universal Nucleoside 7-Octadiyunyl-7-Deaza-2'-Deoxyinosine"; Nucleic Acids Symposium Series; bearing a date of Sep. 8, 2008; pp. 471-472; No. 52; Oxford University Press.

Moore et al.; "Recent Developments in the Engineering of Zinc Finger Proteins"; Briefings in Functional Genomics and Proteomics; bearing a date of Jan. 2003; pp. 342-355; vol. 1, No. 4; Henry Stewart Publications.

Na et al.; "Imaging Agents: Development of a $T_1$ Contrast Agent for Magnetic Resonance Imaging Using MnO Nanoparticles"; Angewandte Chemie; bearing a date of 2007; pp. 1-6; vol. 46; Wiley-VCH Verlag GmbH & Co.

Nauenburg et al.; "Induction of Apoptosis in Cervical Carcinoma Cells by Peptide Aptamers that Bind to the HPV-16 E7 Oncoprotein[1]"; The FASEB Journal; bearing a date of Mar. 2001; pp. 592-594; vol. 15.

"NMR/Experiments"; 1 page.

Osaka et al.; "Chemical Synthesis of Magnetic Nanoparticles and Their Applications to Recording Media & Biomedical Materials"; 1 page.

Ozaki et al.; "Minireview: Cytokine and Cytokine Receptor Pleiotropy and Redundancy"; The Journal of Biological Chemistry; bearing a date Aug. 16, 2002; pp. 29355-29358; vol. 277, No. 33.

Peng et al.; "Review: Targeted Magnetic Iron Oxide Nanoparticles for Tumor Imaging and Therapy"; International Journal of Nanomedicine; bearing a date of 2008; pp. 311-321; vol. 3, No. 3; Dove Medical Press Ltd.

Peppas et al.; "Review Article: Polymers and Gels as Molecular Recognition Agents"; Pharmaceutical Research; bearing a date of May 2002; pp. 578-587; vol. 19, No. 5.

Poljak; "Production and Structure of Diabodies"; Current Biology; bearing a date of Dec. 15, 1994; pp. 1121-1123; vol. 2; Current Biology Ltd.

Proske et al.; "Mini-Review: Aptamers—Basic Research, Drug Development, and Clinical Applications"; Appl Microbiol Biotechnol; 2005; pp. 367-374; vol. 69.

"Quantum dot-trastuzumab"; Molecular Imaging & Contrast Agent Database; pp. 1-5.

Santra et al.; "TAT Conjugated, FITC Doped Silica Nanoparticles for Bioimaging Applications"; Chem Comm; 2004; pp. 2810-2811; The Royal Society of Chemistry.

Selim et al.; "Surface Modification of Magnetite Nanoparticles Using Lactobionic Acid and Their Interaction with Hepatocytes"; Science Direct-Biomaterials; bearing a date of 2007; pp. 710-716; vol. 28; Elsevier Ltd; located at: www.elsevier.com/locate/biomaterials.

Serda et al.; "Research Article: Targeting and Cellular Trafficking of Magnetic Nanoparticles for Prostate Cancer Imaging"; Molecular Imaging; bearing dates of Jul.-Aug. 2007; pp. 277-288; vol. 6, No. 4; BC Decker Inc.

Shangguan et al.; "Aptamers Evolved from Live Cells as Effective Molecular Probes for Cancer Study"; PNAS; bearing a date of Aug. 8, 2006; pp. 11838-11843; vol. 103, No. 32; PNAS.

Silva et al.; "Hardware Considerations for Functional Magnetic Resonance Imaging"; Concepts in Magnetic Resonance Part A; bearing a date of 2003; pp. 35-49; vol. 16A, No. 1; Wiley Periodicals Inc.

Soroceanu et al.; "Use of Chlorotoxin for Targeting of Primary Brain Tumors"; Cancer Research; bearing a date of Nov. 1, 1998; pp. 4871-4879; vol. 58.

Spear et al.; "Isolation, Characterization, and Recovery of Small Peptide Phage Display Epitopes Selected Against Viable Malignant Glioma Cells"; Cancer Gene Therapy; 2001; pp. 506-511; vol. 8, No. 7.

"Surface Modification and Functionalization of Colloidal Nanoparticles"; Dissertation.

"Terranova-MRI: Earth's Field MRI & NMR Teaching System"; Magritek; 1 page; located at: www.magritek.com.

"The MRI Machine"; 1 page, printed on Mar. 13, 2009; located at: http://people.ee.duke.edu/~jshorey/MRIHomepage/work2.html.

Thrower; "Static and Gradient Field Inhomogeneity Compensation for Low-Cost MRI Machines"; Dissertation: Electrical and Computer Engineering; 2002; pp. 1-100, plus Abstract.

Uil et al.; "Therapeutic Modulation of Endogenous Gene Function by Agents with Designed DNA-Sequence Specificities"; Nucleic Acids Research; bearing a date of 2003; pp. 6064-6078; vol. 31, No. 21; Oxford University Press.

Van Dongen et al.; "Single-Step Azide Introduction in Proteins via an Aqueous Diazo Transfer"; Bioconjugate Chemistry; 2009; pp. 20-23; vol. 20, No. 1.

Verma et al.; "Surface-Structure-Regulated Cell-Membrane Penetration by Monolayer-Protected Nanoparticles"; Nature Materials; 2008; pp. 1-8; Nature Publishing Group.

Wadghiri et al.; "Detection of Alzheimer's Amyloid in Transgenic Mice Using Magnetic Resonance Microimaging"; Magnetic Resonance in Medicine; bearing a date of 2003; pp. 293-302; vol. 50; Wiley-Liss Inc.

Ward et al.; "Binding Activities of a Repertoire of Single Immunoglobulin Variable Domains Secreted from *Escherichia Coli*"; Letter to Nature; bearing a date of Oct. 12, 1989; pp. 544-546; vol. 341; Nature Publishing Group.

Web Site for Images and Structural Information of Lectins: Bettler et al.; "Imberty 3D-Lectin Database"; located at: http://www.cermav.cnrs.fr/lectines/.

Wu et al.; "One-step Synthesis of Magnetic Hollow Silica and Their Application for Nanomedicine"; Journal of Applied Physics; bearing a date of 2006; pp. 08H104-1 through 08H104-3; vol. 99; American Institute of Physics.

Ye et al.; "Review: Molecularly Imprinted Polymers as Antibody and Receptor Mimics for Assays, Sensors and Drug Discovery"; Anal. Bioanal. Chem.; 2004; pp. 1887-1897; vol. 378.

Yezhelyev et al.; "Proton-Sponge-Coated Quantum Dots for siRNA Delivery and Intracellular Imaging"; NIH Public Access; 2009; pp. 1-16.

Yoshihara; "Primary Research: Voxel-Based Structural Magnetic Resonance Imaging (MRI) Study of Patients with Early Onset Schizophrenia"; Annals of General Psychiatry: BioMed Central; 2008; pp. 1-11; vol. 7, No. 25; BioMed Central Ltd.

Yoshikawa et al.; "Communication: Organelle-Targeted Delivery of Biological Macromolecules Using the Protein Transduction Domain: Potential Applications for Peptide Aptamer Delivery into the Nucleus"; Science Direct, JMB; 2008; pp. 777-782; vol. 380; Elsevier Ltd.

Zabow et al.; "Micro-Engineered Local Filed Control for High-Sensitivity Multispectral MRI"; Nature; bearing a date of 2008; pp. 1058-1063 plus additional "Methods" page; MacMillan Publishers Ltd.

Zhang et al.; "Specific Targeting of Tumor Angiogenesis by RGD-Conjugated Ultrasmall Superparamagnetic Iron Oxide Particles Using a Clinical 1.5-T Magnetic Resonance Scanner"; Cancer Research; bearing a date of Feb. 15, 2007; pp. 1555-1562; vol. 67, No. 4; American Association for Cancer Research; located at: www.aacrjournals.org.

Zheng et al.; "Ferromagnetism and Stability of Half-Metallic MnSb and MnBi in the strained Zinc-Blende Structure: Predictions from Full Potential and Pseudopotential Calculations"; Physical Review; 2004; pp. 144415-1 to 144415-9; vol. 69; The American Physical Society.

PCT International Search Report; International App. No. PCT/US2010/001573; bearing a date of Jul. 30, 2010; pp. 1-2.

\* cited by examiner

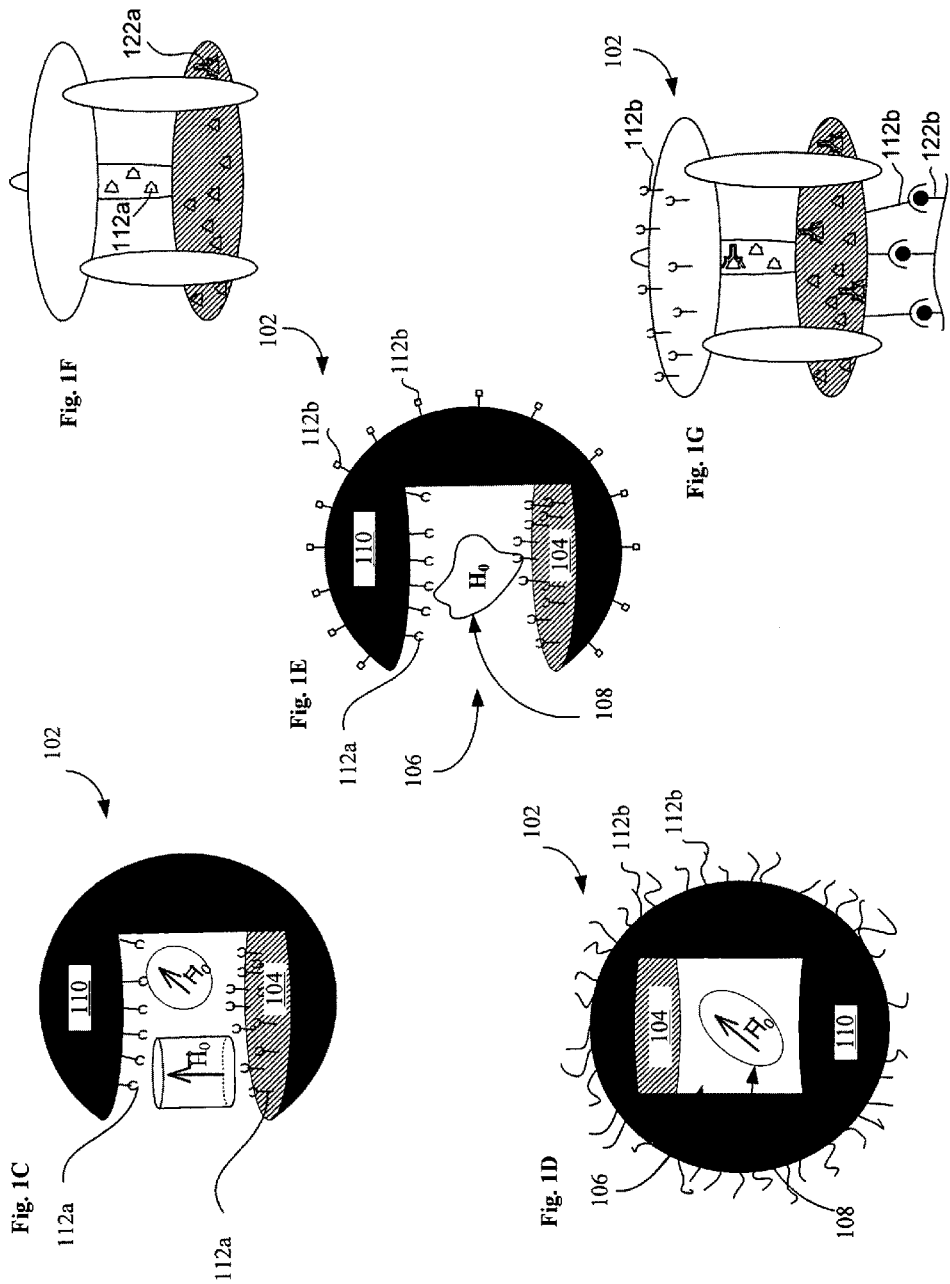

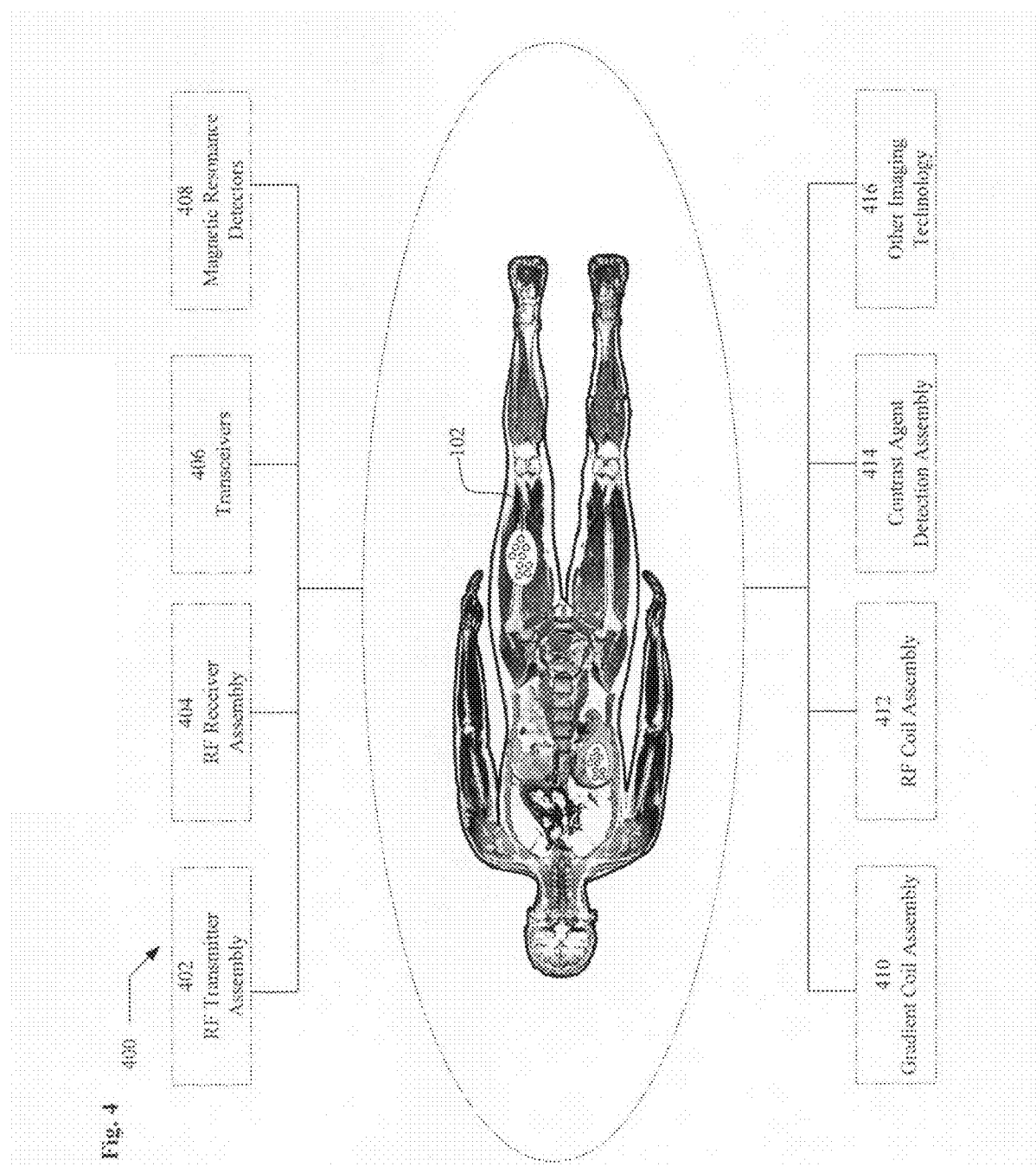

1500 — Start → 1510 detecting a spatial distribution of a magnetic resonance event associated with a targeted biological sample exposed to a surface-defined void of one or more selectively-targeted ferromagnetic microstructures, the one or more selectively-targeted ferromagnetic microstructures configured to generate a static magnetic field within the surface-defined void and configured to affect a magnetic resonance relaxation process associated with the biological sample at

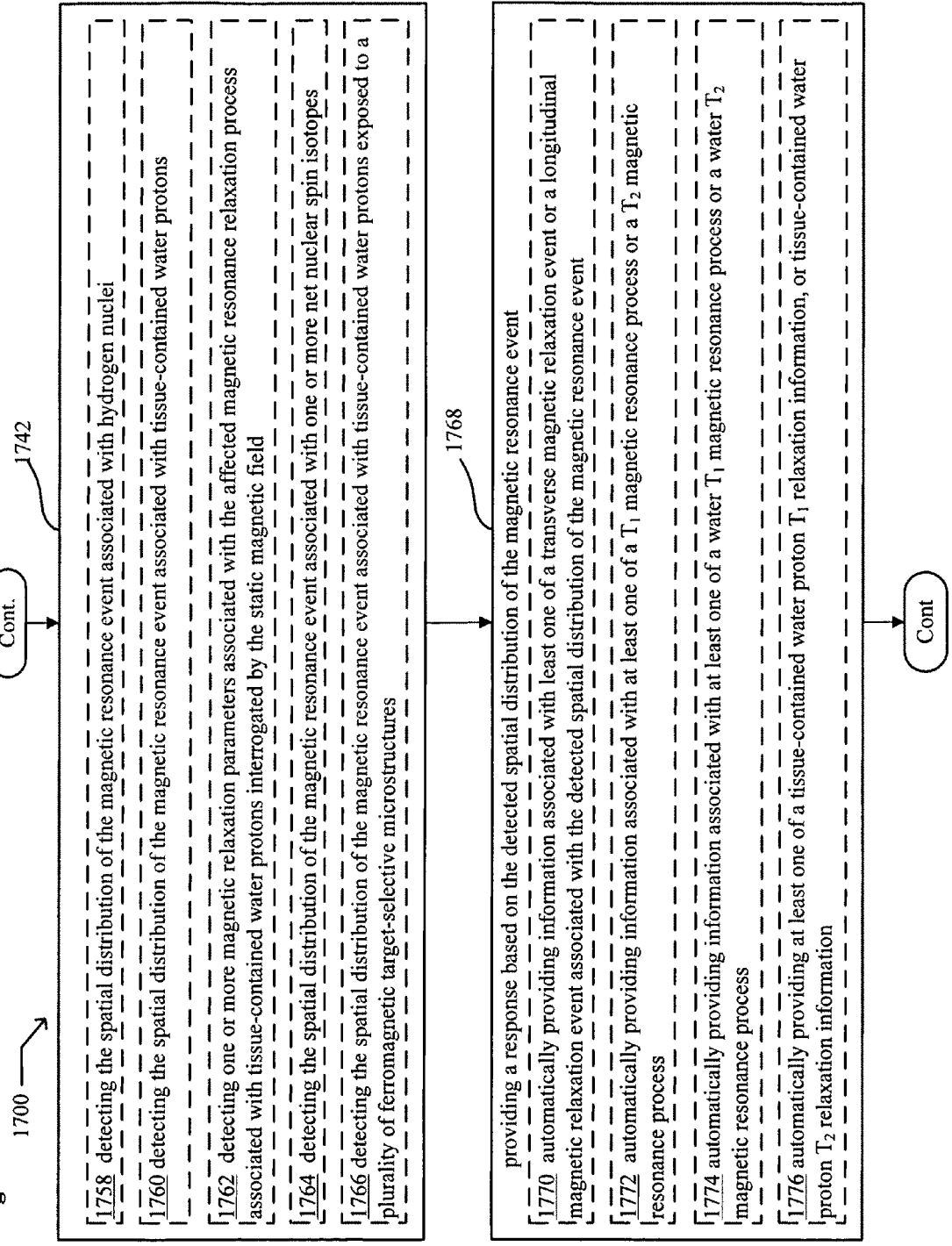

Fig. 17E

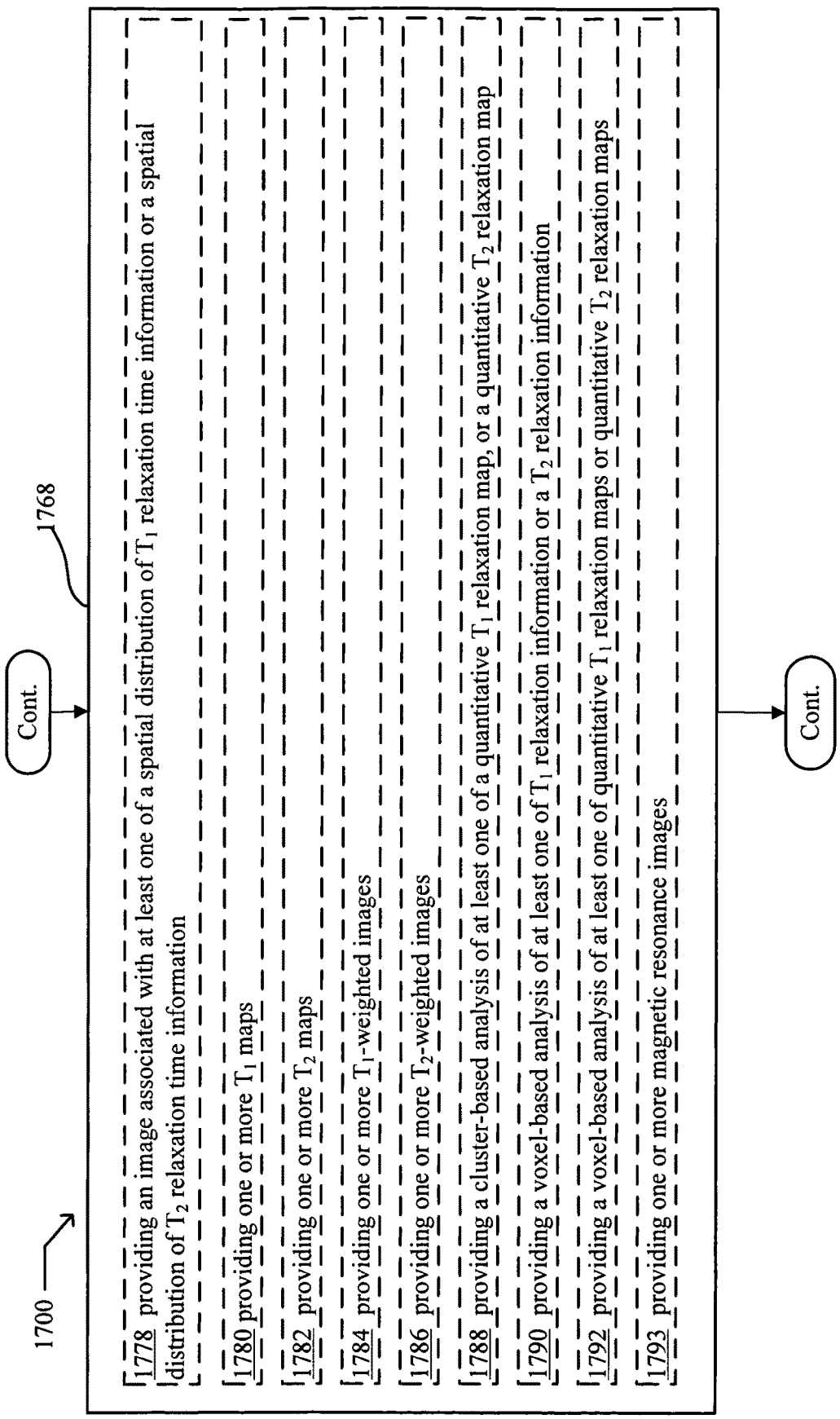

1700

1768

1778 providing an image associated with at least one of a spatial distribution of $T_1$ relaxation time information or a spatial distribution of $T_2$ relaxation time information 1780 providing one or more $T_1$ maps 1782 providing one or more $T_2$ maps 1784 providing one or more $T_1$-weighted images 1786 providing one or more $T_2$-weighted images 1788 providing a cluster-based analysis of at least one of a quantitative $T_1$ relaxation map, or a quantitative $T_2$ relaxation map 1790 providing a voxel-based analysis of at least one of $T_1$ relaxation information or a $T_2$ relaxation information 1792 providing a voxel-based analysis of at least one of quantitative $T_1$ relaxation maps or quantitative $T_2$ relaxation maps 1793 providing one or more magnetic resonance images

Fig. 17L

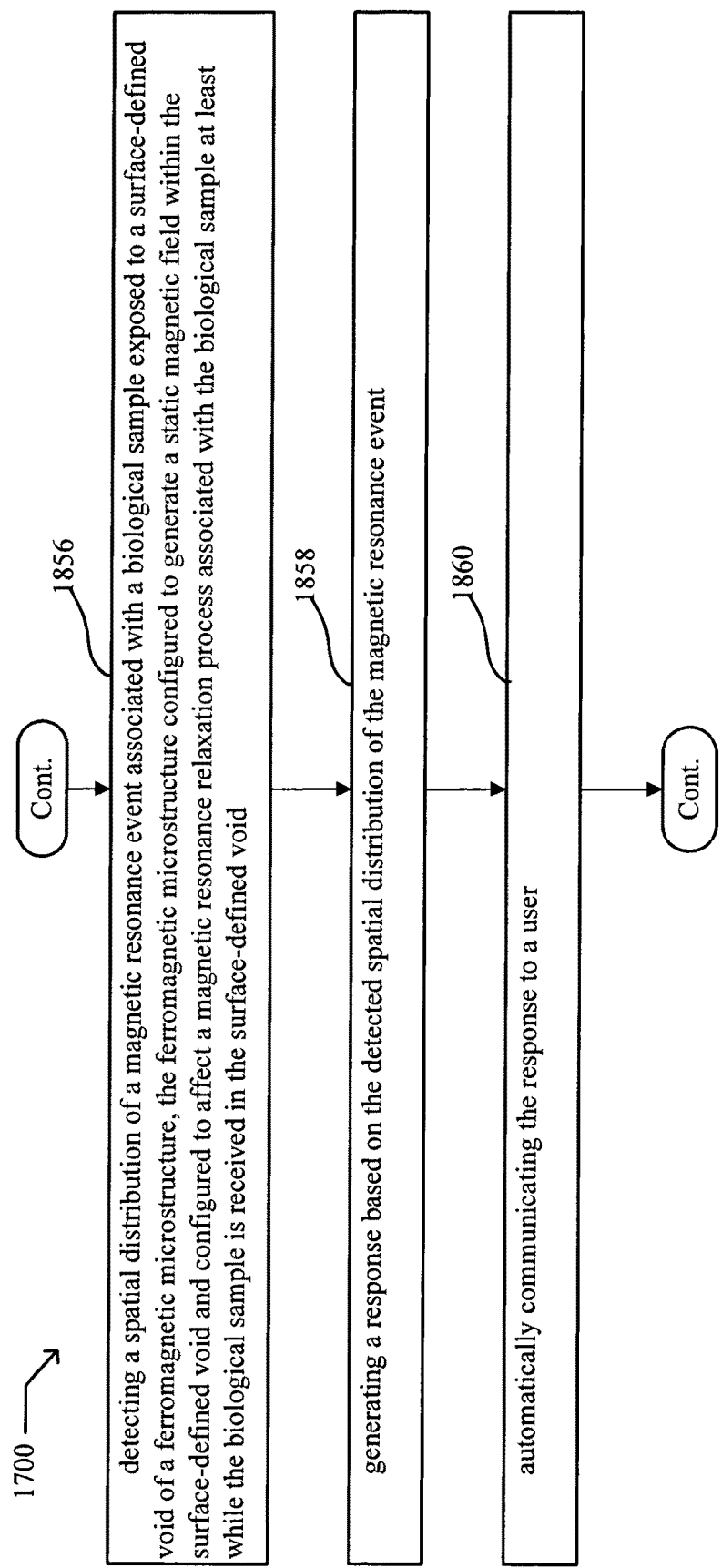

1700

1856 — detecting a spatial distribution of a magnetic resonance event associated with a biological sample exposed to a surface-defined void of a ferromagnetic microstructure, the ferromagnetic microstructure configured to generate a static magnetic field within the surface-defined void and configured to affect a magnetic resonance relaxation process associated with the biological sample at least while the biological sample is received in the surface-defined void 1858 — generating a response based on the detected spatial distribution of the magnetic resonance event 1860 — automatically communicating the response to a user

Fig. 17N

1700 →

1868 detecting a spatial distribution of a magnetic resonance event associated with a targeted biological sample exposed to a surface-defined void of one or more selectively-targeted ferromagnetic microstructures, the one or more selectively-targeted ferromagnetic microstructures configured to generate a static magnetic field within the surface-defined void and configured to affect a magnetic resonance relaxation process associated with the biological sample at least while the biological sample is received in the surface-defined void 1870 detecting the spatial distribution of the magnetic resonance event associated with one or more ferromagnetic microstructures selectively-targeted to at least one cell surface receptor targeting moiety 1872 detecting the spatial distribution of the magnetic resonance event associated with one or more ferromagnetic microstructures selectively-targeted to include at least one transmembrane receptor targeting moiety 1874 detecting the spatial distribution of the magnetic resonance event associated with one or more ferromagnetic microstructures selectively-targeted to at least one antigen-targeting moiety 1876 detecting the spatial distribution of the magnetic resonance event associated with one or more ferromagnetic microstructures selectively-targeted to at least one immune-receptor targeting moiety 1878 detecting the spatial distribution of the magnetic resonance event associated with one or more ferromagnetic microstructures selectively-targeted to at least one folate receptor targeting moiety 1880 detecting the spatial distribution of the magnetic resonance event associated with one or more ferromagnetic microstructures selectively-targeted to at least one nucleotide binding moiety 1882 detecting the spatial distribution of the magnetic resonance event associated with one or more ferromagnetic microstructures selectively-targeted to at least one oligomucleotide binding moiety 1884 detecting the spatial distribution of the magnetic resonance event associated with one or more ferromagnetic microstructures selectively-targeted to at least one oligodeoxyribonucleotide binding moiety 1886 detecting the spatial distribution of the magnetic resonance event associated with one or more ferromagnetic microstructures selectively-targeted to at least one oligoribonucleotide binding moiety

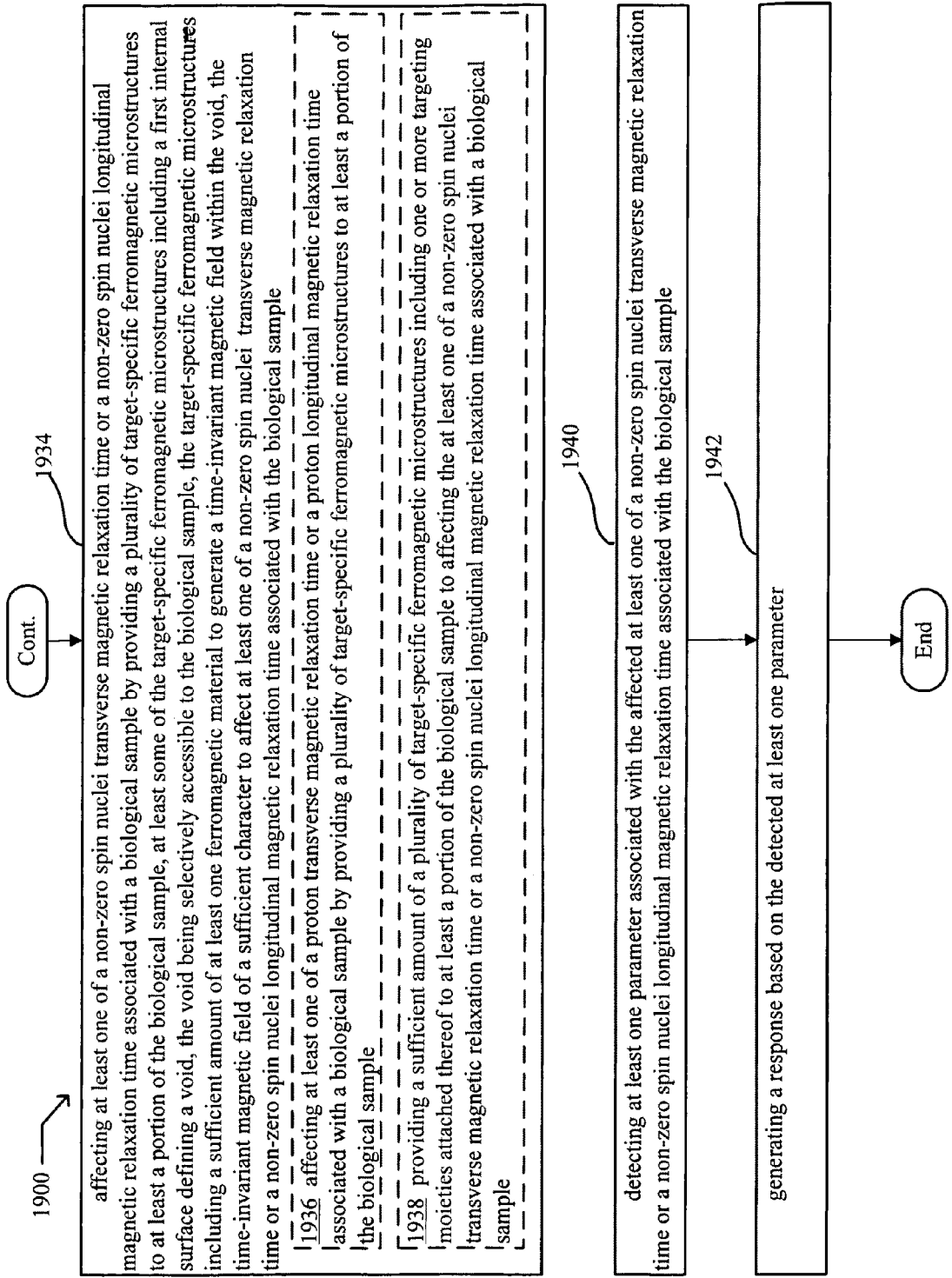

SYSTEMS, DEVICES, METHODS, AND COMPOSITIONS INCLUDING FUNCTIONALIZED FERROMAGNETIC STRUCTURES

CROSS-REFERENCE TO RELATED APPLICATIONS

The present application is related to and claims the benefit of the earliest available effective filing dates from the following listed applications (the "Related Applications") (e.g., claims earliest available priority dates for other than provisional patent applications or claims benefits under 35 U.S.C. §116(e) for provisional patent applications, for any and all parent, grandparent, great-grandparent, etc. applications of the Related Applications). All subject matter of the Related Applications and of any and all parent, grandparent, great-grandparent, etc. applications of the Related Applications is incorporated herein by reference to the extent such subject matter is not inconsistent herewith.

RELATED APPLICATIONS

The present application is related to U.S. patent application Ser. No. 12/455,273, entitled SYSTEMS, DEVICES, METHODS, AND COMPOSITIONS INCLUDING FERROMAGNETIC STRUCTURES, naming Roderick A. Hyde, Jordin T. Kare, and Wayne R. Kindsvogel as inventors, filed 29, May, 2009.

The present application is related to U.S. patent application Ser. No. 12/455,297, entitled SYSTEMS, DEVICES, METHODS, AND COMPOSITIONS INCLUDING TARGETED FERROMAGNETIC STRUCTURES, naming Roderick A. Hyde, Jordin T. Kare, and Wayne R. Kindsvogel as inventors, filed 29, May, 2009.

The present application is related to U.S. patent application Ser. No. 12/455,302, entitled SYSTEMS, DEVICES, METHODS, AND COMPOSITIONS INCLUDING SELECTIVELY ACCESSIBLE FERROMAGNETIC STRUCTURES, naming Roderick A. Hyde, Jordin T. Kare, and Wayne R. Kindsvogel as inventors, filed 29, May, 2009.

The present application is related to U.S. patent application Ser. No. 12/455,300, entitled NON-EXTERNAL STATIC MAGNETIC FIELD IMAGING SYSTEMS, DEVICES, METHODS, AND COMPOSITIONS, naming Roderick A. Hyde, Jordin T. Kare, and Wayne R. Kindsvogel as inventors, filed 29, May, 2009.

The present application is related to U.S. patent application Ser. No. 12/455,299, entitled MULTIPLEX IMAGING SYSTEMS, DEVICES, METHODS, AND COMPOSITIONS INCLUDING FERROMAGNETIC STRUCTURES, naming Roderick A. Hyde, Jordin T. Kare, and Wayne R. Kindsvogel as inventors, filed 29, May, 2009.

SUMMARY

In an aspect, the present disclosure is directed to, among other things, a method for obtaining a non-external magnetic field resonance image of a region within a biological subject. The method includes, but is not limited to, detecting (e.g., assessing, calculating, evaluating, determining, gauging, measuring, monitoring, quantifying, resolving, sensing, or the like) a spatial distribution of a magnetic resonance event (e.g., nuclear magnetic information, RF information, an RF signal, a nuclear magnetic resonance, an in vivo magnetic resonance event, or the like) associated with one or more net nuclear spin isotopes exposed to a plurality of target-selective microstructures configured to generate a static magnetic field within one or more surface-defined voids and to affect a magnetic resonance relaxation process associated with the net nuclear spin isotopes interrogated by the generated static magnetic field.

In an aspect, the present disclosure is directed to, among other things, a nuclear magnetic resonance imaging composition. The nuclear magnetic resonance imaging composition includes, but is not limited to, a plurality of ferromagnetic microstructures. In an embodiment, one or more of the plurality of ferromagnetic microstructures include, but are not limited to, a first internal surface defining a void that is accessible to a biological sample. In an embodiment, one or more of the plurality of ferromagnetic microstructures are configured to generate a time-invariant magnetic field within at least a portion of the void. In an embodiment, at least one of the plurality of ferromagnetic microstructures includes one or more targeting moieties attached thereof.

In an aspect, the present disclosure is directed to, among other things, a composition. The composition includes, but is not limited to, one or more selectively-accessible ferromagnetic microstructures, at least one of the one or more selectively-accessible ferromagnetic microstructures including at least a first internal surface defining a void. In an embodiment, the void is configured to be selectively-accessible to a biological sample. In an embodiment, at least one of the one or more selectively-accessible ferromagnetic microstructures includes a sufficient amount of one or more ferromagnetic materials to generate a time-invariant magnetic field within the void.

In an aspect, the present disclosure is directed to, among other things, an imaging system. The imaging system includes, but is not limited to, a plurality of ferromagnetic microstructures. In an embodiment, one or more of the plurality of ferromagnetic microstructures include, but are not limited to, a first internal surface defining one or more voids. In an embodiment, at least one of the one or more voids is configured to be accessible to a biological sample. In an embodiment, one or more of the plurality of ferromagnetic microstructures include a sufficient amount of one or more ferromagnetic materials to generate a time-invariant magnetic field within at least a portion of at least one of the one or more voids.

In an aspect, the present disclosure is directed to, among other things, a nuclear magnetic resonance imaging system. The nuclear magnetic resonance imaging system includes, but is not limited to, a plurality of ferromagnetic microstructures. In an embodiment, one or more of the plurality of ferromagnetic microstructures include, but are not limited to, a first internal surface defining a void configured to be selectively-accessible to a biological sample. In an embodiment, one or more of the plurality of ferromagnetic microstructures include, but are not limited to, a sufficient amount of one or more ferromagnetic materials to generate a time-invariant magnetic field within the void.

In an aspect, the present disclosure is directed to, among other things, a system. The system includes, but is not limited to, circuitry for acquiring information associated with an in vivo magnetic resonance event generated by nuclear magnetic resonance detectable nuclei received in one or more voids of a plurality of ferromagnetic microstructures configured to generate a static magnetic field within the void. The system can include, but is not limited to, circuitry for generating a response based on acquired information. In an embodiment, the system can include, but is not limited to, circuitry for communicating the generated response to a user. In an embodiment, the system can include, but is not limited to, circuitry for generating a radio frequency magnetic field of a character and for a sufficient time to excite at least some of the nuclear magnetic resonance detectable nuclei received in one or more voids of the plurality of ferromagnetic microstructures.

In an aspect, the present disclosure is directed to, among other things, an apparatus. The apparatus includes, but is not limited to, means for affecting an in vivo magnetic resonance relaxation process associated with a biological sample, in the absence of an externally generated magnetic field. The apparatus can include, but is not limited to, means for acquiring at least one spatial distribution parameter of a magnetic resonance event associated with the affected in vivo magnetic resonance relaxation process. The apparatus can include, but is not limited to, means for generating a response based on at least one acquired spatial distribution parameter.

In an aspect, the present disclosure is directed to, among other things, a computer program product including signal-bearing media containing computer instructions which, when run on a computing device, cause the computing device to implement a method including detecting a spatial distribution of a magnetic resonance event associated with a biological sample exposed to a surface-defined void of a ferromagnetic microstructure configured to generate a static magnetic field within the surface-defined void and configured to affect a magnetic resonance relaxation process associated with the biological sample at least while the biological sample is received in the surface-defined void. In an embodiment, the computer program product includes signal-bearing media containing computer instructions which, when run on a computing device, cause the computing device to implement a method including, but not limited to, generating a response based on the detected spatial distribution of the magnetic resonance event. In an embodiment, the computer program product includes signal-bearing media containing computer instructions which, when run on a computing device, cause the computing device to implement a method including, but not limited to, communicating the response to a user.

In an aspect, the present disclosure is directed to, among other things, a method for obtaining magnetic resonance information (e.g., spectral information, an image, a spectrum, a magnetic resonance scan, RF information, or the like) of a region within a biological subject without the need or use of an external-magnet. The method includes, but is not limited to, detecting a spatial distribution of a magnetic resonance event associated with a targeted biological sample exposed to a surface-defined void of a ferromagnetic microstructure configured to generate a static magnetic field within the surface-defined void and configured to affect a magnetic resonance relaxation process associated with the biological sample at least while the biological sample is received in the surface-defined void. The method can include, but is not limited to, generating a response based on the detected spatial distribution of the magnetic resonance event.

In an aspect, the present disclosure is directed to, among other things, a method for obtaining a non-external magnetic field resonance image of a region within a biological subject. The method includes, but is not limited to, detecting a spatial distribution of a magnetic resonance event associated with one or more nuclear magnetic resonance detectable nuclei exposed to a plurality of target-selective microstructures. In an embodiment, at least a portion of the plurality of target-selective microstructures includes, but is not limited to, one or more surface-defined voids. In an embodiment, at least a portion of the plurality of target-selective microstructures is configured to generate a static magnetic field within the one or more surface-defined voids and configured to affect a magnetic resonance relaxation process associated with the nuclear magnetic resonance detectable nuclei exposed to the generated static magnetic field. The method can include, but is not limited to, providing a response based on the detected spatial distribution of the magnetic resonance event.

In an aspect, a method includes, but is not limited to, detecting regional information associated with a magnetic resonance event generated by in vivo target tissue-contained non-zero spin nuclei (e.g., nuclei having spin quantum number I>0, spin-half particles, spin ½ nuclei, $^1$H (I=½), $^2$H (I=1), $^{13}$C (I=½), $^{19}$F (I=½), $^{31}$P (I=½), $^{23}$Na (I=3/2), or the like) exposed to one or more voids of a plurality of ferromagnetic microstructures configured to generate a static magnetic flux density within the void. The method can include, but is not limited to, generating a response based on the detected regional information.

In an aspect, the present disclosure is directed to, among other things, a method for obtaining magnetic resonance information of a region within a biological subject in absence of an externally generated magnetic field (other than the Earth's magnetic field) (e.g., a strong external magnetic field, a static magnetic field, or the like). The method includes, but is not limited to, monitoring a magnetic resonance event generated by net nuclear spin isotopes present in a biological sample received in a void of a ferromagnetic microstructure configured to generate a static magnetic field within the void. The method can include, but is not limited to, providing a response based on the monitored magnetic resonance event.

In an aspect, a method includes, but is not limited to, affecting at least one of a non-zero spin nuclei transverse magnetic relaxation time or a non-zero spin nuclei longitudinal magnetic relaxation time associated with a biological sample by providing a plurality of ferromagnetic microstructures to at least a portion of the biological sample, at least some of the plurality of ferromagnetic microstructures including a first internal surface defining a void selectively accessible to the biological sample. In an embodiment, the plurality of ferromagnetic microstructures include a sufficient amount of at least one ferromagnetic material to generate a time-invariant magnetic field within the void. In an embodiment, the time-invariant magnetic field is of a sufficient character to affect at least one of a non-zero spin nuclei transverse magnetic relaxation time or a non-zero spin nuclei longitudinal magnetic relaxation time associated with the biological sample.

In an aspect, the present disclosure is directed to, among other things, a multiplex nuclear magnetic resonance imaging composition. The multiplex nuclear magnetic resonance imaging composition includes, but is not limited to, a plurality of ferromagnetic microstructure sets. In an embodiment, each ferromagnetic microstructure set includes, but is not limited to, one or more ferromagnetic microstructures including an accessible internal void. In an embodiment, one or more of the ferromagnetic microstructures are configured to generate a characteristic time-invariant magnetic field within the accessible internal void. In an embodiment, at least one of the ferromagnetic microstructure sets includes, but is not limited to, a different characteristic time-invariant magnetic field from another of the ferromagnetic microstructure sets.

In an aspect, the present disclosure is directed to, among other things, a multiplex imaging method. The multiplex imaging method includes, but is not limited to, affecting at least one of a non-zero spin nuclei transverse magnetic relaxation time (e.g., a proton transverse magnetic relaxation time) or a non-zero spin nuclei longitudinal magnetic relaxation time (e.g., a proton longitudinal magnetic relaxation time) associated with a biological sample by providing a plurality of ferromagnetic microstructure sets. In an embodiment, each ferromagnetic microstructure set includes one or more ferromagnetic microstructures configured to include an accessible internal void and configured to generate a characteristic time-invariant magnetic field within the accessible internal void. In an embodiment, at least one of the ferromagnetic microstructure sets includes a different characteristic time-invariant magnetic field from another of the ferromagnetic microstructure sets.

In an aspect, the present disclosure is directed to, among other things, a method of multiplex interrogation of a biological sample. The method includes, but is not limited to, detecting nuclear magnetic resonance information generated by in vivo nuclear magnetic resonance detectable nuclei exposed to one or more internal-surface-defined voids of a plurality of different ferromagnetic microstructures. In an embodiment, the plurality of different ferromagnetic microstructures are configured to generate a static magnetic flux density within at least a portion of the one or more internal-surface-defined voids and configured to affect a magnetic resonance relaxation process associated with the in vivo nuclear magnetic resonance detectable nuclei while the in vivo nuclear magnetic resonance detectable nuclei are received in at least one of the one or more internal-surface-defined voids.

In an aspect, a method includes, but is not limited to, detecting a magnetic resonance event associated with one or more nuclear magnetic resonance detectable nuclei exposed to a static magnetic field within one or more surface-defined voids of a plurality of target-selective microstructures. In an embodiment, detecting the magnetic resonance event includes associated detecting the magnetic resonance information associated with one or more nuclear magnetic resonance detectable nuclei exposed to a static magnetic field within one or more selectively-accessible voids of a plurality of target-selective microstructures.

In an aspect, the present disclosure is directed to, among other things, an imaging system. The imaging system includes, but is not limited to, a plurality of ferromagnetic microstructures. In an embodiment, one or more of the plurality of ferromagnetic microstructures are configure to include an external surface and an internal surface defining a void. In an embodiment, one or more of the plurality of ferromagnetic microstructures are configured to generate a time-invariant magnetic field within at least a portion of the void. In an embodiment, the void is accessible to a biological sample. In an embodiment, at least one of the external surface or the internal surface is configured to include one or more functional groups. In an embodiment, at least one of the external surface or the internal surface is configured to include one or more of a bio-compatible functional group, a charge functional group, a chemically reactive functional group, a hydrophilic functional group, a hydrophobic functional group, or an organofunctional group. In an embodiment, the external surface includes a bio-compatible functional group, a charge functional group, a chemically reactive functional group, a hydrophilic functional group, a hydrophobic functional group, or an organofunctional group, and the internal surface includes a different one of a bio-compatible functional group, a charge functional group, a chemically reactive functional group, a hydrophilic functional group, a hydrophobic functional group, or an organofunctional group. The imaging system can include, but is not limited to, a radio frequency transmitter configured to generate a radio frequency signal. The imaging system can include, but is not limited to, one or more coils configured to generate one or more radio frequency pulses. The imaging system can include, but is not limited to, means for acquiring at least one spatial distribution parameter of a magnetic resonance event associated with one or more non-zero spin nuclei of a biological sample present within the void. In an embodiment, the imaging system includes a radio frequency receiver configured to acquire radio frequency information emitted by the biological sample.

In an aspect, a method includes, but is not limited to, detecting a spatial distribution of a magnetic resonance event associated with a targeted biological sample exposed to a surface-defined void of one or more selectively-targeted ferromagnetic microstructures configured to generate a static magnetic field within the surface-defined void and configured to affect a magnetic resonance relaxation process associated with the biological sample at least while the biological sample is received in the surface-defined void. In an embodiment, detecting the spatial distribution of a magnetic resonance event associated with a targeted biological sample exposed to a surface-defined void of one or more selectively-targeted ferromagnetic microstructures includes detecting the spatial distribution of the magnetic resonance event associated with one or more ferromagnetic microstructures selectively-targeted to at least one cell surface receptor targeting moiety. In an embodiment, detecting the spatial distribution of a magnetic resonance event associated with a targeted biological sample exposed to a surface-defined void of one or more selectively-targeted ferromagnetic microstructures includes detecting the spatial distribution of the magnetic resonance event associated with one or more selectively-targeted ferromagnetic microstructures including at least one of a transmembrane receptor targeting moiety, an antigen-targeting moiety, an immune-receptor targeting moiety, a folate receptor targeting moiety, a nucleotide binding moiety, an oligonucleotide binding moiety, an oligodeoxyribonucleotide binding moiety, an oligoribonucleotide binding moiety. In an embodiment, detecting a spatial distribution of a magnetic resonance event associated with a targeted biological sample exposed to a surface-defined void of one or more selectively-targeted ferromagnetic microstructures includes detecting the spatial distribution of the magnetic resonance event associated with one or more selectively-targeted ferromagnetic microstructures including at least one of an amyloid binding moiety or a β-amyloid binding moiety. In an embodiment, detecting a spatial distribution of a magnetic resonance event associated with a targeted biological sample exposed to a surface-defined void of one or more selectively-targeted ferromagnetic microstructures includes detecting the spatial distribution of the magnetic resonance event associated with one or more ferromagnetic microstructures selectively-targeted to one or more genomic targets. The method may further include generating a response based on the detected spatial distribution of the magnetic resonance event.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1A-1G are perspective views of ferromagnetic microstructures according to multiple illustrated embodiments.

FIG. 4 is a schematic diagram of a system including a pluralities of ferromagnetic microstructures according to one illustrated embodiment.

FIGS. 15A-15D are flow diagrams of a method according to one illustrated embodiment.

DETAILED DESCRIPTION

Figure 1A:
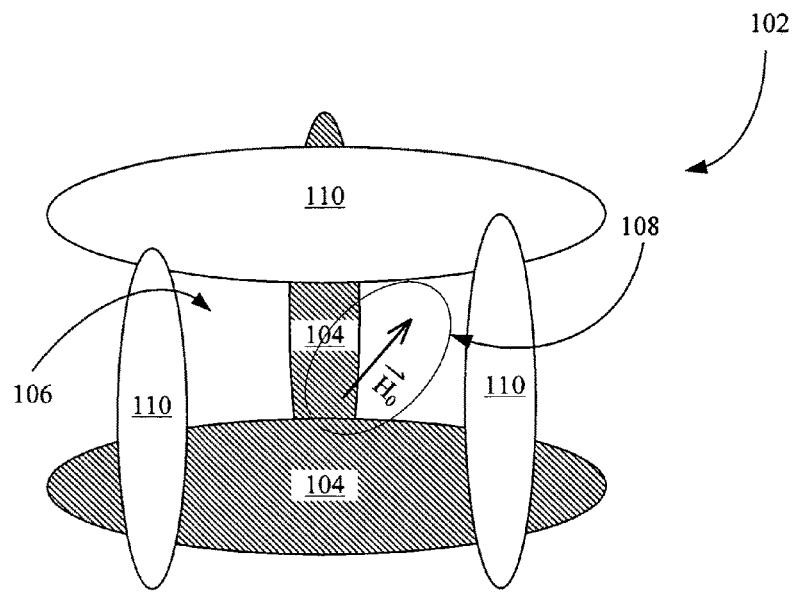
Figure 1B:
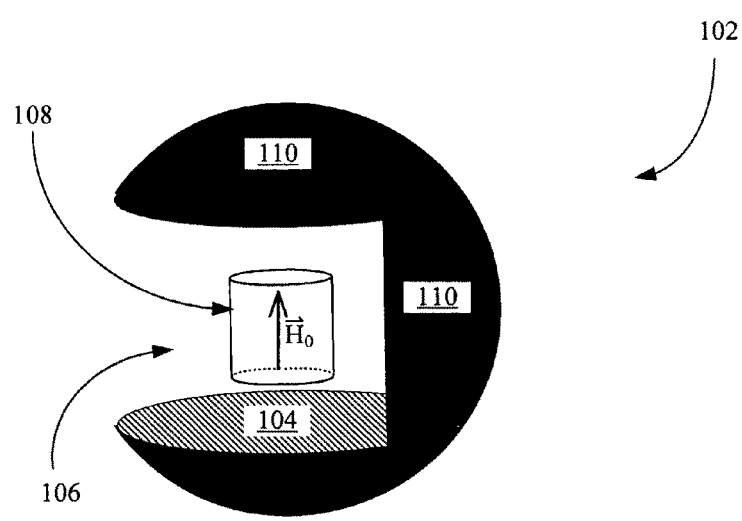

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Nuclear Magnetic Resonance (NMR) is a quantum mechanical phenomenon in which a system of spins (e.g., non-zero spin nuclei, or the like) placed in a static magnetic field $\vec{H}_0$ resonantly absorbs energy applied at a certain electromagnetic frequency. In the presence of the static magnetic field, the non-zero spin nuclei precess about the magnetic field's axis at an angular frequency $\omega_0$. See, e.g., Shankar R., *Principles of Quantum Mechanics*, 2nd edition, Plenum (1994). If interrogated with a short, precisely-tuned burst of radio frequency waves, the non-zero spin nuclei will momentarily precess off axis and, in the process of returning to their original orientation, will resound with a brief radio frequency signal of their own. See, e.g., U.S. Department of Energy, *Magnetic Resonance Imager: Project Fact Sheet* (Jan. 13, 2003). The time constant associated with the elapsed time for the spin system to return to thermal equilibrium along the static magnetic field's axis is known as "longitudinal relaxation time" or "spin-lattice relaxation time," often denoted as $T_1$. An additional time constant associated with the elapsed time in which the transverse magnetization diminishes by the principle of maximal entropy is known as "spin-spin relaxation time" or "transverse relaxation time," often denoted as $T_2$. NMR (e.g., magnetic resonance imaging, or the like) and other spectroscopy techniques and methodologies exploit these phenomena to obtaining information regarding, for example, chemical and physical microscopic properties of a sample or biological subject. A more detailed discussion of magnetic resonance may be found in, for example, the following documents (the contents of which are incorporated herein by reference): C. P. Slichter, *Principles of Magnetic Resonance*, 3$^{rd}$ ed., Springer-Verlag, Berlin, pp. 1-63 (1990); J. D. Roberts, *Nuclear Magnetic Resonance*, Mc-Graw-Hill, New York, pp. 1-19 (1959) Cohen-Tannoudji et al., *Quantum Mechanics*, Vol. 1, New York, N.Y.: Wiley (1977); WO 2009/027973 (published Mar. 5, 2009), WO 2009/029880 (published Mar. 5, 2009), and WO 2009/029896 (published Mar. 5, 2009).

Often, a sample or biological subject is placed in the bore or within an interior of an external magnet (e.g., a permanent magnet, resistive magnet, a superconducting magnet, or the like) that generates the static magnetic field $\vec{H}_0$. For example, conventional MRI employs, among other things, an external primary or main magnet (for generating a static magnetic field $\vec{H}_0$), as well as magnetic field gradient coils and radio frequency coils, to produce detailed images of organs, soft tissues, bone, and other internal body structures. See, e.g., U.S. Pat. No. 7,495,439 (issued Feb. 24, 2009) (the contents of which is incorporated herein by reference).

As a non-limiting example, certain systems, devices, methods, and compositions described herein provide for the detection of regional information associated with a magnetic resonance event generated by, for example, in vivo target non-zero spin nuclei without the use or need of an external (ex vivo) magnet (e.g., a permanent magnet, resistive magnet, a superconducting magnet, or the like). An aspect includes systems, devices, methods, and compositions for obtaining magnetic resonance information of one or more regions within a biological subject in absence of an externally generated static magnetic field. An aspect includes systems, devices, methods, and compositions for imaging at least one of a $T_1$ magnetic relaxation time or a $T_2$ magnetic relaxation time associated with in vivo non-zero spin nuclei.

An aspect includes non-external magnetic field imaging systems, devices, methods, and compositions. A non-limiting approach includes systems, devices, methods, and compositions for obtaining a non-external magnetic field resonance image of a region within a biological subject An aspect includes systems, devices, and methods employing compositions including, among other things, one or more ferromagnetic microstructures. A non-limiting approach includes nuclear magnetic resonance imaging systems, devices, and methods including, among other things, compositions having a plurality of ferromagnetic microstructure sets. A non-limiting approach includes systems, devices, and methods including, among other things, one or more ferromagnetic contrast agent compositions. A non-limiting approach includes systems, devices, and methods including a nuclear magnetic resonance imaging composition having a plurality of ferromagnetic microstructures.

Referring to FIGS. 1A through 1G, in an embodiment, a nuclear magnetic resonance imaging composition includes, but is not limited to, one or more ferromagnetic microstructures 102. In an embodiment, one or more of the ferromagnetic microstructures 102 include, but are not limited to, at least a first internal surface 104 defining a void 106 accessible to a biological sample. In an embodiment, one or more of the ferromagnetic microstructures 102 include at least an outer surface 110. In an embodiment, one or more of the ferromagnetic microstructures 102 are configured to generate one or more time-invariant magnetic fields 108 within at least a portion of the void 106. In an embodiment, the time-invariant magnetic field 108 within the void 106 includes a substantially homogeneous polarizing magnetic field region.

In an embodiment, at least one of the ferromagnetic microstructures 102 includes one or more voids 106. The at least a first internal surface 104 can define one or more_voids 106 having any geometric form including regular or irregular forms and may have a cross-section of substantially any shape including, but not limited to, circular, triangular, square, rectangular polygonal, regular or irregular shapes, or the like, as well as other symmetrical and asymmetrical shapes, or combinations thereof.

In an embodiment, a plurality of ferromagnetic microstructures includes two or more of the ferromagnetic microstructures 102. In an embodiment, the plurality of ferromagnetic microstructures include one or more different time-invariant magnetic field 108 strengths. In an embodiment, one or more of the ferromagnetic microstructures 102 are configured to include one or more different void 106 dimensions. In an embodiment, the plurality of ferromagnetic microstructures include at least a first plurality of ferromagnetic microstructures 102 sized and dimensioned to generate a first magnetic flux density within the void 106 and a second plurality of ferromagnetic microstructures 102 sized and dimensioned to generate a second magnetic flux density within the void 106, the second magnetic flux density different from the first magnetic flux density.

In an embodiment, the plurality of ferromagnetic microstructures include at least a first plurality of ferromagnetic microstructures 102 configured to generate a time-invariant magnetic field 108 within the void 106 of a first magnetic field strength and a second plurality of ferromagnetic microstructures configured to generate a time-invariant magnetic field 108 within the void 106 of a second magnetic field strength, the second magnetic field strength different from the first magnetic field strength. In an embodiment, the plurality of ferromagnetic microstructures include at least a first plurality of ferromagnetic microstructures 102 configured to generate a time-invariant magnetic field 108 within the void 106 of a first magnetic field spatial distribution and a second plurality of ferromagnetic microstructures configured to generate a time-invariant magnetic field 108 within the void 106 of a second magnetic field spatial distribution, the second magnetic field spatial distribution different from the first magnetic field spatial distribution.

In an embodiment, the composition includes a plurality of ferromagnetic microstructures 102 including at least a first plurality of ferromagnetic microstructures sized and dimensioned to generate a time-invariant magnetic field 108 within the void 106 of a first magnetic field strength and a second plurality of ferromagnetic microstructures sized and dimensioned to generate a time-invariant magnetic field 108 within the void 106 of a second magnetic field strength. In an embodiment, the second magnetic field strength is different from the first magnetic field strength.

An aspect includes systems, devices, methods, and compositions including, among other things, microstructures including ferromagnetic materials. In an embodiment, one or more of the microstructures include one or more ferromagnetic materials.

Ferromagnetic materials include those materials having a Curie temperature, above which thermal agitation destroys the magnetic coupling giving rise to the alignment of the elementary magnets (electron spins) of adjacent atoms in a lattice (e.g., a crystal lattice). In an embodiment, one or more of the ferromagnetic microstructures 102 include one or more ferromagnets. Among ferromagnetic materials, examples include, but are not limited to, crystalline ferromagnetic materials, ferromagnetic oxides, materials having a net magnetic moment, materials having a positive susceptibility to an external magnetic field, non-conductive ferromagnetic materials, non-conductive ferromagnetic oxides, ferromagnetic elements (e.g., cobalt, gadolinium, iron, or the like), rare earth elements, ferromagnetic metals, ferromagnetic transition metals, materials that exhibit magnetic hysteresis, and the like, and alloys or mixtures thereof.

Further examples of ferromagnetic materials include, but are not limited to, chromium (Cr), cobalt (Co), copper (Cu), dysprosium (Dy), europium (Eu), gadolinium (Gd), iron (Fe), magnesium (Mg), neodymium (Nd), nickel (Ni), yttrium (Y), and the like. Further examples of ferromagnetic materials include, but are not limited to, chromium dioxide ($CrO_2$), copper ferrite ($CuOFe_2O_3$), europium oxide (EuO), iron (II, III) oxide ($FeOFe_2O_3$), iron (III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), and the like. Further examples of ferromagnetic materials include, but are not limited to, manganese arsenide (MnAs), manganese bismuth (MnBi), manganese (III) antimonide (MnSb), Mn—Zn ferrite, neodymium alloys, neodymium, Ni—Zn ferrite, and samarium-cobalt.

In an embodiment, one or more of the ferromagnetic microstructures 102 include at least one iron oxide. Among iron oxides, examples include, but are not limited to, copper ferrite ($CuOFe_2O_3$), iron (II, III) oxide ($FeOFe_2O_3$), iron (III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), ferric oxides, ferrous oxides, and the like. In an embodiment, one or more of the ferromagnetic microstructures 102 are configured to include one or more magnetic components.

In an embodiment, one or more of the ferromagnetic microstructures 102 include at least one electrically non-conductive ferromagnetic material. Among electrically non-conductive ferromagnetic materials, examples include, but are not limited to, ceramic magnets, ferrite, and the like. In an embodiment, one or more of the ferromagnetic microstructures 102 include at least one electrically non-conductive ferromagnetic oxide or ferrimagnetic oxide. In an embodiment, one or more of the ferromagnetic microstructures 102 include at least one electrically non-conductive ferromagnetic ceramic material or ferrimagnetic ceramic material.

In an embodiment, one or more of the ferromagnetic microstructures 102 include at least one ferromagnetic oxide. Among ferromagnetic oxides, examples include, but are not limited to, three main groups of ferrites: spinels, garnets, and magnetoplumbites. Spinels have the general formula $MOFe_2O_3$, $MFe_2O_4$, or $MFe_3O_4$ where M represents nickel (Ni), zinc (Zn), manganese (Mn), magnesium (Mg), lithium (Li), copper (Cu), cobalt (Co), ron (Fe) or other ion (e.g., divalent ions). Garnets have the general formula $3M_2O_3 \cdot 5Fe_2O_3$ or $M_3Fe_5O_{12}$, where M represents yttrium (Y) or one of the rare earth ions. Magnetoplumbites have the general formula $AM_{12}O_{19}$ (e.g., $BaFe_{12}O_{19}$, $SrFe_{12}O_{19}$, or the like); $(Pb, Mn)(Fe, Mn)_{12}O_{19}$; $MFe_{12}O_{19}$ or $MO \cdot 6Fe_2O_3$; where M is barium (Ba), Strontium (Sr) lead (Pb), aluminum (Al), gallium (Ga), chromium (Cr) or manganese (Mn). These ferromagnetic oxides can also be combined in many ways depending on a particular application. See, e.g., (the contents of which are incorporated herein by reference) U.S. Pat. No.

5,532,667 (issued Jul. 2, 1996) and Goldman A, *Modern Ferrite Technology*, 2$^{nd}$ Ed., Springer Science & Business (2006).

Further examples of ferromagnetic oxides include rare earth iron garnets having the general formula of $(3M_2O_3)C$ $(2Fe_2O_3)A(3Fe_2O_3)D$ where M is yttria or rare earth ion and (A,C,D) are lattice site. Further examples of ferromagnetic oxides include microwave or ferromagnetic garnets such as, for example, yttrium aluminum iron garnet or YIG $(Y_2Fe_5O_{12})$. In an embodiment, magnetization levels of microwave or ferromagnetic garnets are modified by substituting Al for Fe or combinations of Ho, Dy or Gd for Y. Further examples of ferromagnetic oxides include, but are not limited to, amorphous ferromagnetic oxides, ferromagnetic metal oxide, iron oxides, perovskite manganite, lanthanum strontium manganite, rare earth oxides, spinel ferrite, and the like. In an embodiment, one or more of the ferromagnetic microstructures 102 include at least one of chromium dioxide $(CrO_2)$ or europium oxide (EuO).

In an embodiment, one or more of the ferromagnetic microstructures 102 include at least one of chromium (Cr), cobalt (Co), copper (Cu), dysprosium (Dy), europium (Eu), gadolinium (Gd), iron (Fe), magnesium (Mg), neodymium (Nd) nickel (Ni), or yttrium (Y). In an embodiment, one or more of the ferromagnetic microstructures 102 include at least one of manganese (III) antimonide (MnSb), manganese arsenide (MnAs), or manganese bismuth (MnBi). In an embodiment, one or more of the ferromagnetic microstructures 102 include at least one of Mn—Zn ferrite or Ni—Zn ferrite. In an embodiment, one or more of the ferromagnetic microstructures 102 include one or more rare earth elements. In an embodiment, one or more of the ferromagnetic microstructures 102 include at least one of neodymium, neodymium alloys, or samarium-cobalt.

An aspect includes systems, devices, methods, and compositions including, among other things, microstructures including at least one of a ferromagnetic material or a ferrimagnetic material. In an embodiment, one or more of the ferromagnetic microstructures 102 include at least one ferrimagnetic material. In an embodiment, one or more of the ferromagnetic microstructures 102 include one or more ferrimagnets (e.g., soft ferrites, hard ferrites, or the like). Among ferrimagnetic materials, examples include, but are not limited to, ferrimagnetic oxides (e.g., ferrites, garnets, or the like). Further examples of ferrimagnetic materials include ferrites with a general chemical formula of $AB_2O_4$ (e.g., $CoFe_2O_4$, $MgFe_2O_4$, $ZnFe_2O_4$) where A and B represent various metal cations. In an embodiment, A is Mg, Zn, Mn, Ni, Co, or Fe(II); B is Al, Cr (III), Mn (III) or Fe(III); and O is oxygen. In an embodiment, A is a divalent atom of radius ranging from about 80 pm to about 110 pm (e.g., Cu, Fe, Mg, Mn, Zn, or the like), B is a trivalent atom of radius ranging from about 75 pm to about 90 pm, (e.g., Al, Fe, Co, Ti, or the like), and O is oxygen. Further examples of ferrimagnetic materials include iron ferrites with a general chemical formula $MOFe_2O_3$ (e.g., $CoFe_2O_4$, $Fe_3O_4$, $MgFe_2O_4$, or the like) where M is a divalent ion such as Fe, Co, Cu, Li, Mg, Ni, or Zn. Further examples of ferrimagnetic materials include materials having a magnetization compensation point, materials that are associated with a partial cancellation of antiferromagnetically aligned magnetic sublattices with different values of magnetic moments, or material having different temperature dependencies of magnetization. See e.g., Kageyama et al., Weak Ferrimagnetism, Compensation Point, and Magnetization Reversal in $Ni(HCOO)_2.2H_2O$, Physical Rev. B, 224422 (2003).

An aspect includes imaging systems, devices, methods, and compositions including, among other things, microstructure including one or more radio frequency transparent materials. See, e.g., U.S. Pat. No. 5,506,053 (issued Apr. 9, 1996) (the contents of which are incorporated herein by reference). A non-limiting approach includes imaging systems, devices, methods, and compositions including, among other things, ferromagnetic microstructures 102 including one or more radio frequency shielding materials. In an embodiment, one or more of the ferromagnetic microstructures 102 include a sufficient amount of a layer, a mesh, a conductive structure, or a conductive coating to limit the penetration of electromagnetic fields into a space within a ferromagnetic microstructure 102, by blocking them with a barrier made of conductive material. In an embodiment, one or more of the ferromagnetic microstructures 102 include a sufficient amount of a conductive material, and are configured, to redistribute electrical charges associated with an electrical field within the conducting material to cancel the electrical field's effects within the ferromagnetic microstructures interior.

In an embodiment, one or more of the ferromagnetic microstructures 102 include a sufficient amount of a high magnetic permeability metal alloys to draw the magnetic fields associated with the particular ferromagnetic microstructure 102 into themselves, and provide a path for the magnetic field lines around a shielded ferromagnetic microstructure 102. In an embodiment, one or more of the ferromagnetic microstructures 102 are configured to limit an external self-generated magnetic field moment. In an embodiment, one or more of the ferromagnetic microstructures 102 are configured to include a substantially U-shape magnetic structure (e.g., a horseshoe shaped magnet, or the like) that is configured to confine the magnetic field lines within a volumetric footprint occupied by the ferromagnetic microstructure 102. In an embodiment, at least one of the ferromagnetic microstructures 102 is configured to generate a constant magnetic field confined within a volumetric footprint occupied by the ferromagnetic microstructure 102. In an embodiment, one or more of the ferromagnetic microstructures 102 are configured to confine a generated magnetic filed to a region located within the ferromagnetic microstructure 102. In an embodiment, one or more of the ferromagnetic microstructures 102 are configured to include one or more magnetic structures. In an embodiment, one or more of the ferromagnetic microstructures 102 are configured limit an external self-generated magnetic field by including one or more magnetic structures forming a magnetic filed return path. In an embodiment, one or more of the ferromagnetic microstructures 102 are configured to include one or more magnetic dipoles. In an embodiment, one or more of the ferromagnetic microstructures 102 are configured to limit an external self-generated magnetic field. In an embodiment, one or more of the ferromagnetic microstructures 102 include one or more magnetic dipoles in a configuration that limits an external self-generated magnetic field associated with a ferromagnetic microstructure 102. In an embodiment, one or more of the ferromagnetic microstructures 102 include one or more magnetic dipoles in a configuration including unlike poles opposing each other. In an embodiment, one or more of the ferromagnetic microstructures 102 include a sufficient amount of a ferromagnetic material to generate one or more magnetic poles. In an embodiment, one or more of the ferromagnetic microstructures 102 include a sufficient amount of a ferrimagnetic material to generate one or more magnetic dipoles. In an embodiment, one or more of the ferromagnetic microstructures 102 include a sufficient amount of a ferrimagnetic material to generate one or more magnets.

In an embodiment, one or more of the ferromagnetic microstructures 102 include one or more conductive traces that are deposited, etched, sintered, or otherwise applied to a ferromagnetic microstructure 102 to form an electromagnetic shielding structure. For example, lithographic techniques can be use to form a conductive trace layout onto a surface of a ferromagnetic microstructure 102 or conductive trace layout onto a layer surrounding a ferromagnetic microstructure 102. The lithographic process for forming the conductive trace layouts can include for example, but not limited to, applying a resist film (e.g., spin-coating a photoresist film) onto the substrate, exposing the resist with an image of a circuit layout (e.g., the geometric pattern of one or more conductive traces), heat treating the resist, developing the resist, transferring the layout onto the substrate, and removing the remaining resist. Transferring the layout onto a ferromagnetic microstructure 102 can include, but is not limited to, using techniques like subtractive transfer, etching, additive transfer, selective deposition, impurity doping, ion implantation, and the like. Among conductive materials examples include, but are not limited to, metals (e.g., copper, nickel, or the like), metallic inks, metalized plastics, conductive polymers, conductive glasses, conductive composites, or the like.

In an embodiment, one or more of the ferromagnetic microstructures 102 include one or more radio frequency transparent materials. Among radio frequency transparent materials, examples include, but are not limited to, glass (e.g., glass fibers), KEVLAR®, thermoplastic materials (e.g., polyester or polyethylene terephthalate (PET), MYLAR®), polyimide (e.g., Kapton™), fluorinated ethylene propylene (FEP) (e.g., polytetrafluoroethylene (PTFE) TEFLON®), and the like. See, e.g., U.S. Pat. No. 7,236,142 (issued Jun. 26, 2007) (the contents of which are incorporated herein by reference).

In an embodiment, one or more of the ferromagnetic microstructures 102 are configured to limit penetration of electromagnetic fields into at least a portion of the void 106. In an embodiment, one or more of the ferromagnetic microstructures 102 are configured to limit an external self-generated field. In an embodiment, one or more of the ferromagnetic microstructures 102 are configured to limit an external self-generated field moment. In an embodiment, one or more of the ferromagnetic microstructures 102 include one or more radio frequency transparent coating materials. In an embodiment, one or more of the ferromagnetic microstructures 102 include one or more radio frequency shielding materials. In an embodiment, one or more of the ferromagnetic microstructures 102 include one or more conductive layers. In an embodiment, one or more of the ferromagnetic microstructures 102 include one or more RF-shielding cages (e.g., a Faraday cage). In an embodiment, an average major dimension of a hole in the RF-shielding cage is less than the wavelength of the shielded electromagnetic radiation.

In an embodiment, one or more of the ferromagnetic microstructures 102 include one or more RF-shields. For example, one or more of the ferromagnetic microstructures 102 can include one or more thin metal perforated coatings. The dimensions of the perforations are determined based on the wavelength of the interference to be limited or blocked by the RF shield. In an embodiment, an average major dimension of the perforations in the thin metal perforated coatings is less than the wavelength of the shielded electromagnetic radiation. In an embodiment, an average major dimension of the perforations in the thin metal perforated coatings is less than about ½ the wavelength of the shielded electromagnetic radiation. In an embodiment, an average major dimension of the perforations in the thin metal perforated coatings is less than about ¹⁄₁₀ the wavelength of the shielded electromagnetic radiation. See, e.g., U.S. Pat. No. 7,371,977 (issued May 13, 2008), the contents of which are incorporated herein by reference). In an embodiment, an average major dimension of the perforations in the thin metal perforated coatings range from less than about ¹⁄₁₀ the wavelength of the shielded electromagnetic radiation to less than about ½ the wavelength of the shielded electromagnetic radiation. In an embodiment, an average major dimension of the perforations in the thin metal perforated ranges from about ¹⁄₁₀ the wavelength of the shielded electromagnetic radiation to about a wavelength of the shielded electromagnetic radiation. In an embodiment, an average major dimension of the perforations in the thin metal perforated ranges from about ¹⁄₁₀ the wavelength of the shielded electromagnetic radiation to about ½ the wavelength of the shielded electromagnetic radiation.

An aspect includes a multiplex nuclear magnetic resonance imaging composition including among other things, a plurality of ferromagnetic microstructure sets. A non-limiting approach includes, among other things, multiplex MRI systems, devices, methods, and compositions including microstructure sets of varying internal magnetic field magnitudes. An aspect includes, among other things, multiplex nuclear magnetic resonance imaging systems, devices, methods, and compositions. A non-limiting approach includes, among other things, multiplex systems, devices, methods, and compositions. A non-limiting approach includes systems, devices, methods, and compositions of multiplex interrogation of a biological sample. A non-limiting approach includes systems, devices, methods, and compositions for obtaining a non-external magnetic field resonance image of a region within a biological subject.

In an embodiment, at least one of the ferromagnetic microstructure sets includes a different characteristic time-invariant magnetic field 108 from another of the ferromagnetic microstructure sets. In an embodiment, each ferromagnetic microstructure set includes one or more ferromagnetic microstructures configured to include an accessible internal void 106 and configured to generate a characteristic time-invariant magnetic field 108 within the accessible internal void 106. In an embodiment, each ferromagnetic microstructure set includes a different characteristic time-invariant magnetic field 108 magnitude. In an embodiment, each ferromagnetic microstructure set includes a different accessible internal void 106 dimension. In an embodiment, each ferromagnetic microstructure set includes a different ferromagnetic material. In an embodiment, each ferromagnetic microstructure set is configured to affect at least one of an in vivo non-zero spin nuclei transverse magnetic relaxation time or an in vivo non-zero spin nuclei longitudinal magnetic relaxation time.

In an embodiment, each ferromagnetic microstructure set comprises a different characteristic magnetic field spatial distribution. In an embodiment, a plurality of ferromagnetic microstructure sets include at least a first ferromagnetic microstructure set including one or more ferromagnetic microstructures configured to generate a first magnetic field spatial distribution within an accessible internal void and a second ferromagnetic microstructure set including one or more ferromagnetic microstructures configured to generate a second magnetic field spatial distribution within an accessible internal void. In an embodiment, the second magnetic field spatial distribution is different from the spatial distribution of the first magnetic field spatial distribution.

In an embodiment, one or more of the ferromagnetic microstructures 102 include a sufficient amount of at least one ferromagnetic material to generate a time-invariant magnetic field 108 within the void 106. In an embodiment, one or more of the ferromagnetic microstructures 102 include a sufficient amount of at least one ferromagnetic material to elicit a magnetic resonance response from a biological sample while the biological sample is received within the void 106. In an embodiment, one or more of the ferromagnetic microstructures 102 include a sufficient amount of at least one ferromagnetic material to affect at least one of an in vivo non-zero spin nuclei transverse magnetic relaxation time (e.g., spin ½ nuclei transverse magnetic relaxation time) or an in vivo non-zero spin nuclei longitudinal magnetic relaxation time (e.g., spin ½ nuclei longitudinal magnetic relaxation time). In an embodiment, one or more of the ferromagnetic microstructures 102 include a sufficient amount of at least one ferromagnetic material to change a magnetic resonance response of a biological sample present within the void 106.

In an embodiment, at least one of the ferromagnetic microstructures 102 is configured to generate a constant magnetic field confined within a volumetric footprint occupied by the ferromagnetic microstructure 102.

In an embodiment, one or more of the ferromagnetic microstructures 102 include a sufficient amount of at least one ferromagnetic material to elicit a substantially homogeneous polarizing magnetic field region within the void 106. In an embodiment, a plurality of ferromagnetic microstructures 102 includes at least a first plurality of ferromagnetic microstructures sized and dimensioned to generate a first magnetic flux density within the void 106 and a second plurality of ferromagnetic microstructures sized and dimensioned to generate a second magnetic flux density within the void 106. In an embodiment, the second magnetic flux density is different from the first magnetic flux density. In an embodiment, a plurality of ferromagnetic microstructures 102 includes at least a first plurality of ferromagnetic microstructures configured to generate a time-invariant magnetic field within the void 106 of a first magnetic field strength and a second plurality of ferromagnetic microstructures configured to generate a time-invariant magnetic field within the void 106 of a second magnetic field strength. In an embodiment, the second magnetic field strength is different from the first magnetic field strength. In an embodiment, a plurality of ferromagnetic microstructures 102 includes at least a first plurality of ferromagnetic microstructures sized and dimensioned to generate a time-invariant magnetic field within the void 106 of a first magnetic field strength and a second plurality of ferromagnetic microstructures sized and dimensioned to generate a time-invariant magnetic field within the void 106 of a second magnetic field strength. In an embodiment, the second magnetic field strength is different from the first magnetic field strength. In an embodiment, at least some of the plurality of ferromagnetic microstructures 102 differ in at least one of a time-invariant magnetic field strength, a number of time-invariant magnetic fields, a void density, an amount of ferromagnetic materials, or a ferromagnetic composition. In an embodiment, a plurality of ferromagnetic microstructures 102 comprise one or more different magnetic field strengths.

In an embodiment, at least one of the ferromagnetic microstructures 102 includes one or more voids 106. In an embodiment, the ferromagnetic microstructures 102 are configured to define one or voids 106 having any geometric form including regular or irregular forms and having a cross-section of substantially any shape including, but not limited to, circular, triangular, square, rectangular polygonal, regular or irregular shapes, or the like, as well as other symmetrical and asymmetrical shapes, or combinations thereof. In an embodiment, a plurality of ferromagnetic microstructures 102 includes at least a first plurality of ferromagnetic microstructures sized and dimensioned to generate at least a first time-invariant magnetic field within the void 106 and a second plurality of ferromagnetic microstructures sized and dimensioned to generate at least a second time-invariant magnetic field within the void 106. In an embodiment, the characteristic magnetic field spatial distribution of the second magnetic field is different from the characteristic magnetic field spatial distribution of the first magnetic field.

The ferromagnetic microstructures 102 may take any geometric form including regular or irregular forms and may have a cross-section of substantially any shape including, but not limited to, circular, triangular, square, rectangular polygonal, regular or irregular shapes, or the like, as well as other symmetrical and asymmetrical shapes, or combinations thereof. In an embodiment, an average major dimension of at least some of the plurality of ferromagnetic microstructures 102 ranges from less than about thousands of micrometers to less than about hundreds of nanometers.

In an embodiment, an average major dimension of at least some of the plurality of ferromagnetic microstructures 102 ranges from about tens of nanometers to about thousands of micrometers. In an embodiment, an average major dimension of at least some of the plurality of ferromagnetic microstructures 102 ranges from less than about hundreds of micrometers to less than about hundreds of nanometers. In an embodiment, an average major dimension of at least some of the plurality of ferromagnetic microstructures 102 ranges from less than about one micrometer to less than about 100 micrometers. In an embodiment, an average major dimension of at least some of the plurality of ferromagnetic microstructures 102 ranges from less than about 100 nanometers to less than about $10^7$ nanometers. In an embodiment, an average major dimension of one or more of the plurality of ferromagnetic microstructures 102 ranges from less than about 1 micrometer to less than about 100 micrometers.

In an embodiment, an average major dimension of at least some of the plurality of ferromagnetic microstructures 102 is in the order of at least one of bacteria (e.g., from about 0.2 µm to about 5 µm), basophils (e.g., from about 12 µm to about 15 µm), endothelial cell (e.g., from about 10 to about 20 µm), eosinophils (e.g., from about 10 µm to about 12 µm), erythrocytes (e.g., from about 6 µm to about 8 µm), lymphocytes (e.g., from about 7 µm to about 8 µm), macrophages (e.g., from about 21 µm), mammalian cells, monocytes (e.g., from about 14 µm to about 17 µm), neutrophils (e.g., from about 10 to about 12 µm), or viruses (e.g., from about $5 \times 10^{-3}$ µm to 0.1 µm) (e.g., from a picornavirus (ranging in size from about 22 nm to about 30 nm) to poxviruses (ranging in size from about 240 nm to about 300 nm). In an embodiment, an average major dimension of at least some of the plurality of ferromagnetic microstructures 102 is at least less than an order of magnitude of about 10 micrometers. In an embodiment, an average particle size distribution of the plurality of ferromagnetic microstructures ranges from about 10 nanometers to about 1 millimeter.

In an embodiment, an average major dimension of at least some of the plurality of ferromagnetic microstructures 102 is less than an order of magnitude of a capillary diameter (e.g., from about 5 to about 10 µm). In an embodiment, an average major dimension of at least some of the plurality of ferromagnetic microstructures 102 is less than an order of magnitude of a space between lateral endothelial cells in blood vessel (e.g., from about 10 to about 20 nm). In an embodiment, an average major dimension of at least some of the plurality of ferromagnetic microstructures 102 is in the order of a quantum dot (e.g., from about 10 to 50 nm). In an embodiment, an average major dimension of at least some of the plurality of ferromagnetic microstructures 102 is in the order of a plasma membrane thickness (e.g., from about 3 to about 10 nm).

An aspect includes systems, devices, and methods employing compositions including, among other things, targeted ferromagnetic microstructures. A non-limiting approach includes systems, devices, methods, and compositions including, among other things, targeted ferromagnetic microstructures. A non-limiting approach includes systems, devices, methods, and compositions for detecting a magnetic resonance event associated with one or more nuclear magnetic resonance detectable nuclei exposed to a static magnetic field within one or more surface-defined voids 106 of a plurality of target-selective microstructures.

In an embodiment, one or more ferromagnetic microstructures 102 of a plurality of ferromagnetic microstructures are configured to selectively interrogate a region of the biological subject. In an embodiment, one or more ferromagnetic microstructures 102 of a plurality of ferromagnetic microstructures are configured to selectively interrogate a tissue of the biological subject. In an embodiment, one or more ferromagnetic microstructures 102 of the a plurality of ferromagnetic microstructures 102 are configured to selectively-target one or more regions of the biological subject.

In an embodiment, at least one of the ferromagnetic microstructures 102 includes one or more targeting moieties 112. For example, one or more of the ferromagnetic microstructures 102 may incorporate one or more targeting moieties 112 that selectively target one or more of the ferromagnetic microstructures 102 to specific tissues, cells, genomic targets, biological targets, or the like. In an embodiment, one or more of the ferromagnetic microstructures 102 may incorporate one or more targeting moieties 112 to target the ferromagnetic microstructures 102 to a target in, on, or outside a cell. In an embodiment, a multiplex method includes a plurality of target-selective microstructures for identifying one or more factors associated with a specific disease state, pathology, or condition by targeting with one or more targeting moieties 112.

Among the one or more targeting moieties 112, examples include, but are not limited to, a cell surface receptor targeting moiety, a transmembrane molecule targeting moiety, an antigen targeting moiety, an immune-receptor targeting moiety, a folate receptor targeting moiety, and the like. Further examples of targeting moieties 112 include, but are not limited to, antibodies or fragments thereof, oligonucleotide or peptide based aptamers, receptors or parts thereof, receptor ligands or parts thereof, lectins, artificial binding substrates formed by molecular imprinting, biomolecules, humanized targeting moieties, mutant or genetically engineered proteins, mutant or genetically engineered protein binding domains, adhesion proteins, e.g., integrins, mucins, fibronectins, and substrates (e.g., poly-lysine, collagen, Matrigel, fibrin) that interact with components of tissues or cells, and the like.

Further examples of targeting moieties 112 include, but are not limited to, an antibody that binds one or more targets on a tissue or cell surface such as, for example, a cell surface receptor, a transmembrane receptor, an immune receptor, as well as biomolecules on, or in close proximity to, a target tissue or cell. Among antibodies or fragments thereof for use as targeting moieties 112, examples include, but are not limited to, monoclonal antibodies, polyclonal antibodies, chimeric antibodies, rabbit antibodies, chicken antibodies, mouse antibodies, human antibodies, humanized antibodies or antibody fragments, Fab fragments of antibodies, F(ab')$_2$ fragments of antibodies, single-chain variable fragments (scFvs) of antibodies, diabody fragments (dimers of scFv fragments), minibody fragments (dimers of scFvs-$C_H$3 with linker amino acid), and the like. Further examples of antibodies or fragments include, but are not limited to, bispecific antibodies, trispecific antibodies, single domain antibodies (e.g., camel and llama VHH domain), lamprey variable lymphocyte receptor proteins, antibodies based on proteins or protein motifs (for example lipocalins, fibronectins, ankyrins and src-homology domains.

Among antibodies, examples include, but are not limited to, immunoglobulin molecules including four polypeptide chains, two heavy (H) chains and two light (L) chains interconnected by disulfide bonds. Each heavy chain includes a heavy chain variable region (VH) and a heavy chain constant region. The heavy chain constant region includes three domains, CH1, CH2 and CH3. Each light chain includes a light chain variable region (VL) and a light chain constant region. The light chain constant region includes one domain, CL. The VH and VL regions can be further subdivided into regions of hypervariability, termed complementarity determining regions (CDRs), interspersed with regions that are more conserved, termed framework regions (FR). Each VH and VL includes three complementarity determining regions and four framework regions, arranged from amino-terminus to carboxy-terminus in the following order: FR1, CDR1, FR2, CDR2, FR3, CDR3, FR4. (See, e.g., U.S. Pat. No. 7,504,485 (issued Mar. 17, 2009), the contents of which are incorporated herein by reference). The pairing of VH and VL together forms a single antigen-binding portion of the antibody.

Among antibody fragments, examples include, but are not limited to, fragments of an antibody that retain the ability to specifically bind to an antigen (e.g., antigen-binding portions). It has been shown that the antigen-binding function of an antibody can be performed by fragments of a full-length antibody. Examples of binding fragments include, but are not limited to single domain antibodies (dAb) fragments (e.g., those including a single VH domain), F(ab')$_2$ fragments (e.g., a bivalent fragment including two Fab fragments linked by a disulfide bridge at the hinge region), Fab fragments (e.g., a monovalent fragment including VL, VH, CL and CH1 domains), Fd fragments (e.g., those including VH and CH1 domains), Fv fragments (e.g., those including VL and VH domains of a single arm of an antibody), single chain Fv (linear fragment containing VH and VL regions separated by a short linker), diabodies (two single chain Fv fragments separated by short linkers), and the like. See e.g., the following documents (the contents of which are incorporated herein by reference): Bird et al., Science 242:423-426 (1988); Ward et al., Nature 341:544-546 (1989); and Huston et al., Proc. Natl. Acad. Sci. USA 85:5879-5883 (1988).

Examples of diabodies include, but are not limited to, bivalent, bispecific antibodies having VH and VL domains expressed on a single polypeptide chain, but using a linker that is too short to allow for pairing between the two domains on the same chain (thereby forcing the domains to pair with complementary domains of another chain and creating two antigen binding sites). See e.g., the following documents (the contents of which are incorporated herein by reference): Holliger, P., et al., Proc. Natl. Acad. Sci. USA 90:6444-6448 (1993); Poljak, R. J., et al., Structure 2:1121-1123 (1994).

Alternatively, an antibody or antigen-binding portion thereof may be part of a larger immunoadhesion molecule, formed by covalent or non-covalent association of the antibody or antibody portion with one or more other proteins or peptides. See e.g., the following documents (the contents of which are incorporated herein by reference): Kipriyanov, S. M., et al., Human Antibodies and Hybridomas 6:93-101 (1995) and Kipriyanov, S. M., et al., Mol. Immunol. 31:1047-1058 (1994).

Antibody portions, such as Fab and F(ab')$_2$ fragments, are prepared from whole antibodies using conventional techniques, such as papain or pepsin digestion, respectively, of whole antibodies. Antibodies, antibody portions and immunoadhesion molecules, and the like can be obtained using standard recombinant DNA techniques.

In an embodiment, one or more of the targeting moieties 112 include single chain or multiple chain antigen-recognition motifs, epitopes, or mimotopes. In an embodiment, the multiple chain antigen-recognition motifs, epitopes, or mimotopes can be fused or unfused. Among antibodies or fragments thereof, examples include, but are not limited to, antibodies or fragments thereof generated using, for example, standard methods such as those described by Harlow & Lane (*Antibodies: A Laboratory Manual*, Cold Spring Harbor Laboratory Press; 1$^{st}$ edition 1988) (the contents of which are incorporated herein by reference). In an embodiment, an antibody or fragment thereof may be generated using phage display technology. See, e.g., Kupper, et al. *BMC Biotechnology* 5:4 (2005) (the contents of which are incorporated herein by reference). An antibody or fragment thereof could also be prepared using, for example, in silico design. See, e.g., Knappik et al., *J. Mol. Biol.* 296: 57-86 (2000) (the contents of which are incorporated herein by reference).

In an embodiment, at least one targeting moiety 112 associated with a ferromagnetic microstructure 102 is a diagnostic or therapeutic antibody or antibody fragment approved for use in humans by the U.S. Food and Drug Administration (FDA). Examples of FDA approved antibodies include, but are not limited to, abciximab, adalimumab, alemtuzumab, arcitumomab, basiliximab, bevacizumab, capromab pendetide, cetuximab, daclizumab, efalizumab, gemtuzumab, ibritumomab tiuxetan, infliximab, muromonab-CD3, nimotuzumab, nofetumomab, omalizumab, palivizumab, rituximab, tocilizumab, tositumomab, trastuzumab, and the like. Examples of other diagnostic or therapeutic antibodies include adecatumumab, apolizumab, bavituximab, belimumab, cixutumumab, conatumumab, denosumab, edrecolomab, epratuzumab, etaracizumab, farletuzumab, figitumumab, gantenerumab, golimumab, iratumumab, lerdelimumab, lexatumumab, lintuzumab, lucatumumab, mapatumumab, metelimumab, necitumumab, ofatumumab, panitumumab, pritumumab, robatumumab, stamulumab, votumumab, zalutumumab, zanolimumab, and the like.

In an embodiment, one or more ferromagnetic microstructures 102 include at least one targeting moiety 112 directed to gene expression products. For example, in an embodiment, a targeting moiety 112 may specifically target a gene, an mRNA, a microRNA, a gene product, a protein, a glycosylation of a gene product, a substrate or metabolite of a gene product, or the like. See, e.g., U.S. Patent Publ. No. 2008-0206152 (published Aug. 28, 2008) (the contents of which are incorporated herein by reference). In an embodiment, one or more targeting moieties 112 are configured to target a compound directly associated with gene expression (e.g., transcription factors, acetylated histones, zinc finger proteins, translation factors, a metabolite of an enzyme, or the like).

In an embodiment, one or more of the targeting moieties 112 are configured to target an in vivo component in, on, or outside a cell. Among in vivo targets, examples include, but are not limited to, carbohydrates, cell surface proteins (e.g., cell adhesion molecules, cell surface polypeptides, membrane receptors, or the like), cytosolic proteins, intracellular components (e.g., one or more components of a signaling cascade such as, for example, one or more signaling molecules, kinases, phosphatases, transcription factors, signaling peptides, signaling proteins, or the like), metabolites, nuclear proteins, receptors, and secreted proteins (e.g., growth factors, cell signaling molecules, or the like).

In an embodiment, one or more of the targeting moieties 112 include at least one NANOBODY (e.g., single domain antibodies, single-chain antibody fragments (VHH), NANOBODIES (Ablynx nv Belgium), or the like, or fragments thereof). VHHs have been developed against various tissue and cell targets, examples of which include lipopolysaccharide (sepsis), carcinoembryonic antigen (CEA; cancer), and the epidermal growth factor receptor (cancer) (see, e.g., Harmsen, et al., *Appl. Microbiol. Biotechnol.* 77:31-22 (2007), the contents of which are incorporated herein by reference). In an embodiment, one or more of the targeting moieties 112 include at least one heavy chain, single N-terminal domain antibody that does not require domain pairing for antigen recognition.

In an embodiment, one or more of the targeting moieties 112 include at least one oligonucleotide RNA or DNA based aptamer. Aptamers are oligonucleotides (DNA or RNA) that can bind to a wide variety of entities (e.g., metal ions, small organic molecules, proteins, or cells) with high selectivity, specificity, and affinity. Aptamers may be isolated from a large library of about $10^{14}$ to about $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374 (2005); Jayasena *Clin. Chem.* 45:1628-1650 (1999); (the contents of which are incorporated herein by reference). Or an aptamer may be synthetically created and screened or its sequence devised in silico. In an embodiment, an aptamer library is screened against one or more targets of interest. For example, an RNA aptamer may be generated against leukemia cells using a cell based SELEX method. See, e.g., Shangguan, et al., *Proc. Natl. Acad. Sci. USA* 103: 11838-11843 (2006) (the contents of which are incorporated herein by reference). Similarly, an aptamer that recognizes bacteria may be generated using the SELEX method against whole bacteria. See, e.g., Chen, et al., *Biochem. Biophys. Res. Commun.* 357:743-748 (2007) (the contents of which are incorporated herein by reference). In an embodiment, one or more of the targeting moieties 112 include at least one peptide based aptamer. Among peptide based aptamers, examples include, but are not limited to, an artificial protein where inserted peptides are expressed as part of a primary sequence of a structurally stable protein or scaffold. See, e.g., Crawford et al., *Peptide Aptamers: Tools for Biology and Drug Discovery*, Briefings in Functional Genomics and Proteomics, 2 (1): 72-79 (2003) (the contents of which are incorporated herein by reference).

In an embodiment, one or more of the targeting moieties 112 include all or part of a naturally occurring ligand that binds to, for example, a receptor on a surface of tissue or cells of interest. In an embodiment, one or more of the targeting moieties 112 include all or part of a peptide hormone, examples of which include, but are not limited to, neuropeptides, (e.g., enkephalins, neuropeptide Y, somatostatin, corticotropin-releasing hormone, gonadotropin-releasing hormone, adrenocorticotropic hormone, melanocyte-stimulating hormones, bradykinins, tachykinins, cholecystokinin, vasoactive intestinal peptide (VIP), substance P, neurotensin, vasopressin, calcitonin, or the like); cytokines (e.g., interleukins (e.g., IL-1 through IL-35), erythropoietin, thrombopoietin, interferon (IFN), granulocyte monocyte colony-stimulating factor (GM-CSF), tumor necrosis factor (TNF), or the like); chemokines (e.g., RANTES, TARC, MIP-1, MCP, or the like); growth factors (e.g., platelet derived growth factor (PDGF), transforming growth factor beta (TGFβ), nerve growth factor (NGF), epidermal growth factor (EGF), insulin-like growth factor (IGF), basic fibroblast growth factor (bFGF), vascular endothelial growth factor (VEGF), or the like); other peptide hormones (e.g., atrial natriuretic factor, insulin, glucagon, angiotensin, prolactin, oxyocin, or the like), and the like.

Other examples of peptides that could be used as targeting moieties 112 include, but are not limited to, those found in venomous snakes, insects, or plants. For example, chlorotoxin (CTX), a 36 amino acid peptide isolated from the deathstalker scorpion (*Leiurus quinquestriatus*), binds preferentially to glioma cells relative to normal glial cells and other cells of the central nervous system (Soroceanu, et al., *Cancer Res.* 58:4871-4879 (1998), the contents of which are incorporated herein by reference). Examples of other peptide toxins include, but are not limited to, botulinum toxin, agatoxin, charybdotoxin, conotoxin, dendrotoxin, iberiotoxin, kaliotoxin, and tityustoxin. These peptide toxins preferentially interact with membrane associated calcium, sodium, chloride or potassium channels and as such, may be used as targeting moieties 112 to target, for example, ion channels.

In an embodiment, one or more of the targeting moieties 112 include an "universal cell-recognition site" binding tripeptide arginine-glycine-aspartic acid (RGD) or analogs thereof. RGD and RGD analogs preferentially interact with members of the transmembrane spanning integrin gene family and may be used to target integrins associated with diseased states. For example, the RGD peptide may be used as a targeting moiety to target tumor cells expressing increased levels of the integrin $alpha_v$-$beta_3$ (Liu, et. al., *ACS Nano* 1:50-56 (2007), the contents of which are incorporated herein by reference).

In an embodiment, one or more of the targeting moieties 112 include one or more novel ligands identified using a peptide phage library. See, e.g., Bonetto, et al., *FASEB J.* 23:575-585 (2009) (the contents of which are incorporated herein by reference). In an embodiment, phage are engineered to express a library of novel peptides on their surface as fusion proteins in association with a phage major or minor coat protein. The peptide phage library can be screened against cultured transformed cells lines such as, for example, U87-MG human malignant glioma cells or against primary tumors from patients with various cancers such as, for example, breast and pancreatic cancer and melanoma (see, e.g., Spear, et al. *Cancer Gene Therapy* 8:506-511 (2001); Krag, et al. *Cancer Res.* 66:7724-7733 (2006). In an embodiment, a cancer targeting ligand may be identified by screening a random peptide library against a cancer target using a yeast two-hybrid screen. See, e.g., Nauenburg, et al. *FASEB J.* 15:592-594 (2001).

In an embodiment, one or more of the targeting moieties 112 include one or more small chemical compound ligands that interact with a cognate on a target cell, such as a receptor. Examples of small chemical compound ligands include, but are not limited to, acetylcholine, adenosine triphosphate (ATP), adenosine, androgens, dopamine, endocannabinoids, epinephrine, folic acid, gamma-aminobutyric acid (GABA), glucocorticoids, glutamate, histamine, leukotrienes, mineralocorticoids, norepinephrine, prostaglandins, serotonin, thromoxanes, and vitamins. In an embodiment, one or more of the ferromagnetic microstructures 102 are modified with folic acid, such that the modified microstructures maybe targeted to folate receptors overexpressed on some tumor cells. See, e.g., Kranz et al., *Proc. Natl. Acad. Sci.* USA 92:9057-9061 (1995) (the contents of which are incorporated herein by reference).

In an embodiment, one or more of the targeting moieties 112 include one or more synthetic small molecule compounds such as an agonist or antagonist that interact with a target on, or in proximity to, a cell or tissue. Among agonists, antagonists, or other small molecule compounds, examples include, but are not limited to, those approved by the U.S. Food and Drug Administration (FDA) for use in humans such as, for example, those listed in *Remington: The Science and Practice of Pharmacy*, 21st Edition, 2005, edited by David Troy, Lippincott Williams & Wilkins, Baltimore Md. In an embodiment, at least one of the ferromagnetic microstructures 102 is conjugated to a leukotriene B4 receptor antagonist for use, for example, as MRI contrast agents for detection of infection and inflammation. See, e.g., U.S. Patent Pub No. 2008/0213181 (published Sep. 4, 2008) (the contents of which are incorporated herein by reference).

In an embodiment, one or more of the targeting moieties 112 include one or more lectins. Among lectins, examples include, but are not limited to, agglutinins that could discriminate among types of red blood cells and cause agglutination, sugar-binding proteins from many sources regardless of their ability to agglutinate cells, and the like. Lectins have been found in plants, viruses, microorganisms and animals. Because of the specificity that each lectin has toward a particular carbohydrate structure, even oligosaccharides with identical sugar compositions may be distinguished or separated. Some lectins will bind only to structures with mannose or glucose residues, while others may recognize only galactose residues. Some lectins require that a particular sugar be in a terminal non-reducing position in the oligosaccharide, while others can bind to sugars within the oligosaccharide chain. Some lectins do not discriminate between a and b anomers, while others require not only the correct anomeric structure but also a specific sequence of sugars for binding.

Further examples of lectins include, but are not limited to, algal lectins (e.g., b-prism lectin); animal lectins (e.g., tachylectin-2, C-type lectins, C-type lectin-like, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1); bacterial lectins (e.g., *Pseudomonas* PA-IL, *Burkholderia lectins*, *chromobacterium* CV-IIL, *Pseudomonas* PA IIL, *Ralsonia* RS-ILL, ADP-ribosylating toxin, *Ralstonia* lectin, *Clostridium* hemagglutinin, botulinum toxin, tetanus toxin, cyanobacterial lectins, FimH, GafD, PapG, Staphylococcal enterotoxin B, toxin SSL11, toxin SSL5); fungal and yeast lectins (e.g., *Aleuria aurantia* lectin, integrin-like lectin, *Agaricus* lectin, *Sclerotium* lectin, *Xerocomus* lectin, *Laetiporus* lectin, *Marasmius oreades* agglutinin, *agrocybe* galectin, *coprinus* galectin-2, Ig-like lectins, L-type lectins); plant lectins (e.g., alpha-D-mannose-specific plant lectins, *amaranthus* antimicrobial peptide, hevein, pokeweed lectin, *Urtica dioica* UD, wheat germ WGA-1, WGA-2, WGA-3, artocarpin, artocarpus hirsute AHL, banana lectin, Calsepa, heltuba, jacalin, Maclura pomifera MPA, MornigaM, Parkia lectins, abrin-a, abrus agglutinin, amaranthin, castor bean ricin B, ebulin, mistletoe lectin, TKL-1, cyanovirin-N homolog, and various legume lectins); and viral lectins (e.g., capsid protein, coat protein, fiber knob, hemagglutinin, and tailspike protein) (see, e.g., E. Bettler, R. Loris, A. Imberty 3*D-Lectin database: A web site for images and structural information on lectins*, 3rd Electronic Glycoscience Conference, The internet and World Wide Web, 6-17 Oct. 1997; http://www.cermav.cnrs.fr/lectines/).

In an embodiment, one or more of the targeting moieties 112 include one or more synthetic elements such as an artificial antibody or other mimetic. Examples of synthetic elements may be found in, for example, the following documents (the contents of which are incorporated herein by reference): U.S. Pat. Nos. 5,804,563 (issued Sep. 8, 1998); 5,831,012 (issued Nov. 3, 1998); 6,255,461 (issued Jul. 3, 2001); 6,670,427 (issued Dec. 30, 2003); 6,797,522 (issued Sep. 28, 2004); U.S. Patent Pub. No. 2004/0018508 (published Jan. 29, 2004); Ye and Haupt, *Anal Bioanal Chem.* 378: 1887-1897 (2004); and Peppas and Huang, *Pharm Res.* 19: 578-587 (2002).

In an embodiment, antibodies, recognition elements, or synthetic molecules that recognize a cognate may be available from a commercial source. See, e.g., Affibody® affinity ligands (Abcam, Inc. Cambridge, Mass. 02139-1517; U.S. Pat. No. 5,831,012 (issued Nov. 3, 1998), the contents of which are incorporated herein by reference).

In an embodiment, one or more of the targeting moieties 112 include one or more artificial binding substrates formed by, for example, molecular imprinting techniques and methodologies. A more detailed discussion of molecular imprinting can be found in, for example, the following documents (the contents of which are incorporated herein by reference): U.S. Pat. Nos. 7,442,754 (issued Oct. 28, 2008), 7,288,415 (issued Oct. 30, 2007), 6,660,176 (issued Dec. 9, 2003), and 5,801,221 (issued Sep. 1, 1998). In an embodiment, a target template is combined with functional monomers which, upon cross-linking, forms a polymer matrix that surrounds the target template. Removal of the target template leaves a stable cavity in the polymer matrix that is complementary in size and shape to the target template. As such, functional monomers of a polymer forming matrix such as acrylamide and ethylene glycol dimethacrylate, for example, can be mixed with one or more cytokine in the presence of a photoinitiator such as 2,2-azobis(isobutyronitrile). The monomers can be cross-linked to one another using ultraviolet irradiation. The resulting polymer may be crushed or ground into smaller pieces and washed to remove the one or more cytokine, leaving a particulate matrix material capable of binding one or more cytokine. Examples of other functional monomers, cross-linkers and initiators useful to generate an artificial binding substrate have been described elsewhere (see, e.g., U.S. Pat. No. 7,319,038 (issued Jan. 15, 2008) (the contents of which are incorporated herein by reference).

In an embodiment, one or more of the targeting moieties 112 are configured to target RNA or DNA. Examples of targeting moieties 112 that bind RNA or DNA include, but are not limited to, microRNA, anti-sense RNA, small interfering RNA (siRNA), anti-sense oligonucleotides, protein-nucleic acids (PNAs). For example, Bartlett et al., describe modifying $^{64}$Cu-labeled nanoparticles with a specific siRNA for use in tumor localization by positron emission tomography (Bartlett et al., *Proc. Natl. Acad. Sci., USA*. 104:15549-15554 (2007), the contents of which are incorporated herein by reference). Similarly, Yezhelyev, et al., describe siRNA linked to proton-sponge-coated quantum dots for intracellular imaging (Yezhelyev, et al., *J. Am. Chem. Soc.* 130:9006-9012 (2008), the contents of which are incorporated herein by reference).

Referring to FIGS. 1C, 1D, and 1E, in an embodiment, at least a first internal surface 104 of at least one of the plurality of ferromagnetic microstructures 102 includes one or more targeting moieties 112. In an embodiment, at least an outer surface 110 of at least one of the plurality of ferromagnetic microstructures 102 includes one or more targeting moieties 112. In an embodiment, a majority of the one or more targeting moieties 112 is localize to a portion of the void 106 including a time-invariant magnetic field 108.

In an embodiment, at least one of the plurality of ferromagnetic microstructures 102 includes one or more targeting moieties 112a attached to at least a first internal surface 104. In an embodiment, at least one of the plurality of ferromagnetic microstructures 102 includes one or more targeting moieties 112b attached to an outer surface 110. In an embodiment, at least one of the plurality of ferromagnetic microstructures 102 includes one or more targeting moieties 112a attached to at least a first internal surface 104 and one or more targeting moieties 112b attached to an outer surface 110. In an embodiment, the one or more targeting moieties 112a attached to the first internal surface 104 differ from the one or more targeting moieties 112b attached to the outer surface 110.

In an embodiment, a plurality of ferromagnetic microstructures 102 include two or more different targeting moieties 112. In an embodiment, a plurality of ferromagnetic microstructures 102 include one or more targeting moieties on an outer surface 110 and one or more targeting moieties 112 on an inner surface 104. In an embodiment, the one or more targeting moieties 112 on the outer surface 110 differ from the one or more targeting moieties 112 on the inner surface 104. In an embodiment, the one or more targeting moieties 112 on the outer surface 110 differ in at least one of a target 122a, a cell-receptor target 122b, a target selectivity, or a target specificity from the one or more targeting moieties 112 on the inner surface 104.

In an embodiment, one or more of the targeting moieties 112 may interact with or bind to one or more targets on or proximal to a tissue, cell surface, or the like such as, for example, a cell surface receptor, a transmembrane receptor, immune receptor, or components thereof. In an embodiment, one or more of the targeting moieties 112 may interact with components of vascular circulation system including cells, biomolecules, and infecting pathogens. In an embodiment, the target tissue or target cell includes a tumor cell or other diseased cell type in a mammalian subject. Further examples of target cells include, but are not limited to, one or more pathogens (e.g., virus, bacteria, fungi, or parasite). In an embodiment, the ferromagnetic microstructures 102 are configured to enter a cell and target a specific cellular organelle (e.g., the mitochondria). Among targets associated with a target cell or organelle, examples include, but not limited to, at least one of a protein, a carbohydrate, a glycoprotein, a glycolipid, a sphingolipid, a glycerolipid, or metabolites thereof.

In an embodiment, at least one of the ferromagnetic microstructures 102 can include one or more targeting moieties 112 that bind to or interact with one or more targets associated with or released by a specific tissue or cell type. Among the one or more targets, examples include, but are not limited to, those associated with endothelial cells (e.g., VE cadherin, VonWillibrand Factor, thrombomodulin, angiotension-converting enzyme, or the like), epithelial cells (e.g., cytokeratins, mucins, specific sodium channels, surfactant proteins, or the like), neurons, glial cells or astrocytes (e.g., artemin, BDNF, glial filament protein, nerve growth factor receptor, neuron specific enolase, neurofascin, peripherin, myelin basic protein, NMDA receptor, neurofilament, neuropilins, or the like), or smooth muscle cells (e.g., smooth muscle actin, cyclic nucleotide phosphodiesterase type 5, or the like). One or more of the targeting moieties 112 may bind to any of a number of markers specific for circulating inflammatory cells, for example, T-lymphocytes (e.g., CD3, CD4, CD8), B-lymphocytes (e.g., CD20), monocytes (e.g., LFA-1 alpha, CD163), or granulocytes (e.g., CD66, CD67). In an embodiment, one or more of the targeting moieties 112 may target a specific organ. For example, galactosylated chitosan may be used to specifically target the liver (Kim, et al., *J. Nucl. Med.* 46:141-145, (2005), the contents of which are incorporated herein by reference). In an embodiment, the targeting moiety 112 may target a specific pathology. For example, targeting moieties directed to the mannose-6-phosphate receptor may be used to visualize fibrosis (see, e.g., U.S. Patent Pub. No. 2008/0279765 (published Nov. 13, 2008), the contents of which are incorporated herein by reference).

In an embodiment, one or more of the ferromagnetic microstructures 102 include one or more targeting moieties 112 that bind one or more targets associated with or released by a tumor cell. Examples of targets associated with tumor cells include, but are not limited to, androgen receptor (androgen responsive prostate cancer), BLyS receptor, carcinoembryonic antigen (CEA), CA-125, CA19-9, CD25, CD34, CD33 and CD123 (acute myeloid leukemia), CD20 (chronic lymphocytic leukemia), CD19 and CD22 (acute lymphoblastic leukemia), CD44v6 (epithelial-derived tumors), CD30, CD40, CD70, CD133, 57 kD cytokeratin, epithelial specific antigen, extracellular matrix glycoprotein tenascin, Fas/CD95, gastrin-releasing peptide-like receptors, hepatocyte specific antigen, HER2 receptor, human gastric mucin, human milk fat globule, lymphatic endothelial cell marker, matrix metalloproteinase 9, melan A, melanoma marker, melanocortin-1 receptor, mesothelin, mucin glycoproteins (e.g., MUC1, MUC2, MUC4, MUC5AC, MUC6), prostate specific antigen (PSA), prostate specific membrane antigen (PSMA), prostatic acid phosphatase, PTEN, renal cell carcinoma marker, RGD-peptide binding integrins (e.g., alpha5beta3, alpha5beta6), survivin, sialyl Lewis A, six-transmembrane epithelial antigen of the prostate (STEAP), TAG-72 (colon cancer), TNF receptor, TRAIL receptor, tyrosinase, villin. Other tumor associated antigens include, but are not limited to, alpha fetoprotein, apolipoprotein D, clusterin, chromogranin A, myeloperoxidase, MyoD1 myoglobin placental alkaline phosphatase c-fos, homeobox genes, and the like. In an embodiment, the target may be a cell surface receptor or cell surface marker on a tumor cell. In an embodiment, the target may be a biomolecule secreted by a tumor cell.

In an embodiment, one or more of the ferromagnetic microstructures 102 include one or more targeting moieties 112 that interact with a target that is associated with an immune or inflammatory response. In an embodiment, one or more of the targeting moieties 112 include one or more immune receptors. Examples of immune receptors include, but are not limited to, cytokine receptors (e.g., erythropoietin receptor, GM-CSF receptor, G-CSF receptor, growth hormone receptor, oncostatin M receptor, leukemia inhibitory factor receptor, interleukin receptors, interferon-alpha/beta receptors, interferon-gamma receptor, CSF1, c-kit receptor, interleukin-18 receptor, tumor necrosis factor (TNF) receptor family, lymphotoxin beta receptor, chemokine receptors such as interleukin-8 receptor, CCR1, CXCR4, and TGF beta receptors), Fc receptors (e.g., Fc-epsilon RI, Fc-epsilon RII, Fc-gamma RI, Fc-gamma RII, Fc-gamma RIII, Fc-alpha RI, and Fc-alpha/mu R), lymphocyte homing receptors (e.g., CD44, L-selectin, VLA-4, and LFA-1), pattern recognition/toll-like receptors (e.g., TLR1 through TLR10), T-cell receptors, B-cell receptors, major histocompatibility complex (MHC), complement, immunophilins, integrin, killer-cell immunoglobulin-like receptors, and the like. A more extensive description of inflammatory mediator receptors can be found in, for example, Ozaki and Leonard, *J. Biol. Chem.* 277:29355-29358 (2002) (the contents of which are incorporated herein by reference).

In an embodiment, one or more of the ferromagnetic microstructures 102 include one or more targeting moieties 112 that interact with specific biomolecules in the plasma of the vascular circulation such as, for example, soluble inflammatory mediators. Examples of soluble inflammatory mediators include, but are not limited to, cytokines such as interferons, interleukins, tumor necrosis factor (TNF), granulocyte colony stimulating factor (G-CSF), granulocyte-macrophage colony stimulating factor (GM-CSF), macrophage colony-stimulating factor (M-CSF), erythropoietin (EPO) and thrombopoietin (TPO), and chemokines. Other examples of inflammatory mediators include, but are not limited to, leukotrienes, prostaglandins, growth factors, soluble receptors, C-reactive protein, CD11b, histamine, serotonin, apolipoprotein A1, bradykinin, endothelin-1, eotaxin, insulin, IP-10, leptin, lymphotactin, OSM, SGOT TIMP-1, tissue factor, VCAM-1, VWF, thromboxane, platelet activating factor (PAF), pathogen-derived endotoxins and exotoxins, and the like.

In an embodiment, one or more of the ferromagnetic microstructures 102 include one or more targeting moieties 112 that interact with other specific biomolecules in the plasma of the vascular circulation system including. Among, biomolecules in the plasma of the vascular circulation system, examples include, but not limited to, albumin and pre-albumin, immunoglobulins, lipoproteins, complement components, alpha-globulins, beta-globulins, retinol binding protein, and coagulation proteins.

In an embodiment, one or more of the ferromagnetic microstructures 102 include one or more targeting moieties 112 that bind one or more targets that are transmembrane receptors. Examples of transmembrane receptors include, but are not limited to, G protein-coupled receptors (e.g., muscarinic acetylcholine receptor, adenosine receptor, adrenergic receptors, GABA receptors, angiotensin receptors, cannabinoid receptors, cholecystokinin receptors, dopamine receptors, glucagon receptors, glutamate receptors, histamine receptors, olfactory receptors, opioid receptors, rhodopsin, secretin receptors, serotonin receptors, somatostatin receptors, calcium-sensing receptors, chemokine receptors, or the like); receptor tyrosine kinases (e.g., erythropoietin receptor, insulin receptors, epidermal growth factor (EGF) receptors, platelet-derived growth factor (PDGF) receptors, fibroblast growth factor (FGF) receptors, vascular endothelial growth factor (VEGF) receptors, and Trk receptors, or the like); guanylyl cyclase receptors; ion channels; folate receptors; and the like.

In an embodiment, one or more of a plurality of ferromagnetic microstructures 102 include one or more targeting moieties 112 attached to at least one of the plurality of ferromagnetic microstructures 102. In an embodiment, one or more of the targeting moieties 112 include at least one cell surface receptor-targeting moiety. In an embodiment, one or more of the targeting moieties 112 include at least one transmembrane receptor-targeting moiety. In an embodiment, one or more of the targeting moieties 112 include at least one antigen-targeting moiety. In an embodiment, one or more of the targeting moieties 112 include at least one immune-receptor targeting moiety. In an embodiment, one or more of the targeting moieties 112 include at least one folate receptor targeting moiety. In an embodiment, one or more of the targeting moieties 112 include at least one nucleotide binding moiety. In an embodiment, one or more of the targeting moieties 112 include at least one oligodeoxyribonucleotide binding moiety. In an embodiment, one or more of the targeting moieties 112 include at least one oligoribonucleotide binding moiety. In an embodiment, one or more of the targeting moieties 112 include at least one peptide nucleic acid. In an embodiment, one or more of the targeting moieties 112 include at least one aptamer. In an embodiment, one or more of the targeting moieties 112 include at least one antibody or antibody fragment.

In an embodiment, one or more of the targeting moieties 112 include at least one amyloid binding moiety. In an embodiment, one or more of the targeting moieties 112 include at least one β-amyloid binding moiety. In an embodiment, one or more of the targeting moieties 112 include at least one thioflavin derivative. In an embodiment, the one or more targeting moieties 112 include at least one 2-[4'-(methylamino)phenyl]benzothiazole derivative. In an embodiment, one or more of the targeting moieties 112 include at least one 2-aryl benzothiazole derivative. In an embodiment, one or more of the targeting moieties 112 include at least one Congo red derivative. In an embodiment, one or more of the targeting moieties 112 include [(trans,trans)-1-bromo-2,5-bis-(3-hydroxycarbonyl-4-hydroxy)styrylbenzene.

In an embodiment, a plurality of ferromagnetic microstructures 102 includes two or more ferromagnetic microstructure sets. In an embodiment, at least one of the two or more ferromagnetic microstructure sets includes a different targeting moiety 112 from another of the two or more ferromagnetic microstructure sets. In an embodiment, at least one of the two or more ferromagnetic microstructure sets includes a different targeting moiety 112 configuration from another of the two or more ferromagnetic microstructure sets 102.

In an embodiment, one or more of the ferromagnetic microstructures 102 are configured to bind or interact with one or more targets within the cell. In an embodiment, one or more of the ferromagnetic microstructures 102 are configured to enter into the cytoplasm of a cell.

In an embodiment, one or more of the ferromagnetic microstructures 102 include one or more targeting moieties 112 that bind or interact with one or more intracellular targets. Examples of intracellular targets include, but are not limited to, protein targets, lipid targets, oligonucleotide targets, and the like. Examples of intracellular proteins include, but are not limited to, enzymes (e.g., oxidoreductases, transferases, hydrolases, lysases, isomerases, ligases), structural proteins (e.g., myosin, tubulin, intermediate filaments, and actin), and the like. Examples of intralellular RNAs include, but are not limited to, messenger RNA, transfer RNA, ribosomal RNA, small nuclear RNA, small interfering RNA, microRNA, and the like.

In an embodiment, one or more of a plurality of ferromagnetic microstructures 102 include one or more targeting moieties 112 directed at a genomic target. In an embodiment, one or more of a plurality of ferromagnetic microstructures 102 include one or more genomic targeting moieties. In an embodiment, one or more of the ferromagnetic microstructures 102 are configured to selectively-target one or more genomic targets. In an embodiment, the one or more genomic targets include at least one deoxyribonucleic acid sequence. In an embodiment, the one or more genomic targets include at least one ribonucleic acid sequence. In an embodiment, the one or more genomic targets include at least one oncogene. In an embodiment, the one or more genomic targets include at least one chromosome translocation. In an embodiment, the one or more genomic targets include at least one methylated deoxyribonucleic acid sequence. In an embodiment, the one or more genomic targets include at least one methylated deoxyribonucleic acid sequence including a methylated cytosine. In an embodiment, the one or more genomic targets include at least one methylated ribonucleic acid sequence. In an embodiment, the one or more genomic targets include at least one deoxyribonucleic acid sequence including unmethylated cytosine.

In an embodiment, the one or more genomic targets include at least one single-nucleotide polymorphism. In an embodiment, the one or more genomic targets include at least one of a somatic mutation, germline mutation, chemically induced mutation, biologically induce mutation, or an environmentally induce mutation. In an embodiment, the one or more genomic targets include at least one double stranded deoxyribonucleic acid sequence. In an embodiment, the one or more genomic targets include at least one single stranded deoxyribonucleic acid sequence. In an embodiment, the one or more genomic targets include at least one mitochondrial deoxyribonucleic acid sequence. In an embodiment, the one or more genomic targets include at least one of a point mutation, an insertion of one or more nucleotides, or a deletion of one or more nucleotides. In an embodiment, one or more of the ferromagnetic microstructures 102 include one or more antigen epitope targeting moieties. In an embodiment, one or more of the ferromagnetic microstructures 102 include one or more antigen mimotopes targeting moieties. In an embodiment, one or more of the ferromagnetic microstructures 102 include at least one single chain or a multiple chain antigen-recognition motif.

In an embodiment, one or more of a plurality of ferromagnetic microstructures 102 include one or more targeting moieties 112 that target zinc finger-including proteins. In an embodiment, one or more of the ferromagnetic microstructures 102 one or more include targeting moieties that target a zinc finger-including protein. In an embodiment, one or more of the ferromagnetic microstructures 102 include one or more proteins associated with a zinc finger motif, the one or more proteins configured to bind a deoxyribonucleic acid sequence target. In an embodiment, one or more of the ferromagnetic microstructures 102 include one or more proteins associated with a zinc finger motif, the one or more proteins configured to bind a ribonucleic acid sequence target. In an embodiment, one or more of the ferromagnetic microstructures 102 include one or more proteins associated with a zinc finger motif, the one or more proteins configured to target a deoxyribonucleic acid sequence target. In an embodiment, one or more of the ferromagnetic microstructures 102 include one or more proteins associated with a zinc finger motif, the one or more proteins configured to target a ribonucleic acid sequence target. In an embodiment, one or more of a plurality of ferromagnetic microstructures 102 include one or more targeting moieties that target nucleic acid sequences in vivo. For example zinc finger domain-including proteins can be used to target specific DNA or RNA sequences. Examples of engineered and selected zinc finger domain-including proteins targeting promoter sequences or 5' untranslated regions of specific genes by binding in the major groove of double stranded DNA are described in Blancafort et al, Combinatorial Chemistry High Throughput Screening, vol. 11, pp. 146-158 (2008) and Moore et al, Briefings In Funct. Genom. Proteom., vol. 1, pp. 342-355 (2003) which are incorporated by reference herein. In an embodiment, one or more of a plurality of ferromagnetic microstructures 102 include one or more targeting moieties 112 that target human chromosomes in vivo. In an embodiment, one or more of the ferromagnetic microstructures 102 include one or more targeting moieties that target at least a portion of a human chromosome in vivo.

One or more of the systems, devices, methods, and composition described herein can be used alone or in combination with other diagnostic imaging techniques and methodologies such as, for example, x-ray imaging, computed tomography (CT), ultrasound, magnetic resonance imaging (MRI), positron emission tomography (PET), single photon emission computed tomography (SPECT), gamma camera imaging, fluorescence tomography, or the like.

In a non-limiting approach, systems, devices, methods, and composition described herein can include, among other things, one or more contrast agents for use in one or more diagnostic imaging technique. A non-limiting approach includes imaging systems, devices, methods, and compositions including, among other things, targeted ferromagnetic microstructures and one or more imaging contrast agents.

For example, in an embodiment, a composition including ferromagnetic microstructures 102 may incorporate at least one of contrast agents, radiopaques, or roentgenographic drugs for use in one or more diagnostic imaging technique. A non-limiting approach includes systems, devices, methods, and compositions including, among other things, one or more imaging probes.

An aspect includes systems, devices, methods, and compositions including, among other things, one or more imaging probes attached to one or more of the plurality of ferromagnetic microstructures 102. A non-limiting approach includes systems, devices, methods, and compositions including, among other things, one or more magnetic resonance imaging contrast agents. In an embodiment, the one or more imaging probes include at least one fluorescent agent. In an embodiment, the one or more imaging probes include at least one quantum dot. In an embodiment, the one or more imaging probes include at least one radio-frequency identification transponder. In an embodiment, the one or more imaging probes include at least one x-ray contrast agent. In an embodiment, the one or more imaging probes include at least one molecular imaging probe. A non-limiting approach includes systems, devices, methods, and compositions including, among other things, one or more contrast agents. Among imaging probes, examples include, but are not limited to, fluorescent agents, molecular imaging probes, quantum dots, radio-frequency identification transponders (RFIDs), x-ray contrast agents, and the like.

Among contrast agents, radiopaques, or roentgenographic drugs used for diagnostic x-ray imaging and computed tomography (CT), examples include, but are not limited to, barium sulfate and various iodine derivatives including diatrizoate meglumine, diatrizoate sodium, iodipamide meglumine, diatrizoic acid, ethiodized oil, iodipamide, iodixanol, iohexyl, iomeprol, iopamidol, iopanoic acid, iophendylate, iopromide, iothalamate meglumine, iothalamate sodium, iothalamic acid, ioversol, ioxaglate meglumaine, ioxaglate sodium, and the like.

Among contrast agents used for diagnostic ultrasound imaging, examples include, but are not limited to, microbubbles of various compositions. Typically, microbubbles include a shell and a gas core. The shell may be composed of albumin, galactose, lipid, or polymers. One example is a biodegradable shell of polybutyl-2 cyanoacrylate. The gas core may be composed of air, nitrogen, or heavy gases like perfluorocarbon. For example, OPTISON (GE Healthcare) is an FDA approved microbubble for ultrasound imaging composed of an albumin shell and an octafluoropropane gas core. Examples of other ultrasound contrast agents include, but are not limited to, perfluorocytlbromide, perflutren lipid microspheres (DEFINITY; IMAGENT), sulfur hexafluoride (SONOVUE by Bracco), carbon dioxide gas, perfluorobutane, MRX-801, SONOLYSIS (ImaRx Therapeutics), TARGESTAR (Targeson), CARDIOSPHERE (POINT Biomedical), MAGNIFY (Acusphere, Inc), and the like.

Among contrast agents or enhancing agents used for diagnostic magnetic resonance imaging, examples include, but are not limited to, paramagnetic and supramagnetic agents with one or more unpaired electrons and typically include manganese, iron, or gadolinium in their structure. Examples of MRI contrast agents containing iron include, but are not limited to, ferumoxides (magnetite coated with dextran), ferumoxsil (magnetite coated with siloxane), ferumoxytol, ferumoxtran, ferucarbotran (RESOVIST), ferric chloride, ferric ammonium citrate, and the like. Examples of MRI contrast agents containing gadolinium include, but are not limited to, gadopentetate dimeglumine (Gd-DTPA; MAGNEVIST), gadobutrol (GADOVIST), gadodiamide (Gd-DTPA-BMA; OMNISCAN), gadoteridol (PROHANCE), Gd-DOTA (DOTAREM), gadofosveset trisodium (VASOVIST), gadoversetamide (OPTIMARK), gadobenate dimeglumine (MULTIHANCE), and the like. Examples of MRI contrast agents containing manganese include, but are not limited to, mangafodipir trisodium (TESLASCAN), EVP 1001-1, and the like.

Among agents for diagnostic positron emission tomography (PET), single photon emission computed tomography (SPECT), or gamma camera imaging, examples include, but are not limited to, any of a number of agents containing one or more short-lived radioactive elements. They are typically small organic molecules, but can also be macromolecules such as peptides or antibodies. Radioisotopes may be incorporated into a biologically active molecule such as a metabolic tracer or a natural or synthetic ligand or other binding agent targeted to a specific tissue or cellular location. For example, fluorine-18 fluorodeoxyglucose (FDG), a radioactive analog of glucose, is used to image highly metabolic solid tumors. Examples of other agents used for imaging or as tracers include, but are not limited to, compounds containing carbon-11, nitrogen-13, oxygen-15, and fluorine-18; salts of radioisotopes such as I-131 sodium iodide, Tl-201 thallous chloride, Sr-89 strontium chloride; technetium Tc-99m; compounds containing iodine-123, iodine-124, iodine-125, and iodine-131; compounds containing indium-111 such as $^{111}$In-1,4,7,10-Tetraazacyclododecane-N,N',N'',N'''-tetraacetic acid and $^{111}$In-Diethylenetriamine pentaacetic acid; $^{177}$Lu-[(R)-2-amino-3-(4-isothiocyanatophenyl)propyl]-trans-(S,S)-cyclohexane-1,2-diamine-pentaacetic acid) ($^{177}$Lu—CHX-A"-DTPA), $^{64}$Cu-DOTA, $^{89}$Zr, $^{86}$Y-DOTA, and the like.

Among agents used for diagnostic fluorescence imaging, examples include, but are not limited to, fluorescein (FITC), indocyanine green (ICG) and rhodamine B. Examples of other fluorescent dyes for use in fluorescence imaging include, but are not limited to, a number of red and near infrared emitting fluorophores (600-1200 nm) including cyanine dyes such as Cy5, Cy5.5, and Cy7 (Amersham Biosciences, Piscataway, N.J., USA) or a variety of Alexa Fluor dyes such as Alexa Fluor 633, Alexa Fluor 635, Alexa Fluor 647, Alexa Fluor 660, Alexa Fluor 680, Alexa Fluor 700, Alexa Fluor 750 (Molecular Probes-Invitrogen, Carlsbad, Calif., USA; see, also, U.S. Patent Pub. No. 2005/0171434 (published Aug. 4, 2005) (the contents of which are incorporated herein by reference), and the like.

Further examples of fluorophores include, but are not limited to, IRDye800, IRDye700, and IRDye680 (LI-COR, Lincoln, Nebr., USA), NIR-1 and 105-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS, ADS 821-NS (American Dye Source, Montreal, Calif.), NIAD-4 (ICx Technologies, Arlington, Va.), and the like. Further examples of fluorescing agents include BODIPY-FL, europium, green, yellow and red fluorescent proteins, luciferase, and the like. Quantum dots of various emission/excitation properties may be used for fluorescence imaging. See, e.g., Jaiswal, et al. Nature Biotech. 21:47-51 (2003) (the contents of which are incorporated herein by reference).

In an embodiment, one or more of the ferromagnetic microstructures 102 include one or more binding agents. For example, one or more ferromagnetic microstructures 102 may incorporate one or more binding agents configured to bind at least one of an imaging probe, at least one of a contrast agent or both. Among the one or more binding agents, examples include, but are not limited to, antibodies or fragments thereof, oligonucleotide or peptide based aptamers, receptors or parts thereof, artificial binding substrates formed by molecular imprinting, biomolecules, mutant or genetically engineered proteins or peptides, further details of which have been described herein.

In an embodiment, one or more of the ferromagnetic microstructures 102 include one of a ligand-receptor binding pair. In an embodiment, at least one of the ferromagnetic microstructures 102 includes one of a ligand-receptor binding pair. The one of a ligand-receptor binding pair is configured to bind to the other of the ligand-receptor binding pair to form the ligand-receptor binding pair. The other of the ligand-receptor binding pair is further associated with at least one of an imaging agent, at least one of a contrast agent, or both. The formation of the ligand-receptor binding pair links the ferromagnetic microstructures 102 to at least one of an imaging agent, at least one of a contrast agent, or both. Among ligand-receptor binding pairs, examples include, but are not limited to, antigen-antibody binding pairs, biotin-streptavidin binding pairs, biotin-avidin binding pairs, substrate-enzyme binding pairs, protein-protein binding pairs, protein-peptide binding pairs, primary antibody-secondary antibody binding pairs, sense oligonucleotide-antisense oligonucleotide binding pairs, aptamer-target binding pairs, artificial binding substrate-target binding pairs, peptide-nucleic acid (PNA)-DNA or RNA binding pairs.

Several technologies and methodologies can be use to assemble, link, bind, associate, or the like the various ligand-receptor binding pairs, ferromagnetic microstructures 102, contrast agents, imaging proves, or the like. In an embodiment, the ligand-receptor binding pair is an azide-alkyne binding pair that is capable of undergoing a cycloaddition chemical reaction in an in vivo biological system to form a covalent linkage. See, e.g., Baskin, et al., *Proc. Natl. Acad. Sci. USA* 104:16793-16797 (2007) (the contents of which are incorporated herein by reference).

In an embodiment, the formation of the ligand-receptor binding pair is performed after administration of the ferromagnetic microstructures 102 to a biological subject. The ferromagnetic microstructures 102 including one of a ligand-receptor binding pair can be administered to a biological subject before or after administration of the imaging probe or contrast agent including the other of the ligand-receptor binding pair. For example, the ferromagnetic microstructures 102 including one of a ligand-receptor binding pair and at least one targeting moiety can be administered to a biological subject and accumulated in one or more cell or tissue type based on the specificity of the targeting moiety. At a later time, at least one imaging agent or contrast agent including the other of the ligand-receptor binding pair is administered and binds to the one of the ligand-receptor binding pair of the ferromagnetic microstructures 102 previously accumulated in one or more cells or tissue types. Alternatively, the ferromagnetic microstructures 102 and imaging probe or contrast agent including one or the other of the ligand-receptor binding pair can be administered to a biological subject separately but essentially concurrently. In an embodiment, the formation of the ligand-receptor binding pair to link the ferromagnetic microstructures 102 and at least one imaging probe, contrast agent, or both can be performed prior to administering the ferromagnetic microstructures 102 to a biological subject.

In an embodiment, one or more of the ferromagnetic microstructures 102 include one or more binding agents attached thereof. In an embodiment, one or more of the binding agents are configured to bind to at least one imaging probe. In an embodiment, one or more of the binding agents are configured to bind to at least one imaging probe in vivo. In an embodiment, one or more of the ferromagnetic microstructures 102 include one of a ligand-receptor binding pair attached thereof.

In an embodiment, the one of the ligand-receptor binding pair is configured to bind with an imaging probe including the other of the ligand-receptor binding pair. In an embodiment, the one of the ligand-receptor binding pair is configured to bind, in vivo, with an imaging probe including the other of the ligand-receptor binding pair. In an embodiment, one or more of the ferromagnetic microstructures 102 include one or more binding agents attached thereof. In an embodiment, one or more of the binding agents are configured to bind to at least one contrast agent. In an embodiment, one or more of the binding agents are configured to bind to at least one contrast agent in vivo. In an embodiment, one or more of the ferromagnetic microstructures 102 include one of a ligand-receptor binding pair attached thereof. In an embodiment, the one of the ligand-receptor binding pair is configured to bind with an contrast agent including the other of the ligand-receptor binding pair. In an embodiment, the one of the ligand-receptor binding pair is configured to bind, in vivo, with an contrast agent including the other of the ligand-receptor binding pair.

In general, any of a number of homobifunctional, heterofunctional, or photoreactive cross-linking agents can be used to link the targeting moiety 112 to the ferromagnetic microstructure 102. The targeting moiety 112 can be linked to the ferromagnetic microstructure 102 through, for example, amine groups, sulfhydryl groups, carbohydrate groups, or a combination thereof. Examples of homobifunctional cross-linkers include, but are not limited to, primary amine/primary amine linkers such as BSOCES ((bis(2-[succinimidooxy-carbonyloxy]ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis (succinimidyl propionate), EGS (ethylene glycol bis(succinimidyl succinate)) and sulfhydryl/sulfhydryl linkers such as DPDPB (1,4-di-(3'-[2' pyridyldithio]-propionamido) butane). Examples of heterofunctional cross-linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-gamma-maleimidobutyryloxysulfosuccinimide ester), EMCS (N-(epsilon-maleimidocaproyloxy) succinimide ester), Sulfo EMCS(N-(epsilon-maleimidocaproyloxy) sulfo succinimide), SIAB (N-succinimidyl(4-iodoacetyl)aminobenzoate), SMCC (succinimidyl 4-(N-maleimidomethyl)cyclohexane-1-carboxylate), SMPB (succinimidyl 4-(rho-maleimidophenyl) butyrate), Sulfo SIAB (N-sulfosuccinimidyl(4-iodoacetyl) aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl)butyrate), and MAL-PEG-NHS (maleimide PEG N-hydroxysuccinimide ester); sulfhydryl/hydroxyl linkers such as PMPI (N-rho-maleimidophenyl)isocyanate; sulfhydryl/carbohydrate linkers such as EMCH(N-(epsilon-maleimidocaproic acid) hydrazide); and amine/carboxyl linkers such as EDC (1-ethyl-3-(3-dimethylaminopropyl)carbodiimide hydrochloride).

A targeting moiety 102 can be linked to a ferromagnetic microstructure 102 through an azide-alkyne mediated linkage. The copper-catalyzed azide-alkyne cycloaddition is a 1,3-dipolar cycloaddition between an azide and a terminal alkyne to form a triazole (see, e.g., Heine et al., *Pharm. Res.* 25:2216-2230, 2008; Ming, et al., *Nucleic Acids Symp. Ser. (Oxf).* 52:471-472, 2008; Van Dongen, et al., *Bioconjugate Chem.* 20:20-23, 2009; Godeau, et al, *J. Med. Chem.* 51:4374-4376, 2008, which are incorporated herein by reference). A copper-free cycloaddition reaction has also been described for use in living cells (see, e.g., Baskin et al., *Proc. Natl. Acad. Sci., USA.* 104:16793-16797, 2007, which is incorporated herein by reference). To link one or more components, one component is derivatized with azide while the other component is derivatized with alkyne and snapped together using "click chemistry". For example, the targeting moiety and the ferromagnetic microstructures can be functionalized with azide and/or alkyne for use in "click chemistry" reactions and "snapped" together.

Alternatively, ferromagnetic microstructures 102 can be tethered to a protein transduction domain (PTD) to facilitate entry of the ferromagnetic microstructure in a cell and/or across the blood brain barrier. Examples of PTDs include the human immunodeficiency virus type 1 (HIV-1) transactivator of transcription (Tat), antennapedia peptide, herpes simplex virus VP22, buforin, lipid membrane translocating peptide, mastoparan, and transportan. In one aspect, all or part of the 86 amino acid long Tat PTD may be added to the ferromagnetic microstructures through primary amines associated with the peptide and/or the functionalized ferromagnetic microstructures using the methods described herein (also see, e.g., Santra, et al., *Chem. Commun.* 24:2810-2811, 2004, which is incorporated herein by reference).

Under certain conditions, the ferromagnetic microstructures 102 can be actively taken up by a cell through the process of endocytosis whereby cells absorb extracellular material by engulfing the material with their cell membrane. The engulfed material is contained in small vesicles that pinch off from the plasma membrane, enter the cytoplasm and fuse with other intracellular vesicles, e.g., endosomes or lysosomes. The ferromagnetic microstructure 102 can be released from endosomes by a number of mechanisms. In an aspect, artificial acceleration of endosomal release may be achieved by photo-excitation of fluorescent probes associated with the engulfed material (see, e.g., Matsushita, et al., *FEBS Lett.* 572:221-226, 2004, which is incorporated herein by reference). Alternatively, the ferromagnetic microstructure may include a pH sensitive element that is activated in the low pH environment of the endosome. For example, all or part of the influenza virus hemagglutinin-2 subunit (HA-2), a pH-dependent fusogenic peptide that induces lysis of membranes at low pH, may be used to induce efficient release of encapsulated material from cellular endosomes (see, e.g., Yoshikawa, et al., *J. Mol. Biol.* 380:777-782, 2008, which is incorporated herein by reference).

The ferromagnetic microstructure 102 may enter the cell by passing directly through the cell membrane and into the cytoplasm. In this instance, the tubular nanostructure may include moieties on the surface of the microstructure that confer direct passage through the lipid bilayer, e.g., an amphipathic striated surface coating. For example, the deposition of a hydrophilic-hydrophobic striated pattern of molecules, e.g., the anionic ligand 11-mercapto-1-undecanesulphonate (MUS) and the hydrophobic ligand 1-octanethiol (OT) on the surface of microstructures can facilitate direct passage of the microstructure across cellular membranes (see, e.g., Verma, et al., *Nature Materials* 7:588-95, 2008, which is incorporated herein by reference).

Further examples of techniques and methodologies for targeting ferromagnetic microstructures 102 may be found in, for example, the following documents (the contents of which are incorporated herein by reference): Peng et al., *Targeted Magnetic Iron Oxide Nanoparticles for Tumor Imaging and Therapy*, International journal of nanomedicine 3(3):311-21 (2008); Selim et al., *Surface Modification of Magnetite Nanoparticles Using Lactobionic Acid and Their Interaction With Hepatocytes*, Biomaterials, 28(4):710-6 (2007); Serda et al., *Targeting and Cellular Trafficking of Magnetic Nanoparticles for Prostate Cancer Imaging*, Mol. Imaging. 6(4):277-88 (2007); Quantum dot-trastuzumab [QT], Molecular Imaging and Contrast Agent Database NIH, 1-5 (2007) (http://www.ncbi.nlm.nih.gov/bookshelf/br.fcgi?book=micad&part=Qd-Trastuzumab); Chopra, A., Monoclonal antibody against antigen A7 coupled to ferromagnetic lignosite particles [A7-FML], Molecular Imaging and Contrast Agent Database NIH, 1-4 (2008) (http://www.ncbi.nlm.nih.gov/bookshelf/br.fcgi?book=micad&part=A7-FMLMRI); and U.S. Patent Publication No. 2009/0029392 (published Jan. 29, 2009.)

In an embodiment, one or more surfaces of a ferromagnetic microstructure 102 are functionalized with one or more functional groups. Various technologies and methodologies can be use to modify a surfaces of a ferromagnetic microstructure 102 so that a plurality of functional groups is present thereon. The manner of treatment is dependent on, for example, the nature of the chemical compound to be synthesized and the nature and composition of the surface. See, e.g., U.S. Patent Publication No. 2007/0078376 (published Apr. 5, 2007) (the contents of which are incorporated herein by reference). In some embodiments, the surface may include functional groups selected to impart one or more of properties to the surface including nonpolar, hydrophilic, hydrophobic, organophilic, lipophilic, lipophobic, acidic, basic, neutral, properties, increased or decreased permeability, and the like, and/or combinations thereof. For example, one or more of the ferromagnetic microstructures 102 can include one or more functional groups that impart or more functionalities (e.g., charge functionally, hydrophobic functionally, hydrophilic functionally, chemically reactive functionally, organo functionally, water-wettable functionally, or the like) to the ferromagnetic microstructures 102.

In an embodiment, one or more of the ferromagnetic microstructures 102 include one or more functional groups that are useful to attach (e.g., link, bind, conjugate, complex, associate, or the like) a targeting moiety 112 to the ferromagnetic microstructure 102. In an embodiment, one or more of the ferromagnetic microstructures 102 include one or more functional groups that impart one or more properties (e.g., chemical properties, chemically reactive properties, association properties, electrostatic interaction properties, bonding properties, biocompatible properties, or the like) to the ferromagnetic microstructures 102 including acidic, basic, hydrophilic, hydrophobic, lipophilic, lipophobic, neutral, nonpolar, organophilic, properties, increased or decreased permeability, and the like, and combinations thereof.

Among functional groups, examples include, but are not limited to chemical groups that confer special properties or particular functions to the ferromagnetic microstructures 102. Among chemical groups, examples include, but not limited to, an atom, an arrangement of atoms, an associated group of atoms, molecules, moieties, and the like, that confer certain characteristic properties on the ferromagnetic microstructures 102 including the functional groups. Further examples of functional groups include, charge functional groups, hydrophobic functional groups, hydrophilic functional groups, chemically reactive functional groups, organofunctional group, water-wettable groups, bio-compatible functional groups, and the like. Further examples of function groups include nonpolar functional groups, hydrophilic functional groups, hydrophobic functional groups, organophilic functional groups, lipophilic functional groups, lipophobic functional groups, acidic functional groups, basic functional groups, neutral functional groups, and the like. In an embodiment, the functional groups may impart one or more properties to a surface of the ferromagnetic microstructures 102 including, for example, nonpolar, hydrophilic, hydrophobic, organophilic, lipophilic, lipophobic, acidic, basic, neutral, properties, increased or decreased permeability, and the like, and/or combinations thereof. Further examples of function groups include alcohols, hydroxyls, amines, aldehydes, dyes, ketones, cabonyls, thiols, phosphates, carboxyls, caboxilyic acids, carboxylates, proteins, lipids, polysaccharides, pharmaceuticals, metals, —CO—R, —NH$_3^+$, —COOH, —COO$^-$, —SO$_3$, —CH$_2$N$^+$(CH$_3$)$_3$, —(CH$_2$)$_m$CH$_3$, —C((CH$_2$)$_m$CF$_3$)$_3$, —CH$_2$N(C$_2$H$_5$)$_2$, —NH$_2$, —(CH$_2$)$_m$COOH, —(OCH$_2$CH$_2$)$_m$CH$_3$, —SiOH, —OH, and the like.

In an embodiment, one or more of the ferromagnetic microstructures 102 include one or more immobilized targeting moieties 112. In an embodiment, one or more of the ferromagnetic microstructures 102 include a siloxane-scaffold on one or more surfaces. In an embodiment, the siloxane-scaffold is configured to immobilize one or more targeting moieties 112 to a surface of the ferromagnetic microstructures 102. See e.g., Dow Corning, *Guide to Silane Solutions*, (2005) (http://www.dowcorning.com/content/publishedlit/SILANE-GUIDE.pdf). In an embodiment, one or more of the plurality of ferromagnetic microstructures 102 include, but are not limited to, a siloxane coating, a silane coating, or the like.

In an embodiment, a composition includes one or more ferromagnetic microstructures 102 having an external surface 110 and an internal surface 104, the internal surface 104 defining a void 106, the void 106 being accessible to a biological sample. In an embodiment, one or more ferromagnetic microstructures 102 are configured to generate a time-invariant magnetic field 108 within at least a portion of the void. In an embodiment, one or more targeting moieties 112 are attached to at least one of the one or more of the ferromagnetic microstructures 102.

In an embodiment, at least one of the internal surface 104 or the external surface 110 includes one or more functional groups. In an embodiment, the one or more functional groups include at least one of a bio-compatible functional group, a charge functional group, a chemically reactive functional group, a hydrophilic functional group, a hydrophobic functional group, or an organofunctional group. In an embodiment, either the internal surface 104 or the external surface 110, or both may be modified to include one or more functional groups. In an embodiment, at least a portion of the internal surface 104, the external surface 110, or both may be modified to include one or more functional groups. In an embodiment, at least the interior surface 104 of one or more of the ferromagnetic microstructures 102 is modified with a sufficient amount of one or more functional groups.

In an embodiment, a functional groups may include a binding group (e.g., coupling agents, and the like), a linking group (e.g., spacer groups, organic spacer groups, and the like), and/or a matrix-forming group that aid in, for example, binding the functional groups to the internal surface 104, the external surface 110, or both, or aid in providing the desired functionality. Among binding groups, examples include, but are not limited to, acrylates, alkoxysilanes, alkyl thiols, arenes, azidos, carboxylates, chlorosilanes, alkoxysilanes, acetocysilanes, silazanes, disilazanes, disulfides, epoxides, esters, hydrosilyl, isocyanates, and phosphoamidites, isonitriles, methacrylates, nitrenes, nitriles, quinones, silanes, sulfhydryls, thiols, vinyl groups, and the like.

Among linking groups, examples include, but are not limited to, dendrimers, polymers, hydrophilic polymers, hyperbranched polymers, poly(amino acids), polyacrylamides, polyacrylates, polyethylene glycols, polyethylenimines, polymethacrylates, polyphosphazenes, polysaccharides, polysiloxanes, polystyrenes, polyurethanes, propylene's, proteins, telechelic block copolymers, and the like.

Among matrix-forming groups, examples include, but are not limited to, dendrimer polyamine polymers, bovine serum albumin, casein, glycolipids, lipids, heparins, glycosaminoglycans, muscin, surfactants, polyoxyethylene-based surface-active substances (e.g., polyoxyethlene-polyoxypropylene copolymers, polyoxyethylene 12 tridecyl ether, polyoxyethylene 18 tridecyl ether, polyoxyethylene 6 tridecyl ether, polyoxyethylene sorbitan tetraoleate, polyoxyethylene sorbitol hexaoleate, and the like) polyethylene glycols, polysaccharides, serum dilutions, and the like.

An aspect includes systems, devices, methods, and compositions including, among other things, ferromagnetic microstructures 102 configured to allow selective-accessible to one or more internal surface defined voids 106. A non-limiting approach includes systems, devices, methods, and compositions including, among other things, ferromagnetic microstructures 102 having an interior that is selectively accessible to a biological sample. A non-limiting approach includes systems, devices, methods, and composition including, among other things, one or more of the ferromagnetic microstructure sets configured to allow an in vivo biological sample selective-access to one or more internal voids 106. A non-limiting approach includes systems, devices, methods, and compositions including, among other things, targeted ferromagnetic microstructures having an interior that is selectively accessible to a biological sample. In an embodiment, the targeted ferromagnetic microstructures 102 include one or more targeting moieties 112 attached thereof. In an embodiment, one or more of the ferromagnetic microstructure sets include one or more ferromagnetic microstructures including one or more bound targeting moieties 112.

Figure 2:
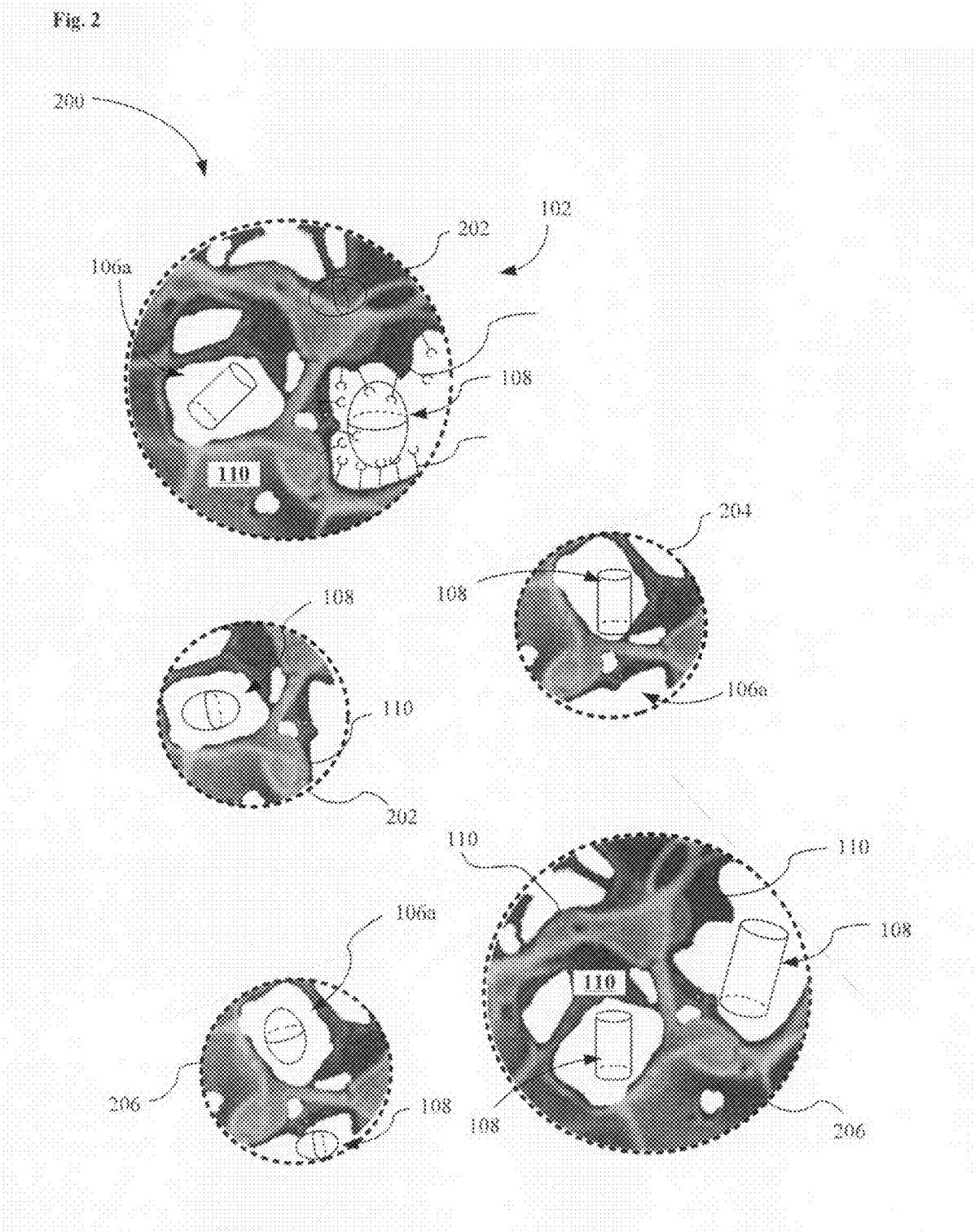
FIG. 2 is a perspective view of a plurality of ferromagnetic microstructures according to one illustrated embodiment.

Referring to FIGS. 2A and 2B, in an embodiment, one or more of the ferromagnetic microstructure sets 200 include, but are not limited to, an ion selective selectively-accessible internal void 106a. In an embodiment, one or more of the ferromagnetic microstructure sets 200 include, but are not limited to, a molecule selective selectively-accessible internal void 106a.

In an embodiment, one or more of the plurality of ferromagnetic microstructures include, but are not limited to, a first internal surface 104 defining a void 106a configured to be selectively-accessible to a biological sample. In an embodiment, one or more of the plurality of ferromagnetic microstructures include a sufficient amount of one or more ferromagnetic materials to generate a time-invariant magnetic field 108 within the selectively-accessible void 106a. In an embodiment, one or more of the plurality of ferromagnetic microstructures 102 include, but are not limited to, a coating 202 that selectively allows access to the defined void 106. In an embodiment, one or more of the plurality of ferromagnetic microstructures 102 include, but are not limited to, one or more pH-sensitive polymer coatings configured to selectively allow access to the defined void 106. In an embodiment, one or more of the plurality of ferromagnetic microstructures 102 include, but are not limited to, a membrane 204 that selectively allows access to the defined void 106. In an embodiment, one or more of the plurality of ferromagnetic microstructures 102 include, but are not limited to, a degradable membrane that selectively allows access to the defined void 106.

In an embodiment, one or more of the plurality of ferromagnetic microstructures 102 include, but are not limited to, a component 206 that selectively allows access to the defined void 106. In an embodiment, one or more of the plurality of ferromagnetic microstructures 102 include, but are not limited to, a degradable component that selectively allows access to the defined void 106. In an embodiment, one or more of the plurality of ferromagnetic microstructures 102 include, but are not limited to, a pH sensitive degradable component that selectively allows access to the defined void 106. In an embodiment, one or more of the plurality of ferromagnetic microstructures 102 include, but are not limited to, a pH degradable component configured to selectively allow access to the defined void 106. In an embodiment, one or more of the plurality of ferromagnetic microstructures 102 include, but are not limited to, a photodegradable component that selectively allows access to the defined void 106.

In an embodiment, one or more of the plurality of ferromagnetic microstructures 102 include, but are not limited to, a degradable polymeric substrate that selectively allows access to the defined void 106. In an embodiment, one or more of the plurality of ferromagnetic microstructures 102 include, but are not limited to, a shape-memory component including one or more shape-memory polymers. See, e.g., Farokhzad et al., *Drug Delivery Systems in Urology-Getting "Smarter"*, Urology 68(3); 463-469 (2006) (the contents of which are incorporated herein by reference). In an embodiment, one or more of the plurality of ferromagnetic microstructures 102 include, but are not limited to, a biodegradable polymer shape-memory component. In an embodiment, one or more of the plurality of ferromagnetic microstructures 102 include, but are not limited to, a biodegradable polymer component. In an embodiment, one or more of the plurality of ferromagnetic microstructures 102 include, but are not limited to, an ion-selective component that selectively allows access to the defined void 106. In an embodiment, one or more of the plurality of ferromagnetic microstructures 102 include, but are not limited to, a charge-selective component that selectively allows access to the defined void 106. In an embodiment, one or more of the plurality of ferromagnetic microstructures 102 include, but are not limited to, a size-selective component that selectively allows access to the defined void 106. In an embodiment, one or more of the plurality of ferromagnetic microstructures 102 include, but are not limited to, a size-exclusion component that selectively restricts access to the defined void 106.

Figure 3A:
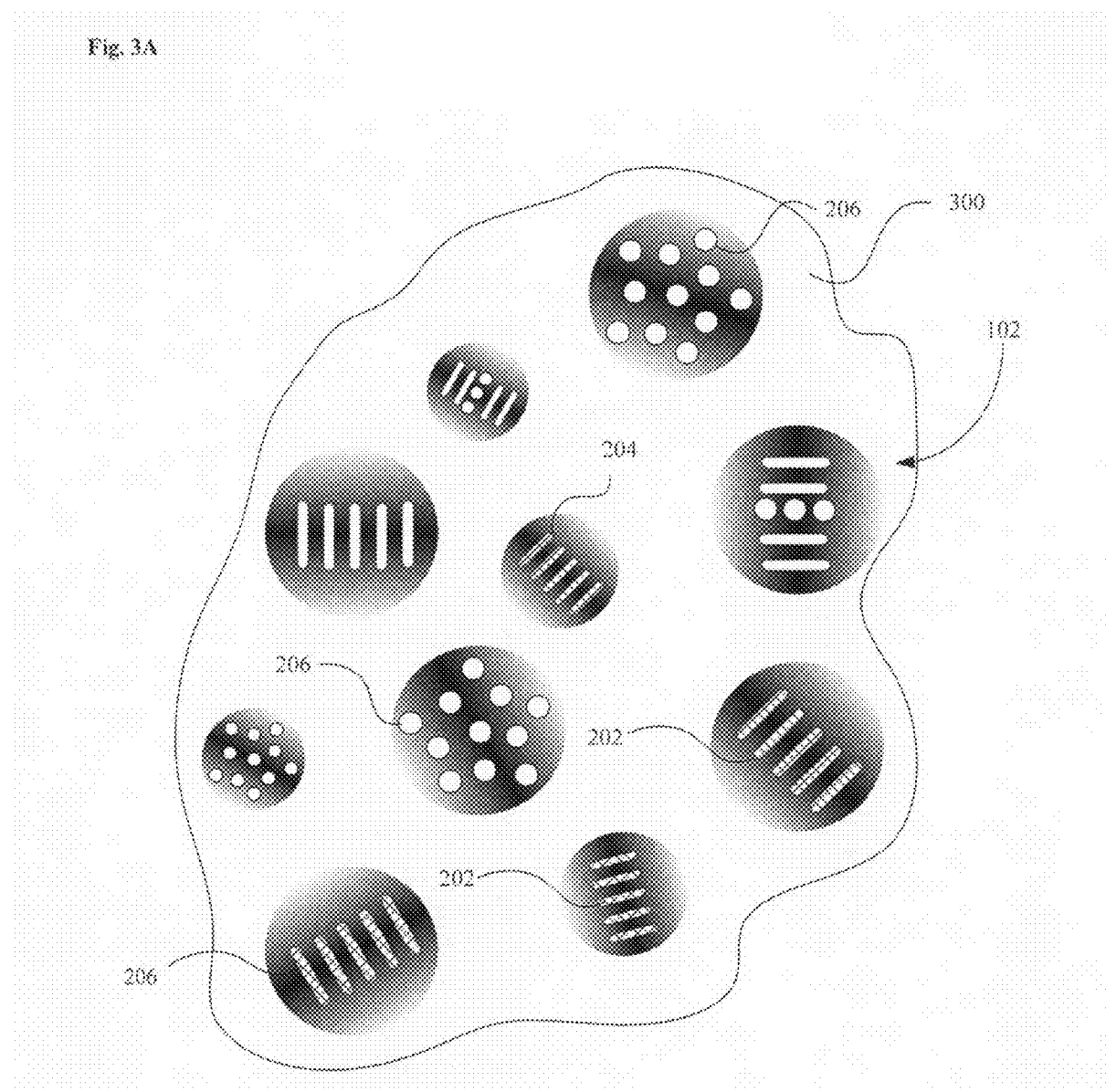
FIGS. 3A, 3B, and 3C are perspective views of pluralities of ferromagnetic microstructures according to multiple illustrated embodiments.
Figure 3B:
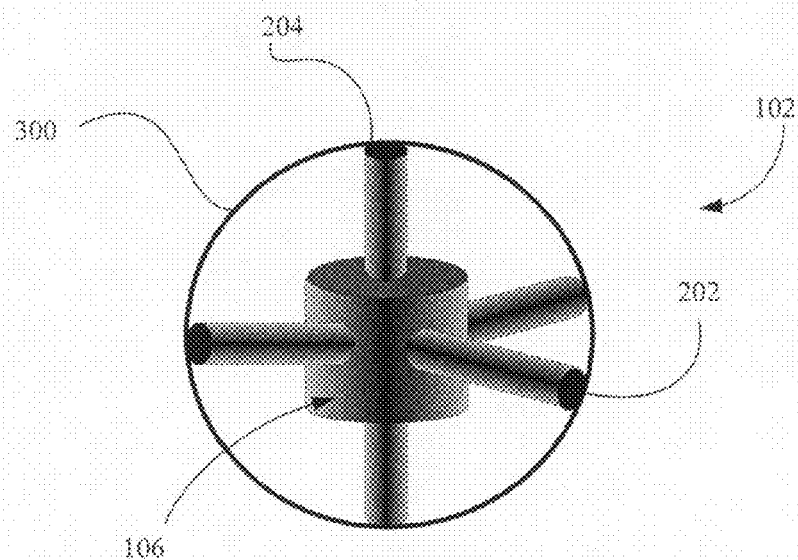
Figure 3C:
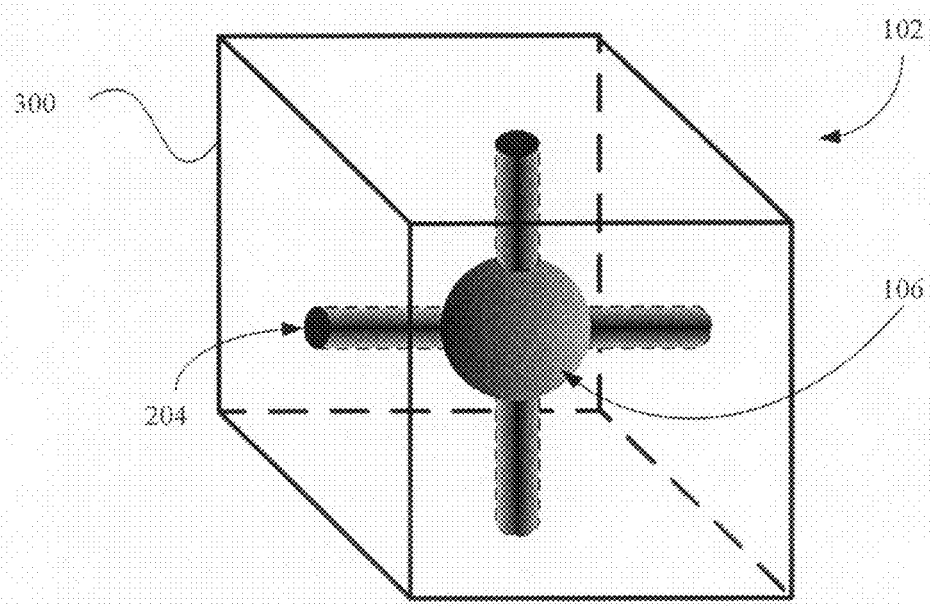

Referring to FIGS. 3A, 3B, and 3C, a non-limiting approach includes systems, devices, methods, and compositions including, among other things, ferromagnetic microstructures 102 that are incorporated in a matrix material 300 that that selectively allows access to an interior of the ferromagnetic microstructures 102. A non-limiting approach includes systems, devices, methods, and compositions including, among other things, ferromagnetic microstructures 102 that are oriented and encapsulated in a matrix material 300 that that selectively allows access to an interior of the ferromagnetic microstructures 102. Dry pressing, quickly solidifying, annealing, or the like the matrix material 300 while applying magnetic field to orient the ferromagnetic microstructures 102. Other techniques and methodologies for fabricating ferromagnetic microstructures 102 that are oriented and encapsulated in a matrix material 300 include those used in creating structures such as, for example, aerogels, hydrogels, nanogels, sol-gels, xerogels, or the like. In an embodiment, ferromagnetic microstructures 102 that are incorporated in a matrix can be sintered, cross-linked, adhered, or joined otherwise to for larger structures. In an embodiment, individual ferromagnetic microstructures 102 can be coated and subsequently sintered, cross-linked, adhered, or joined otherwise to for larger structures.

In an embodiment, individual ferromagnetic microstructures 102 can be sintered to form ferromagnetic microstructures 102 of varying sizes and dimension. In an embodiment, individual ferromagnetic microstructures 102 can be sintered in the presence of a magnetic field to form ferromagnetic microstructures 102 of varying magnetic properties.

FIG. 4 shows a system 400 in which one or more methodologies or technologies may be implemented. In an embodiment, the system 400 includes one or more radio frequency (RF) transmitter assemblies 402 including at least one RF transmitters configured to generate an RF signal. In an embodiment, RF pulses delivered by the RF transmitter assembly 402 excite a region of interest within a biological subject. See, e.g., the following documents (the contents of which are incorporated herein by reference): U.S. Pat. Nos. 5,175,499 (issued Dec. 29, 1992), 6,275,722 (issued Aug. 14, 2001), 6,873,153 (issued Mar. 29, 2005), 6,879,160 (issued Apr. 12, 2005), 6,977,503 (issued Dec. 20, 2005), 7,075,302 (issued Jul. 11, 2006), 7,096,057 (issued Aug. 22, 2006), 7,095,230 (issued Aug. 22, 2006), 7,309,986 (issued Dec. 18, 2007), 7,418,289 (issued Aug. 26, 2008), 7,483,732 (issued Jan. 27, 2009), and 7,495,439 (issued Feb. 24, 2009); U.S. Patent Publ. Nos. 2007/0194788 (published Aug. 23, 2007), and 2008/0306377 (Dec. 11, 2008), 2009/0015256 (published Jan. 15, 2009); WO 2005/101045 (published Oct. 27, 2005), WO 2009/027973 (published Mar. 5, 2009), WO 2009/029880 (published Mar. 5, 2009), and WO 2009/029896 (published Mar. 5, 2009).

In an embodiment, an RF transmitter assembly 402 can include one or more of controllers, digital attenuators, digital-to-analog converters, amplifiers (e.g., power amplifiers, RF amplifiers, or the like), RF synthesizer, signal conditioning amplifiers, transmitting coils (e.g., RF transmitting coils, or the like), and waveform generators. In an embodiment, the system 400 includes at least one coil configured to generate one or more RF pulses based on, for example, a control input, output, a command, or a response. In an embodiment, an RF transmitter operating in conjunction with, for example, an RF oscillator, generates an RF signal. An RF amplifier amplifies the RF signal that drives an RF transmitter coil that in turn provides RF pulses that excite the nuclear magnetization of non-zero spin nuclei in a region of interest. In an embodiment, an RF transmitted coil including a transmit/receive switch can be used as a receiver coil.

In an embodiment, the system 400 includes one or more RF receiver assemblies 404 including at least one RF receiver configured to acquire RF information emitted by the biological sample. In an embodiment, an RF receiver assembly 402 can include one or more of analog-to-digital converters, matching networks, oscillators, power amplifiers, RF receive coils, RF synthesizers, or signal filters. In an embodiment, the system 400 includes one or more RF transceivers 406 configured to generate RF excitation pulses that interacts with, for example, in vivo target non-zero spin nuclei.

In an embodiment, the system 400 includes one or more magnetic resonance detectors 408. Examples of magnetic resonance detectors can be found in, for example, the following documents (the contents of which are incorporated herein by reference): U.S. Pat. Nos. 7,271,589 (issued Sep. 18, 2007) and 7,258,734 (issued Apr. 15, 2008); U.S. Patent Publ. Nos. 2009/0015256 (published Jan. 15, 2009), 2007/0194788 (published Aug. 23, 2007), and 2007/0020701 (published Jan. 25, 2007). In an embodiment, the one or more magnetic resonance detectors 408 are configured to detect (e.g., assess, calculate, evaluate, determine, gauge, measure, monitor, quantify, resolve, sense, or the like) emitted nuclear magnetic information (e.g., RF information, an RF signal, a nuclear magnetic resonance, an in vivo magnetic resonance event generated by nuclear magnetic resonance detectable nuclei, or the like) and to generate a response based on the detected nuclear magnetic information.

In an embodiment, the response includes at least one of a display, a visual representation (e.g., a plot, a display, a spectrum, a visual depiction representative of the detected information, a visual depiction representative of a physical object (e.g., a ferromagnetic microstructure, a contrast agent, tissue, an indwelling implant, fat, muscle, bone, non-zero spin nuclei, a biological fluid component, or the like) a visual display, a visual display of at least one spectral parameter, and the like. In an embodiment, the response includes at least one of a visual representation, an audio representation (e.g., an alarm, an audio waveform representation of a magnetic resonance event, or the like), or a tactile representation (e.g., a tactile diagram, a tactile display, a tactile graph, a tactile interactive depiction, a tactile model (e.g., a multidimensional model of a physical object or a magnetic resonance event, or the like), a tactile pattern (e.g., a refreshable Braille display), a tactile-audio display, a tactile-audio graph, or the like). In an embodiment, the response includes an output, a response signal, a display, a data array, or a spectral plot. In an embodiment, the response includes one or more images associated with at least one of a spatial distribution of $T_1$ relaxation time information or a spatial distribution of $T_2$ relaxation time information. In an embodiment, the response includes a visual representation indicative of a parameter associated with one or more ferromagnetic microstructures.

In an embodiment, the system 400 includes one or more gradient coil assemblies 410 including at least one gradient coil configured to spatially encode a position of NMR active nuclei by, for example, varying the magnetic field linearly across an imaging volume. The Larmor frequency of the NMR active nuclei will then vary as a function of position in the x, y and z-axes. In an embodiment, the system 400 includes one or more RF coil assemblies 412.

The system 400 can be used alone or in combination with other diagnostic imaging techniques and methodologies such as, for example, x-ray imaging, computed tomography (CT), ultrasound, magnetic resonance imaging (MRI), positron emission tomography (PET), single photon emission computed tomography (SPECT), gamma camera imaging, fluorescence tomography, or the like. In an embodiment, the system 400 includes one or more contrast agent detection assemblies 414.

In an embodiment, the system 400 includes means for affecting an in vivo magnetic resonance relaxation process associated with a biological sample, in the absence of an externally generated magnetic field. The means for affecting an in vivo magnetic resonance relaxation process includes a plurality of ferromagnetic microstructures 102. The means for affecting an in vivo magnetic resonance relaxation process can further include for example, but not limited to, electrical control components, electromechanical control components, software control components, firmware control components, circuitry control components, or other control components, or combinations thereof. Examples of circuitry control components can be found, among other things, in U.S. Pat. No. 7,236,821 (issued Jun. 26, 2001) (the contents of which are incorporated herein by reference).

In an embodiment, the system 400 can includes one or more components 416 (e.g., hardware, software, firmware, mechanical systems, electro-mechanical system, or the like) associated with other diagnostic imaging techniques and methodologies such as, for example, x-ray imaging, computed tomography (CT), ultrasound, magnetic resonance imaging (MRI), positron emission tomography (PET), single photon emission computed tomography (SPECT), gamma camera imaging, fluorescence tomography, or the like.

In a general sense, the various aspects described herein (which can be implemented, individually and/or collectively, by a wide range of hardware, software, firmware, and/or any combination thereof) can be viewed as being composed of various types of "electrical circuitry." Consequently, as used herein electrical circuitry or electrical control component circuitry includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

Consequently, as used herein electro-mechanical system includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include, but are not limited to, a variety of consumer electronics systems, medical devices, as well as other systems such as motorized transport systems, factory automation systems, security systems, and/or communication/computing systems. The term, electro-mechanical, as used herein is not necessarily limited to a system that has both electrical and mechanical actuation except as context may dictate otherwise.

In an embodiment, the means for affecting an in vivo magnetic resonance relaxation process can include a nuclear magnetic resonance imaging composition including, but is not limited to, one or more ferromagnetic microstructures 102. In an embodiment, one or more of the ferromagnetic microstructures 102 include, but are not limited to, at least a first internal surface 104 defining a void 106 accessible to a biological sample. In an embodiment, one or more of the ferromagnetic microstructures 102 include at least an outer surface 110. In an embodiment, the means for affecting an in vivo magnetic resonance relaxation process can further include an RF transmitter assembly 402 including one or more of controllers, digital attenuators, digital-to-analog converters, amplifiers (e.g., power amplifiers, RF amplifiers, or the like), RF synthesizer, signal conditioning amplifiers, transmitting coils (e.g., RF transmitting coils, or the like), and waveform generators. In an embodiment, the means for affecting an in vivo magnetic resonance relaxation process can further include one or more RF receiver assemblies 404 including at least one RF receiver configured to acquire RF information emitted by the biological sample. In an embodiment, an RF receiver assembly 402 can include one or more of analog-to-digital converters, matching networks, oscillators, power amplifiers, RF receive coils, RF synthesizers, or signal filters. In an embodiment, the system 400 includes one or more RF transceivers 406 configured to generate RF excitation pulses that interacts with, for example, in vivo target non-zero spin nuclei.

In an embodiment, one or more of the ferromagnetic microstructures 102 are configured to generate one or more time-invariant magnetic fields 108 within at least a portion of the void 106. In an embodiment, the time-invariant magnetic field 108 within the void 106 includes a substantially homogeneous polarizing magnetic field region. In an embodiment, at least a first internal surface 104 of at least one of the one or more ferromagnetic microstructures 102 includes one or more targeting moieties 112. In an embodiment, at least an outer surface 110 of at least one of the one or more ferromagnetic microstructures 102 includes one or more targeting moieties 112. In an embodiment, a majority of the one or more targeting moieties 112 is localize to a portion of the void 106 including a time-invariant magnetic field 108.

In an embodiment, the means for affecting an in vivo magnetic resonance relaxation process can include circuitry for acquiring information associated with an in vivo magnetic resonance event generated by nuclear magnetic resonance detectable nuclei received in one or more voids 106 of a plurality of ferromagnetic microstructures configured to generate a static magnetic field within the void 106.

In an embodiment, the means for affecting an in vivo magnetic resonance relaxation process can include at least one of RF transmitter assemblies 402, RF receiver assemblies 404, RF transceivers 406, magnetic resonance detectors 408, gradient coil assemblies 410, RF coil assemblies 412, contrast agent detection assemblies 414, or the like. For example, in an embodiment, the means for affecting an in vivo magnetic resonance relaxation process can include an RF transmitter assembly 402 including one or more of controllers, digital attenuators, digital-to-analog converters, amplifiers (e.g., power amplifiers, RF amplifiers, or the like), RF synthesizer, signal conditioning amplifiers, transmitting coils (e.g., RF transmitting coils, or the like), or waveform generators. In an embodiment, the means for affecting an in vivo magnetic resonance relaxation process can include at least one coil configured to generate one or more RF pulses based on, for example, a control input, output, a command, or a response an RF transmitter operating in conjunction with, for example, but not limited to, an RF oscillator, generates an RF signal. This RF signal can be amplified by the RF amplifier to, for example, drive and RF transmitter coil that provides RF pulses that excite the nuclear magnetization of non-zero spin nuclei of in a region of interest.

In an embodiment, the means for affecting an in vivo magnetic resonance relaxation process can include circuitry for generating a response based on the acquiring information.

In an embodiment, the response includes generating a representation (e.g., depiction, rendering, modeling, or the like) of at least one physical parameter associated with one or more non-zero spin nuclei. In an embodiment, the response includes generating a visual representation of at least one physical parameter associated with one or more non-zero spin nuclei. In an embodiment, the response includes generating a visual representation of at least one physical characteristic associated with one or more non-zero spin nuclei. In an embodiment, the response includes a visual representation of at least one spectral parameter associated with one or more non-zero spin nuclei. In an embodiment, the response includes generating a visual representation of at least one spectral parameter associated with one or more targeting moieties. In an embodiment, the response includes generating a visual representation of at least one spectral parameter associated with one or more ferromagnetic microstructures. In an embodiment, the response includes generating a visual representation of at least one of ferromagnetic microstructure spectral information, tissue-contained non-zero spin nuclei spectral information, tissue spectral information, indwelling implant spectral information, fat spectral information, muscle spectral information, or bone spectral information.

In an embodiment, the response includes at least one of a visual representation (e.g., a visual depiction representative of magnetically active object (e.g., a molecule, tissue, a ferromagnetic microstructure, or the like), a visual depiction representative of the detected (e.g., assessed, calculated, evaluated, determined, gauged, measured, monitored, quantified, resolved, sensed, or the like) information), an audio representation (e.g., an alarm, an audio waveform representation of a magnetic resonance event, or the like), or a tactile representation (e.g., a tactile diagram, a tactile display, a tactile graph, a tactile interactive depiction, a tactile model (e.g., a multidimensional model of a physical object or a magnetic resonance event, or the like), a tactile pattern (e.g., a refreshable Braille display), a tactile-audio display, a tactile-audio graph, or the like). In an embodiment, the response includes at least one of a display, a visual display, a visual display of at least one spectral parameter, and the like. In an embodiment, the response includes an output, a response signal, a display, a data array, or a spectral plot. In an embodiment, the response includes one or more images associated with at least one of a spatial distribution of $T_1$ relaxation time information or a spatial distribution of $T_2$ relaxation time information. In an embodiment, the response includes a visual representation indicative of a parameter associated with one or more ferromagnetic microstructures. In an embodiment, the response includes automatically modifying at least one of an RF power level, an RF pulsing protocol, or an RF detection protocol. In an embodiment, the response includes automatically accumulating increments of detected RF information acquired over two or more time intervals. In an embodiment, the response includes automatically storing data indicative of detected RF information.

In an embodiment, the means for affecting an in vivo magnetic resonance relaxation process can include circuitry for communicating the response to a user. In an embodiment, the system 400 includes circuitry for generating an RF magnetic field of a character and for a sufficient time to excite one or more of the nuclear magnetic resonance detectable nuclei received in the one or more voids 106 of the plurality of ferromagnetic microstructures 102.

In an embodiment, the means for acquiring at least one spatial distribution parameter of a magnetic resonance event associated with the affected in vivo magnetic resonance relaxation process includes an RF receiver assembly 402 configured to acquire RF information emitted by the biological sample. In an embodiment, the means for affecting an in vivo magnetic resonance relaxation process can include an RF transmitter 404 configured to generate an RF signal. In an embodiment, the means for affecting an in vivo magnetic resonance relaxation process includes one or more coil assemblies 412 configured to generate one or more RF pulses.

In an embodiment, the means for acquiring at least one spatial distribution parameter of a magnetic resonance event associated with the affected in vivo magnetic resonance relaxation process includes one or more controllers such as a processor (e.g., a microprocessor), a central processing unit (CPU), a digital signal processor (DSP), an application-specific integrated circuit (ASIC), a field programmable gate array (FPGA), or the like, and any combinations thereof, and can include discrete digital or analog circuit elements or electronics, or combinations thereof. The system 400 can include, but is not limited to, one or more field programmable gate arrays having a plurality of programmable logic components. In an embodiment, the means for acquiring at least one spatial distribution parameter of a magnetic resonance event associated with the affected in vivo magnetic resonance relaxation process can include, but is not limited to, one or more application specific integrated circuits having a plurality of predefined logic components. The system 400 can include, but is not limited to, one or more memories that, for example, store instructions or data, for example, volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further examples of one or more memories include Erasable Programmable Read-Only Memory (EPROM), flash memory, and the like. The one or more memories can be coupled to, for example, one or more controllers by one or more instruction, data, or power buses.

In an embodiment, the means for acquiring at least one spatial distribution parameter of a magnetic resonance event associated with the affected in vivo magnetic resonance relaxation process can include, but is not limited to, data structures (e.g., physical data). In an embodiment, a data structure includes nuclear magnetic information including one or more heuristically determined parameters associated with at least one in vivo or in vitro determined metric. Examples of heuristics include, a heuristic protocol, heuristic algorithm, threshold information, a target Larmor frequency, a target parameter, nuclear magnetic resonance information, magnetic resonance spectral information, or the like. The system 400 can include, but is not limited to, a means for generating one or more heuristically determined parameters associated with at least one in vivo or in vitro determined metric including one or more data structures. The system 400 can include, but is not limited to, a means for generating a response based on a comparison of detected nuclear magnetic information (e.g., an RF signal, a nuclear magnetic resonance, an in vivo magnetic resonance event generated by nuclear magnetic resonance detectable nuclei, or the like) to one or more heuristically determined parameters stored in one or more physical data structures, and to generate a response based on the comparison.

In an embodiment, at least one of the one or more RF transmitter assemblies 402, RF receiver assemblies 404, RF transceivers 406, magnetic resonance detectors 408, gradient coil assemblies 410, or contrast agent detection assemblies 414 can be, for example, wirelessly coupled to a controller that communicates with a control unit of the system 400 via wireless communication. Examples of wireless communication include for example, but not limited to, optical connections, ultraviolet connections, infrared, BLUETOOTH®, Internet connections, radio, network connections, and the like. The system 100 can include, but is not limited to, means for generating a response based on a comparison, of a detected at least one of an emitted interrogation energy or a remitted interrogation energy to at least one heuristically determined parameter, including one or more controllers.

In an embodiment, the system 400 includes means for generating a response based on an acquired at least one spatial distribution parameter. In an embodiment, magnetic resonance information generated from an non-zero spin nuclei within an interrogation region are detected by, one or more RF receiving coils and processed by the RF receiver assembly, including, for example, but not limited to, RF amplifiers, quadrature demodulator, and analog-to-digital converters.

In embodiment, a nuclear magnetic resonance imaging system includes a plurality of ferromagnetic microstructures 102. In an embodiment, one or more of the plurality of ferromagnetic microstructures 102 include a first internal surface 104 defining one or more voids 106, at least one of the one or more voids 106 is configured to be accessible to a biological sample. In an embodiment, one or more of the plurality of ferromagnetic microstructures 102 include a sufficient amount of one or more ferromagnetic materials to generate a time-invariant magnetic field 108 within at least a portion of at least one of the one or more voids 106.

An aspect includes systems and devices including, among other things, means for affecting an in vivo magnetic resonance relaxation process associated with a biological sample, in the absence of an externally generated magnetic field. A non-limiting approach includes means for acquiring at least one spatial distribution parameter of a magnetic resonance event associated with the affected in vivo magnetic resonance relaxation process, and means for generating a response based on an acquired at least one spatial distribution parameter. An aspect includes systems and devices including, among other things, circuitry for acquiring information associated with an in vivo magnetic resonance event generated by water molecule protons received in one or more voids 106 of a plurality of ferromagnetic microstructures configured to generate a static magnetic field within the void 106. An aspect includes systems and devices including, among other things, circuitry for generating a response based on acquiring information associated with an in vivo magnetic resonance event generated by water molecule protons received in one or more voids 106 of a plurality of ferromagnetic microstructures configured to generate a static magnetic field within the void 106. An aspect includes systems and devices including, among other things, circuitry for communicating the response to a user. An aspect includes systems and devices including, among other things, circuitry for generating an RF magnetic field of a character and for a sufficient time to excite at least some of the water molecule protons received in the one or more voids 106 of the plurality of ferromagnetic microstructures.

An aspect includes systems, devices, methods, and compositions for detecting regional information associated with a magnetic resonance event generated by in vivo target tissue-contained non-zero spin nuclei exposed to one or more voids 106 of a plurality of ferromagnetic microstructures configured to generate a static magnetic flux density within the void 106. A non-limiting approach includes systems, devices, methods, and compositions for affecting at least one of a proton transverse magnetic relaxation time or a proton longitudinal magnetic relaxation time associated with a biological sample by providing a plurality of ferromagnetic microstructures to at least a portion of the biological sample, at least some of the plurality of ferromagnetic microstructures including a first internal surface defining a void 106, the void 106 being selectively accessible to the biological sample, the plurality of ferromagnetic microstructures including a sufficient amount of at least one ferromagnetic material to generate a time-invariant magnetic field within the void 106, the time-invariant magnetic field of a sufficient character to affect at least one of a proton transverse magnetic relaxation time or a proton longitudinal magnetic relaxation time associated with the biological sample.

Figure 5A:
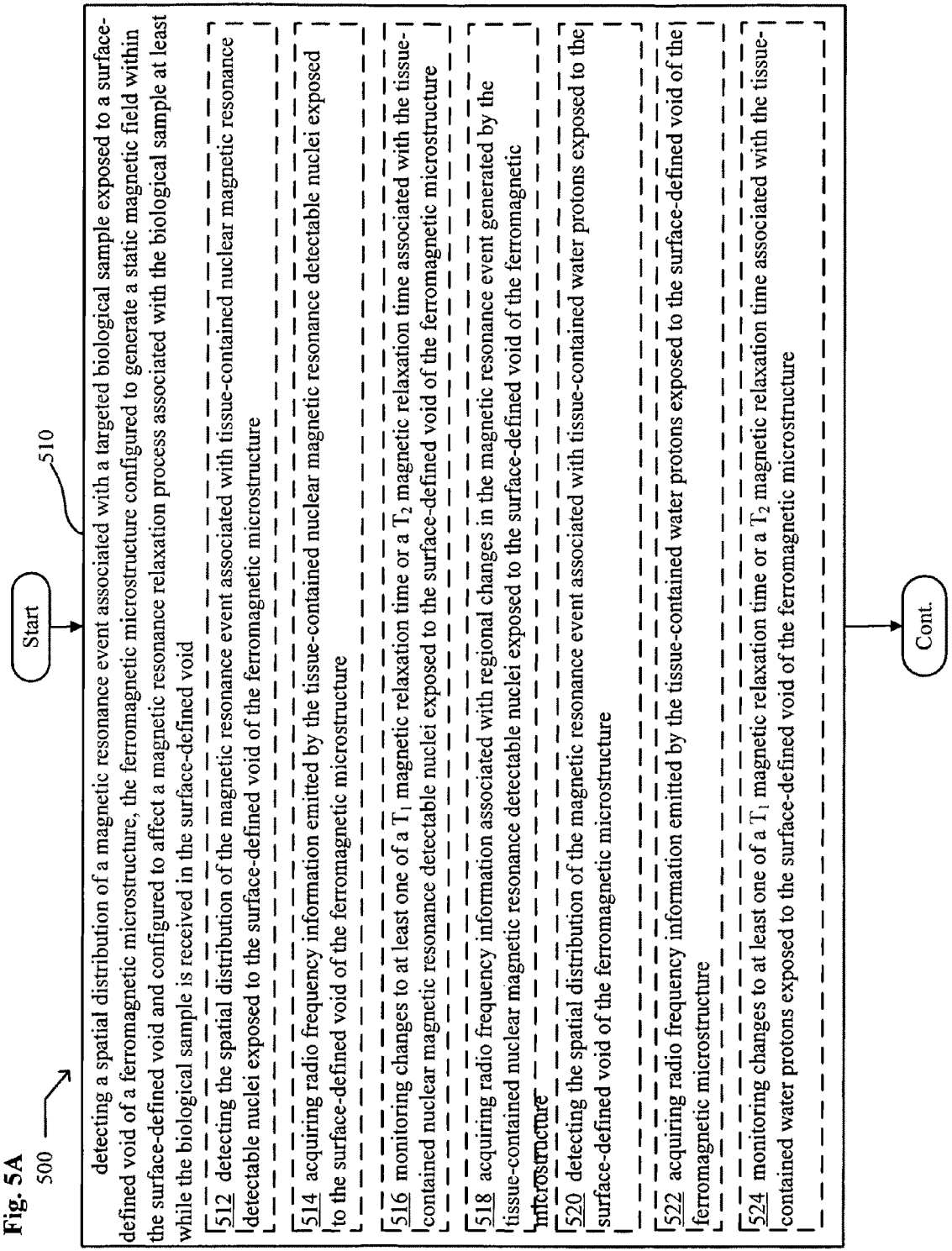
FIGS. 5A and 5B are flow diagrams of a method according to one illustrated embodiment.
Figure 5B:
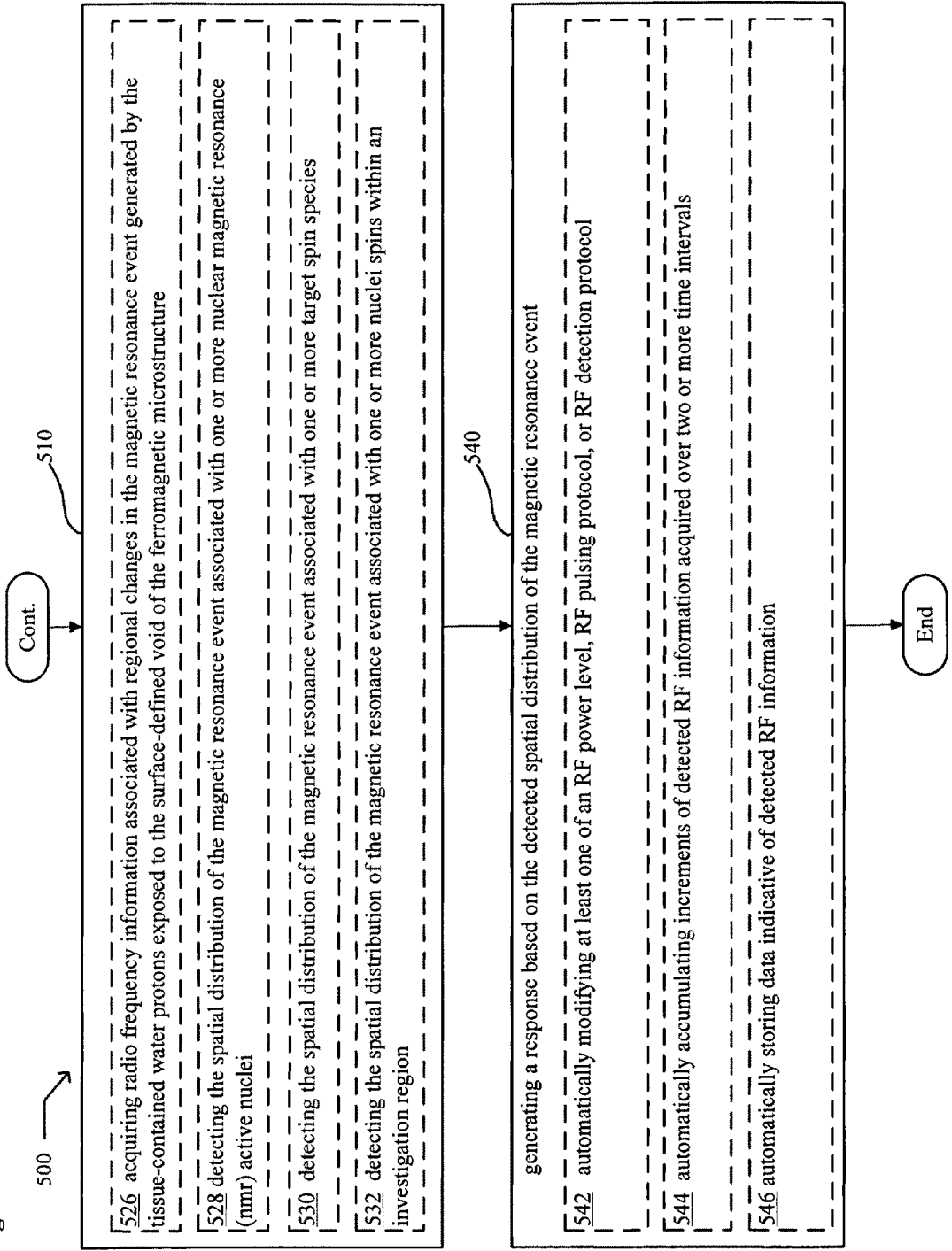

FIGS. 5A and 5b show an example of a method 500 for obtaining a non-external-magnet magnetic resonance image of a region within a biological subject. At 510, the method 500 includes detecting a spatial distribution of a magnetic resonance event associated with a targeted biological sample exposed to a surface-defined void 106 of a ferromagnetic microstructure, the ferromagnetic microstructure 102 configured to generate a static magnetic field within the surface-defined void 106 and configured to affect a magnetic resonance relaxation process associated with the biological sample at least while the biological sample is received in the surface-defined void 106. At 512, detecting the spatial distribution of a magnetic resonance event can include detecting the spatial distribution of the magnetic resonance event associated with tissue-contained nuclear magnetic resonance detectable nuclei exposed to the surface-defined void 106 of the ferromagnetic microstructure. At 514, detecting the spatial distribution of a magnetic resonance event can include acquiring RF information emitted by the tissue-contained nuclear magnetic resonance detectable nuclei exposed to the surface-defined void 106 of the ferromagnetic microstructure 102. At 516, detecting the spatial distribution of a magnetic resonance event can include monitoring changes to at least one of a $T_1$ magnetic relaxation time or a $T_2$ magnetic relaxation time associated with the tissue-contained nuclear magnetic resonance detectable nuclei exposed to the surface-defined void 106 of the ferromagnetic microstructure 102. At 518, detecting the spatial distribution of a magnetic resonance event can include acquiring RF information associated with regional changes in the magnetic resonance event generated by the tissue-contained nuclear magnetic resonance detectable nuclei exposed to the surface-defined void 106 of the ferromagnetic microstructure 102. At 520, detecting the spatial distribution of a magnetic resonance event can include detecting the spatial distribution of the magnetic resonance event associated with tissue-contained water protons exposed to the surface-defined void 106 of the ferromagnetic microstructure 102. At 522, detecting the spatial distribution of a magnetic resonance event can include acquiring RF information emitted by the tissue-contained water protons exposed to the surface-defined void 106 of the ferromagnetic microstructure. At 524, detecting the spatial distribution of a magnetic resonance event can include monitoring changes to at least one of a $T_1$ magnetic relaxation time or a $T_2$ magnetic relaxation time associated with the tissue-contained water protons exposed to the surface-defined void 106 of the ferromagnetic microstructure. At 526, detecting the spatial distribution of a magnetic resonance event can include acquiring RF information associated with regional changes in the magnetic resonance event generated by the tissue-contained water protons exposed to the surface-defined void 106 of the ferromagnetic microstructure. At 528, detecting the spatial distribution of a magnetic resonance event can include detecting the spatial distribution of the magnetic resonance event associated with one or more NMR active nuclei. At 530, detecting the spatial distribution of a magnetic resonance event can include detecting the spatial distribution of the magnetic resonance event associated with one or more target spin species. At 532, detecting the spatial distribution of a magnetic resonance event can include detecting the spatial distribution of the magnetic resonance event associated with one or more nuclei spins within an investigation region.

In an embodiment, detecting the spatial distribution of a magnetic resonance event associated with the targeted biological sample exposed to the surface-defined void 106 of the ferromagnetic microstructure 102 can include detecting the spatial distribution of a magnetic resonance event associated with the targeted biological sample exposed to the surface-defined void of selectively-targeted ferromagnetic microstructure. In an embodiment, detecting the spatial distribution of a magnetic resonance event associated with the targeted biological sample exposed to the surface-defined void 106 of the ferromagnetic microstructure 102 can include detecting the spatial distribution of a magnetic resonance event associated with the targeted biological sample exposed to a selectively-accessible surface-defined void of the ferromagnetic microstructure.

At 540, the method 500 includes generating a response based on the detected spatial distribution of the magnetic resonance event. At 542, generating the response can include automatically modifying at least one of an RF power level, an RF pulsing protocol, or an RF detection protocol. At 544, generating the response can include automatically accumulating increments of detected RF information acquired over two or more time intervals. At 546, generating the response can include automatically storing data indicative of detected RF information. In an embodiment, generating the response includes generating at least one of a display, a visual representation (e.g., a plot, a display, a spectrum, a visual depiction representative of the detected information, a visual depiction representative of a physical object (e.g., a ferromagnetic microstructure, a contrast agent, tissue, an indwelling implant, fat, muscle, bone, non-zero spin nuclei, a biological fluid component, or the like) a visual display, a visual display of at least one spectral parameter, and the like. In an embodiment, generating the response includes generating at least one of a visual representation, an audio representation (e.g., an alarm, an audio waveform representation of a magnetic resonance event, or the like), or a tactile representation (e.g., a tactile diagram, a tactile display, a tactile graph, a tactile interactive depiction, a tactile model (e.g., a multidimensional model of a physical object or a magnetic resonance event, or the like), a tactile pattern (e.g., a refreshable Braille display), a tactile-audio display, a tactile-audio graph, or the like). In an embodiment, generating the response includes generating an output, a response signal, a display, a data array, or a spectral plot. In an embodiment, generating the response includes generating one or more images associated with at least one of a spatial distribution of $T_1$ relaxation time information or a spatial distribution of $T_2$ relaxation time information. In an embodiment, generating the response includes generating at least one of a visual representation, an audio representation, or a tactile representation indicative of a parameter associated with one or more ferromagnetic microstructures. In an embodiment, generating the response includes generating at least one of a visual representation, an audio representation, or a tactile representation indicative of structure within a biological subject. In an embodiment, generating the response includes generating at least one of a visual representation, an audio representation, or a tactile representation indicative of a physical condition within a biological subject. In an embodiment, generating the response includes generating at least one of a visual representation, an audio representation, or a tactile representation indicative of a spatial distribution of plurality of ferromagnetic microstructures 102 within a biological subject. In an embodiment, generating the response includes generating at least one of a visual representation, an audio representation, or a tactile representation indicative of at least one of a spatial distribution of $T_1$ relaxation time information or a spatial distribution of $T_2$ relaxation time information.

Figure 6A:
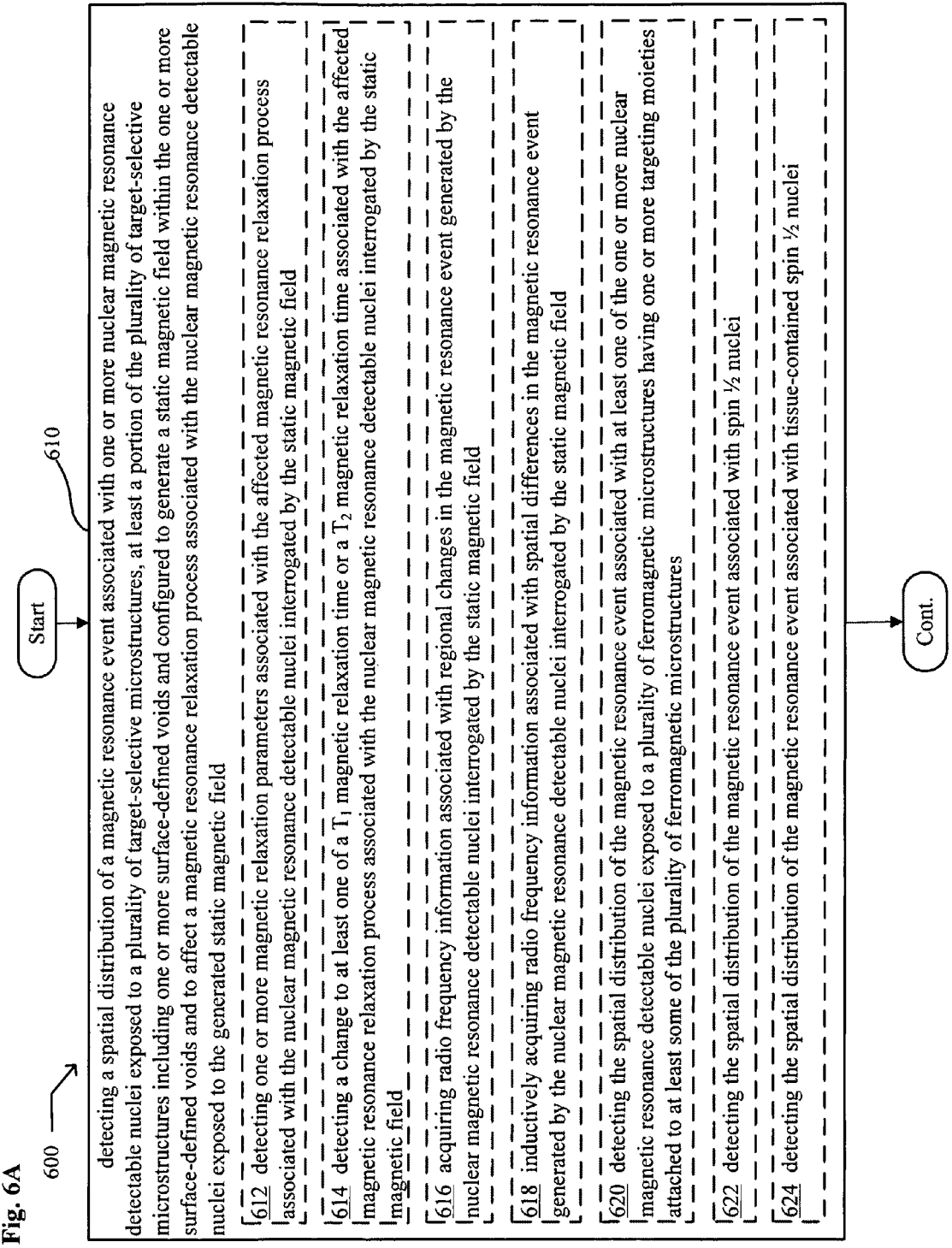
FIGS. 6A, 6B, and 6C are flow diagrams of a method according to one illustrated embodiment.
Figure 6B:
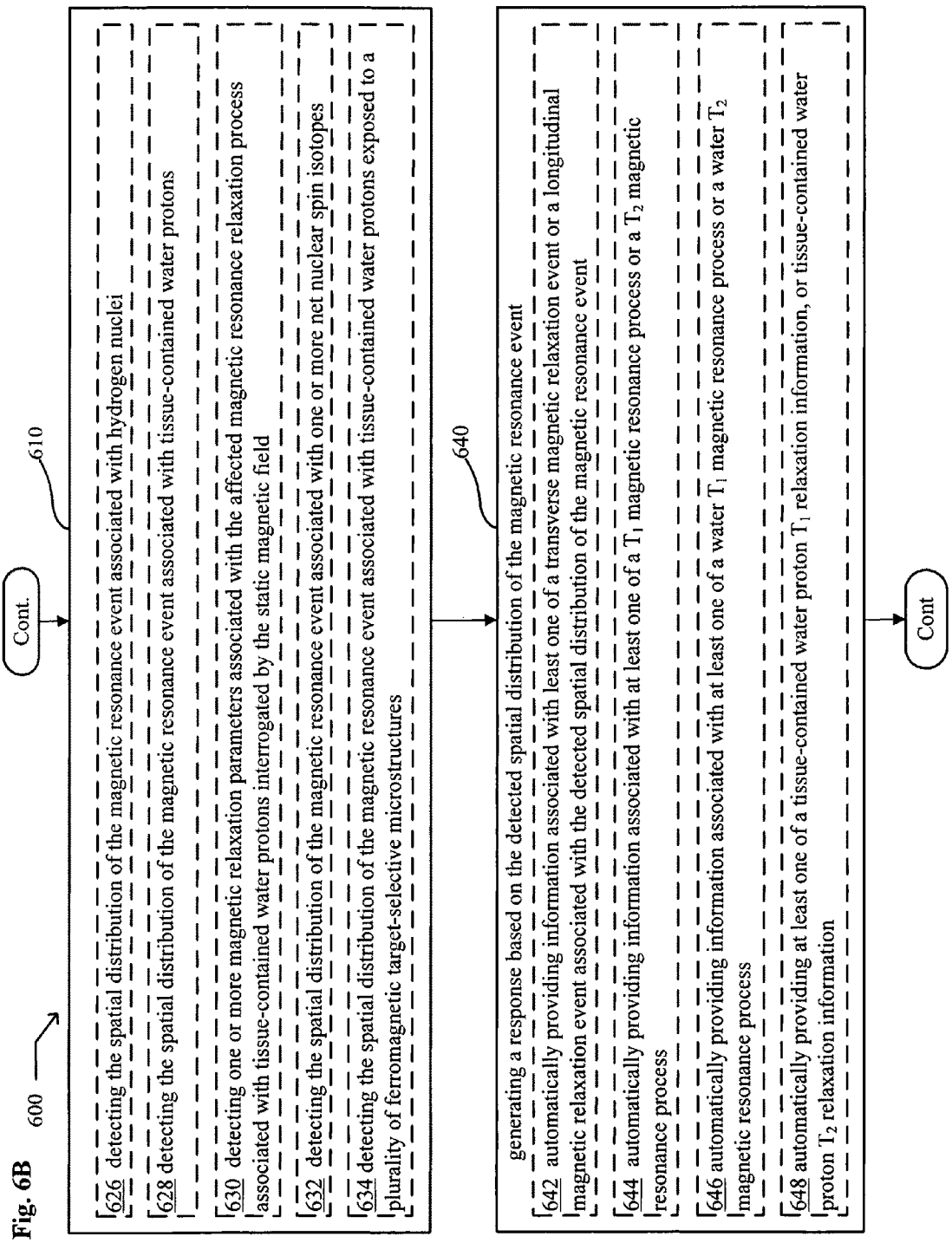
Figure 6C:
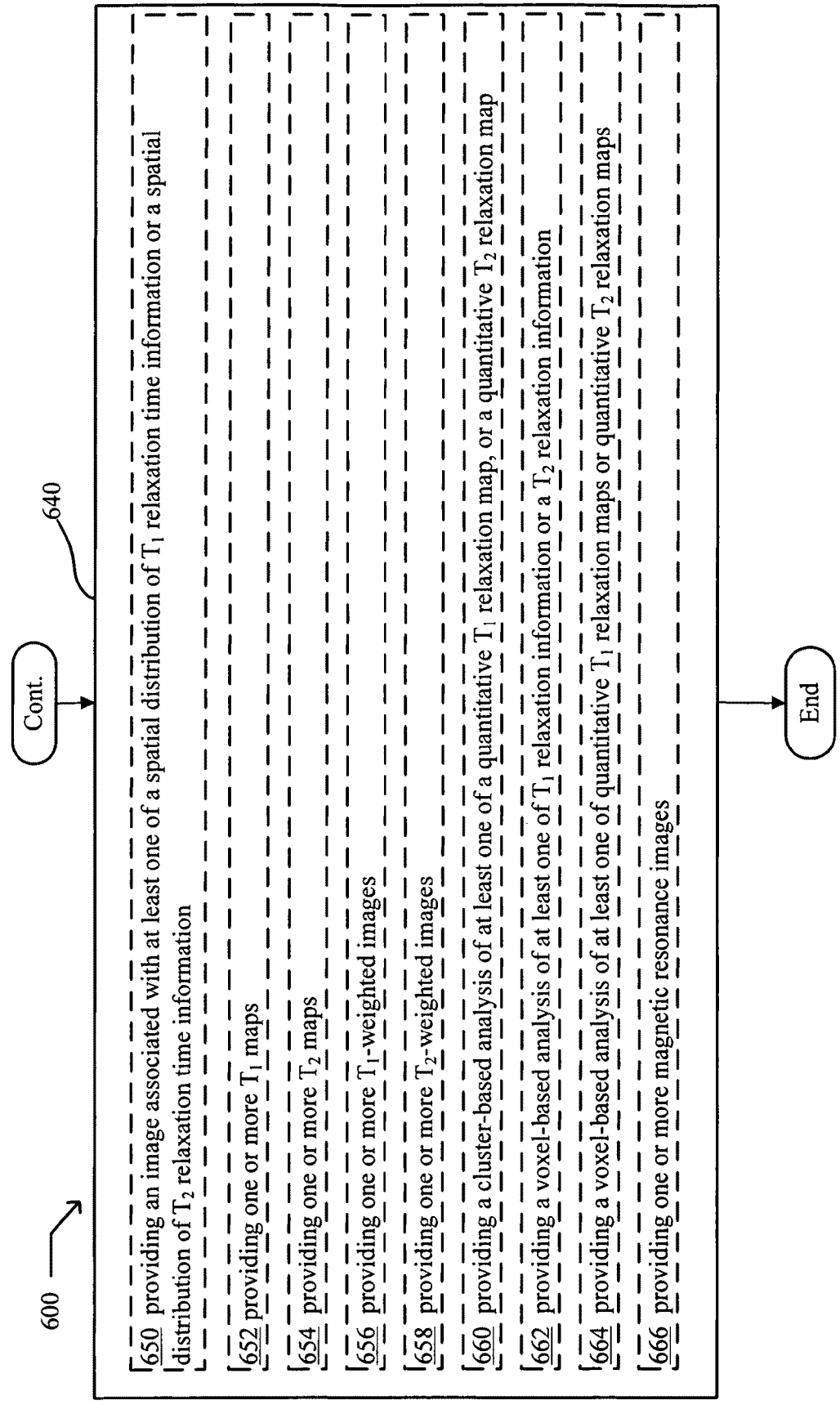

FIGS. 6A, 6B, and 6C show an example of a method 600 for obtaining a magnetic field resonance image. At 610, the method 600 includes detecting a spatial distribution of a magnetic resonance event associated with one or more nuclear magnetic resonance detectable nuclei exposed to a plurality of target-selective microstructures. In an embodiment, at least a portion of the plurality of target-selective microstructures include one or more surface-defined voids 106, and are configured to generate a static magnetic field within the one or more surface-defined voids 106 and to affect a magnetic resonance relaxation process associated with the nuclear magnetic resonance detectable nuclei exposed to the generated static magnetic field. At 612, detecting the spatial distribution of the magnetic resonance event can include detecting one or more magnetic relaxation parameters associated with the affected magnetic resonance relaxation process associated with the nuclear magnetic resonance detectable nuclei interrogated by the static magnetic field. At 614, detecting the spatial distribution of the magnetic resonance event can include detecting a change to at least one of a $T_1$ magnetic relaxation time or a $T_2$ magnetic relaxation time associated with the affected magnetic resonance relaxation process associated with the nuclear magnetic resonance detectable nuclei interrogated by the static magnetic field. At 616, detecting the spatial distribution of the magnetic resonance event can include acquiring RF information associated with regional changes in the magnetic resonance event generated by the nuclear magnetic resonance detectable nuclei interrogated by the static magnetic field. At 618, detecting the spatial distribution of the magnetic resonance event can include inductively acquiring RF information associated with spatial differences in the magnetic resonance event generated by the nuclear magnetic resonance detectable nuclei interrogated by the static magnetic field. At 620, detecting the spatial distribution of the magnetic resonance event can include detecting the spatial distribution of the magnetic resonance event associated with at least one of the one or more nuclear magnetic resonance detectable nuclei exposed to a plurality of target-selective microstructures having one or more targeting moieties 112 attached to one or more of the plurality of target-selective microstructures. At 622, detecting the spatial distribution of the magnetic resonance event includes detecting the spatial distribution of the magnetic resonance event associated with spin ½ nuclei. At 624, detecting the spatial distribution of the magnetic resonance event includes detecting the spatial distribution of the magnetic resonance event associated with tissue-contained spin ½ nuclei. At 626, detecting the spatial distribution of the magnetic resonance includes detecting the spatial distribution of the magnetic resonance event associated with hydrogen nuclei. At 628, detecting the spatial distribution of the magnetic resonance event includes detecting the spatial distribution of the magnetic resonance event associated with tissue-contained water protons. At 630, detecting the spatial distribution of the magnetic resonance event includes detecting one or more magnetic relaxation parameters associated with the affected magnetic resonance relaxation process associated with tissue-contained water protons interrogated by the static magnetic field. At 632, detecting the spatial distribution of the magnetic resonance event includes detecting the spatial distribution of the magnetic resonance event associated with one or more net nuclear spin isotopes. At 634, detecting the spatial distribution of the magnetic resonance event includes detecting the spatial distribution of the magnetic resonance event associated with tissue-contained water protons exposed to a plurality of ferromagnetic target-selective microstructures. In an embodiment, detecting the spatial distribution of the magnetic resonance event can include detecting a spatial distribution of a magnetic resonance event associated with one or more nuclear magnetic resonance detectable nuclei exposed to a plurality of selectively-accessible, target-selective, microstructures. In an embodiment, at least a portion of the plurality of target-selective microstructures include one or more components that selectively allow nuclear magnetic resonance detectable nuclei to access the one or more surface-defined voids. In an embodiment, detecting the spatial distribution of the magnetic resonance event can include detecting a spatial distribution of a magnetic resonance event associated with one or more nuclear magnetic resonance detectable nuclei exposed to a plurality of target-selective microstructures including one or more targeting moieties attached thereof.

At 640, the method 600 includes providing a response based on the detected spatial distribution of the magnetic resonance event. At 642, providing the response includes automatically providing information associated with least one of a transverse magnetic relaxation event or a longitudinal magnetic relaxation event associated with the detected spatial distribution of the magnetic resonance event. At 644, providing the response includes automatically providing information associated with at least one of a $T_1$ magnetic resonance process or a $T_2$ magnetic resonance process. At 646, providing the response includes automatically providing information associated with at least one of a water $T_1$ magnetic resonance process or a water $T_2$ magnetic resonance process. At 648, providing the response includes automatically providing at least one of a tissue-contained water proton $T_1$ relaxation information, or tissue-contained water proton $T_2$ relaxation information. At 650, providing the response includes providing an image associated with at least one of a spatial distribution of $T_1$ relaxation time information or a spatial distribution of $T_2$ relaxation time information. At 652, providing the response includes providing one or more $T_1$ maps. At 654, providing the response includes providing one or more $T_2$ maps. At 656, providing the response includes providing one or more $T_1$-weighted images. See, e.g., U.S. Pat. No. 7,276,904 (issued Oct. 2, 2007) (the contents of which are incorporated herein by reference). At 658, providing the response includes providing one or more $T_2$-weighted images. At 660, providing the response includes providing a cluster-based analysis of at least one of a quantitative $T_1$ relaxation map, or a quantitative $T_2$ relaxation map. At 662, providing the response includes providing a voxel-based analysis of at least one of $T_1$ relaxation information or a $T_2$ relaxation information. At 664, providing the response includes providing a voxel-based analysis of at least one of quantitative $T_1$ relaxation maps or quantitative $T_2$ relaxation maps. At 666, providing the response includes providing one or more magnetic resonance images.

Figure 7:
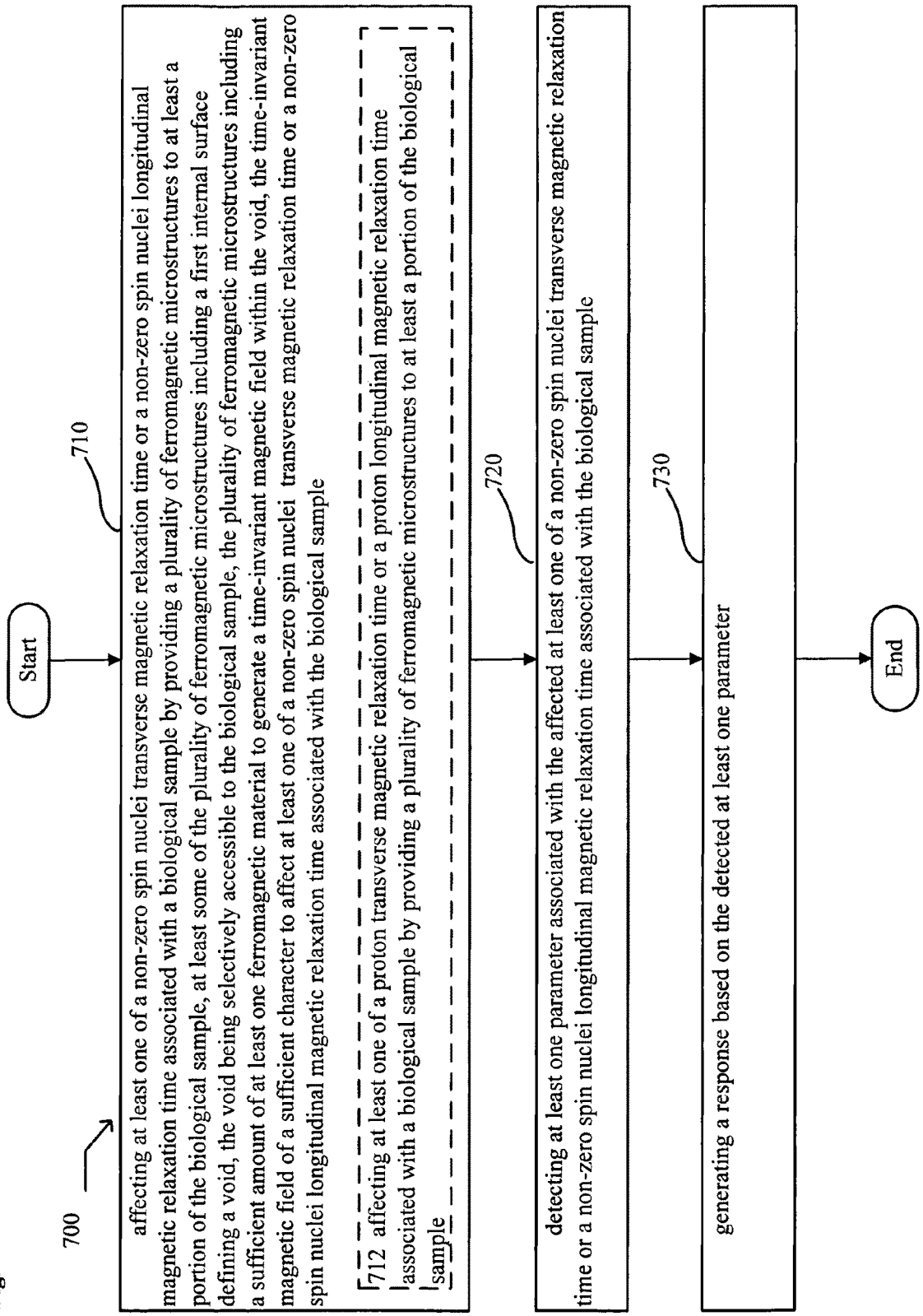
FIG. 7 is a flow diagram of a method according to one illustrated embodiment.

FIG. 7 shows an example of a multiplex imaging method 700. At 710, the method 700 includes affecting at least one of a non-zero spin nuclei transverse magnetic relaxation time or a non-zero spin nuclei longitudinal magnetic relaxation time associated with a biological sample by providing a plurality of ferromagnetic microstructures to at least a portion of the biological sample, at least some of the plurality of ferromagnetic microstructures 102 including a first internal surface defining a void, the void being selectively accessible to the biological sample, the plurality of ferromagnetic microstructures including a sufficient amount of at least one ferromagnetic material to generate a time-invariant magnetic field within the void, the time-invariant magnetic field of a sufficient character to affect at least one of a non-zero spin nuclei transverse magnetic relaxation time or a non-zero spin nuclei longitudinal magnetic relaxation time associated with the biological sample. In an embodiment, the plurality of ferromagnetic microstructures 102 includes one or more ferromagnetic microstructure sets. In an embodiment, each ferromagnetic microstructure set includes one or more ferromagnetic microstructures 102 configured to include an accessible internal void 106 and configured to generate a characteristic time-invariant magnetic field 108 within the accessible internal void 106. In an embodiment, one or more of the ferromagnetic microstructure sets include a different characteristic time-invariant magnetic field 108. At 720, the method 700 includes detecting at least one parameter associated with the affected at least one of a non-zero spin nuclei transverse magnetic relaxation time or a non-zero spin nuclei longitudinal magnetic relaxation time associated with the biological sample. At 730, the method 700 includes generating a response based on the detected at least one parameter.

Figure 8:
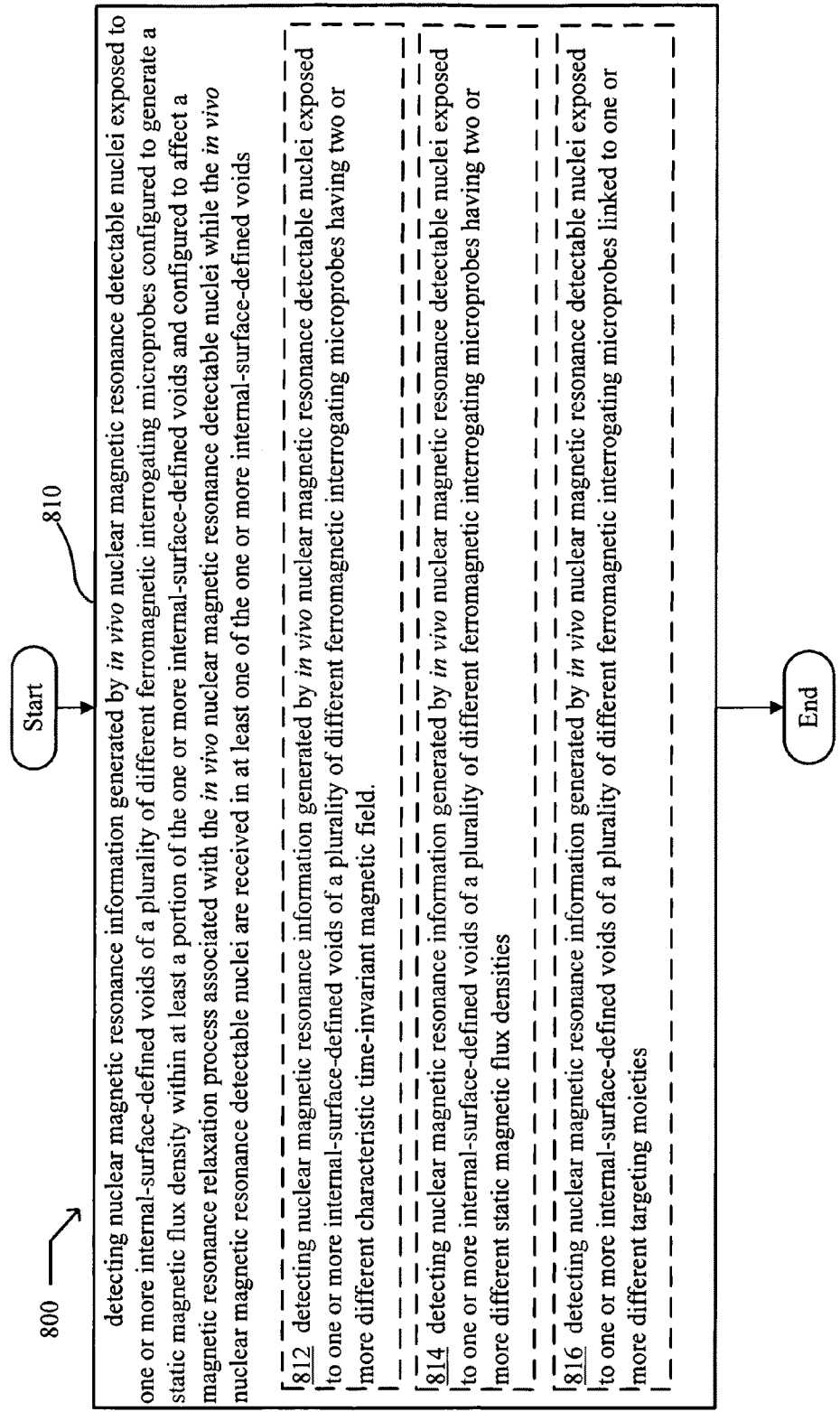
FIG. 8 is a flow diagram of a method according to one illustrated embodiment.

FIG. 8 shows an example of a method 800 of multiplex interrogation of a biological sample. At 810, the method 800 includes detecting nuclear magnetic resonance information generated by in vivo nuclear magnetic resonance detectable nuclei exposed to one or more internal-surface-defined voids 106 of a plurality of different ferromagnetic microstructures configured to generate a static magnetic flux density within at least a portion of the one or more internal-surface-defined voids 106 and configured to affect a magnetic resonance relaxation process associated with the in vivo nuclear magnetic resonance detectable nuclei while the in vivo nuclear magnetic resonance detectable nuclei are received in at least one of the one or more internal-surface-defined voids. At 812, detecting the nuclear magnetic resonance information generated by in vivo nuclear magnetic resonance detectable nuclei exposed to one or more internal-surface-defined voids 106 of a plurality of different ferromagnetic microstructures includes detecting nuclear magnetic resonance information generated by in vivo nuclear magnetic resonance detectable nuclei exposed to one or more internal-surface-defined voids 106 of a plurality of different ferromagnetic microstructures having two or more different characteristic time-invariant magnetic field 108. At 814, detecting the nuclear magnetic resonance information generated by in vivo nuclear magnetic resonance detectable nuclei exposed to one or more internal-surface-defined voids 106 of a plurality of different ferromagnetic microstructures includes detecting nuclear magnetic resonance information generated by in vivo nuclear magnetic resonance detectable nuclei exposed to one or more internal-surface-defined voids 106 of a plurality of different ferromagnetic microstructures having two or more different static magnetic flux densities. At 816, detecting the nuclear magnetic resonance information generated by in vivo nuclear magnetic resonance detectable nuclei exposed to one or more internal-surface-defined voids 106 of a plurality of different ferromagnetic microstructures includes detecting nuclear magnetic resonance information generated by in vivo nuclear magnetic resonance detectable nuclei exposed to one or more internal-surface-defined voids 106 of a plurality of different ferromagnetic microstructures linked to one or more different targeting moieties.

Figure 9:
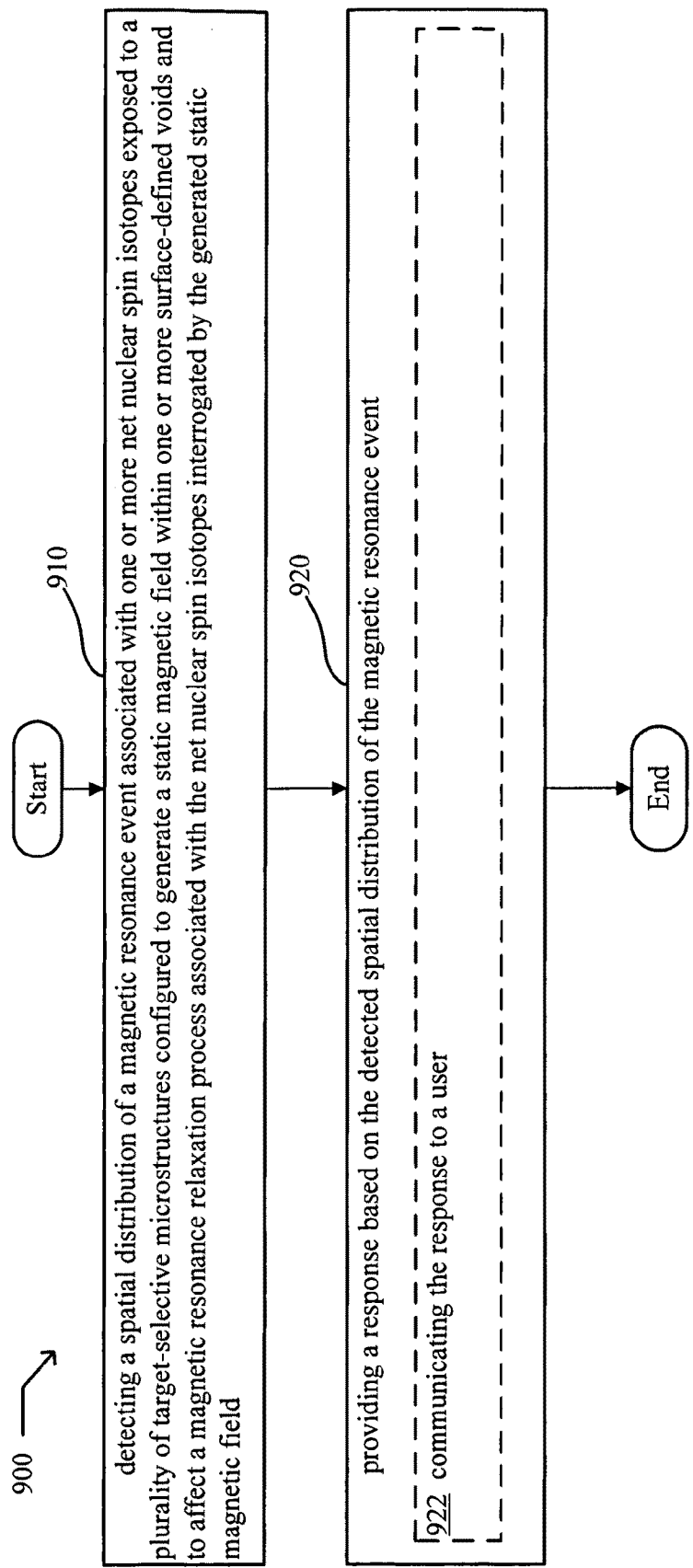
FIG. 9 is a flow diagram of a method according to one illustrated embodiment.

FIG. 9 shows an example of a method 900 for obtaining a non-external magnetic field resonance image of a region within a biological subject. At 910, the method 900 includes detecting a spatial distribution of a magnetic resonance event associated with one or more net nuclear spin isotopes exposed to a plurality of target-selective microstructures configured to generate a static magnetic field within one or more surface-defined voids 106 and to affect a magnetic resonance relaxation process associated with the net nuclear spin isotopes interrogated by the generated static magnetic field. At 920, the method 900 may further include providing a response based on the detected spatial distribution of the magnetic resonance event. At 922, providing the response can include communicating the response to a user.

Figure 10:
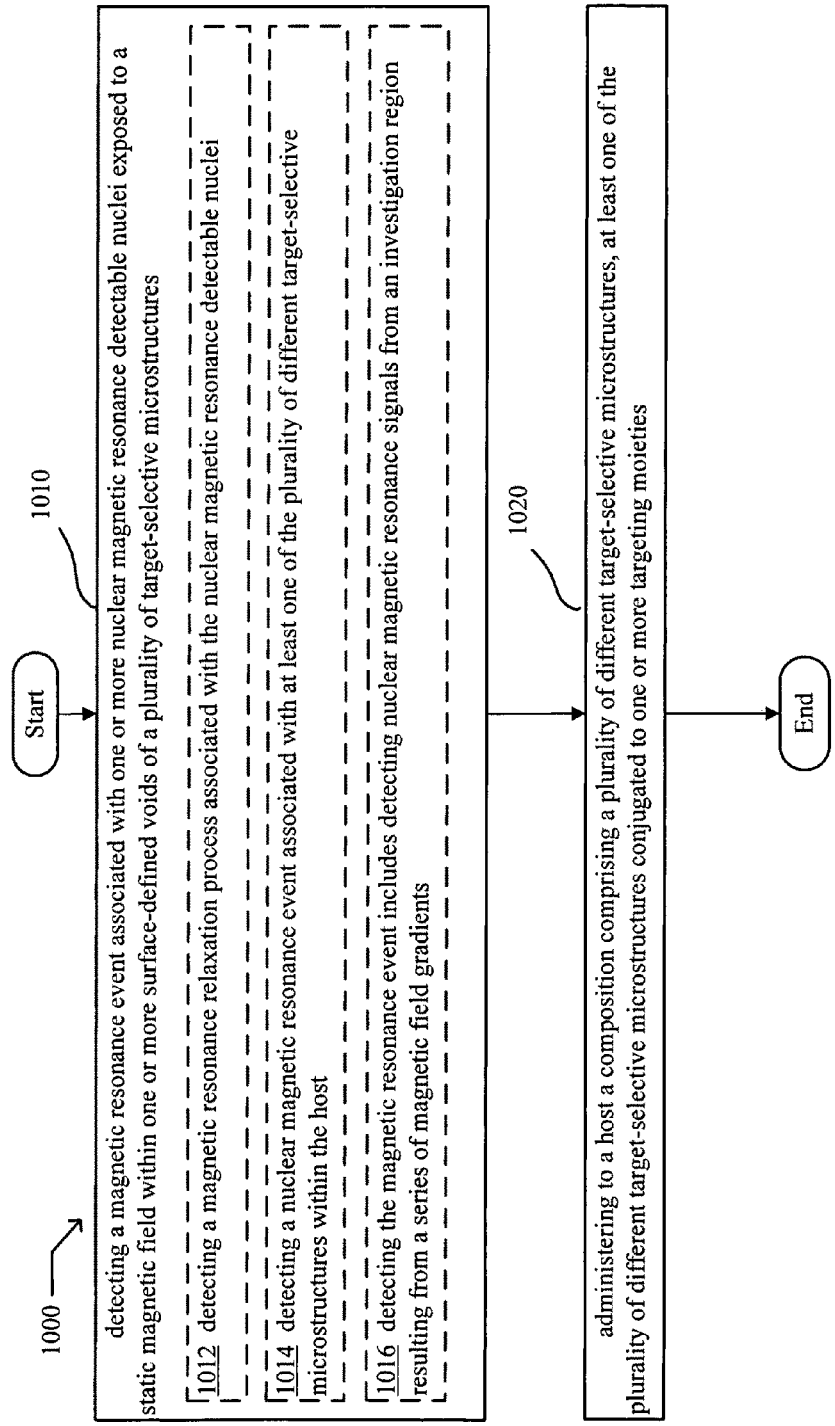
FIG. 10 is a flow diagram of a method according to one illustrated embodiment.
Figure 11:
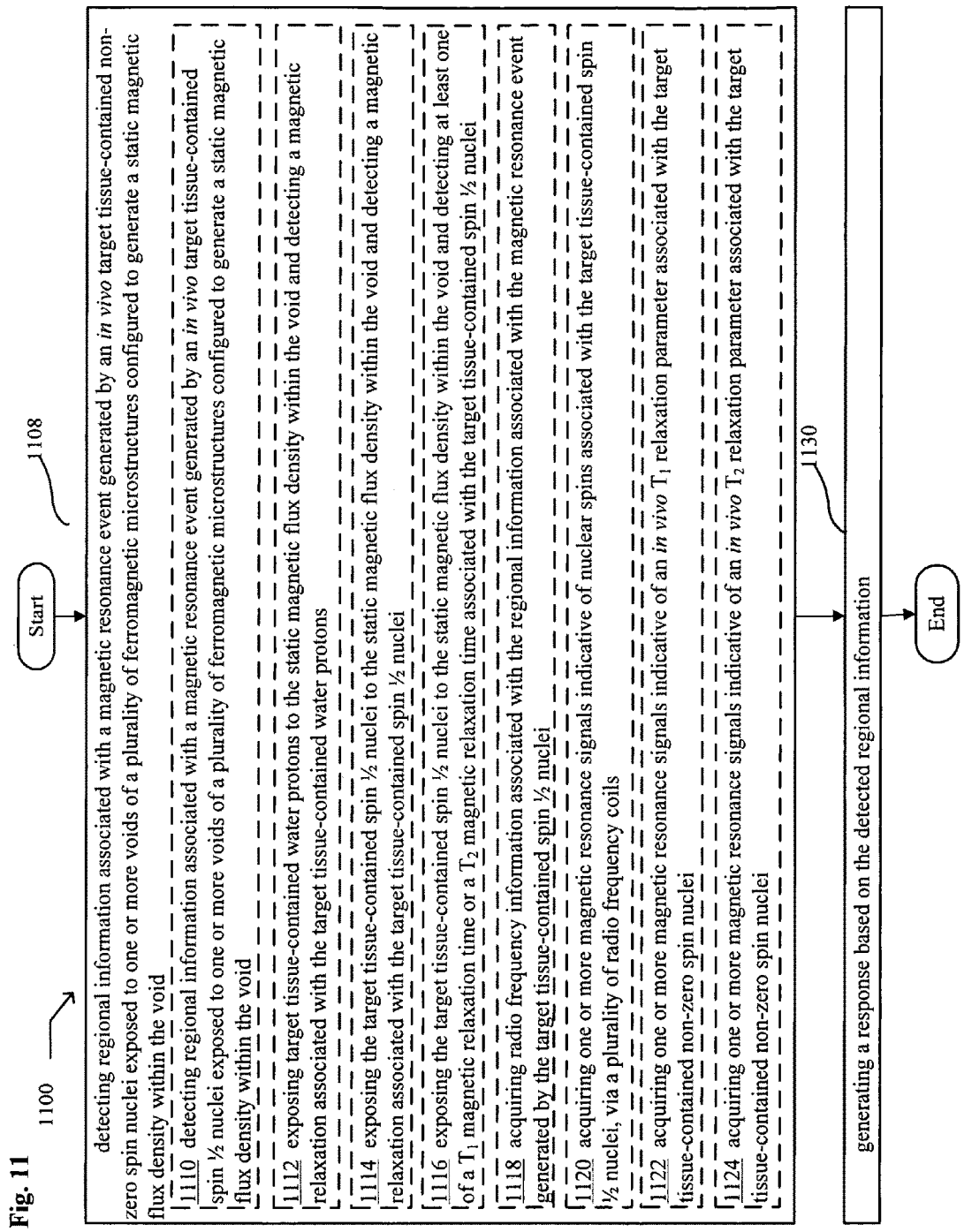
FIG. 11 is a flow diagram of a method according to one illustrated embodiment.

FIG. 10 shows an example of a method 1000. At 1010, the method 1000 includes detecting a magnetic resonance event associated with one or more nuclear magnetic resonance detectable nuclei exposed to a static magnetic field within one or more surface-defined voids 106 of a plurality of target-selective microstructures. At 1012, detecting magnetic resonance event can include detecting a magnetic resonance relaxation process associated with the nuclear magnetic resonance detectable nuclei. At 1014, detecting the magnetic resonance event can include detecting a nuclear magnetic resonance event associated with at least one of the plurality of different target-selective microstructures within the host. At 1016, detecting the magnetic resonance event includes detecting nuclear magnetic resonance signals from an investigation region resulting from a series of magnetic field gradients. At 1020, the method 1000 may further include administering to a host a composition comprising a plurality of different target-selective microstructures, at least one of the plurality of different target-selective microstructures conjugated to one or more targeting moieties.

At 1110, detecting the regional information associated with the magnetic resonance event includes detecting regional information associated with a magnetic resonance event generated by in vivo target tissue-contained spin ½ nuclei exposed to one or more voids 106 of a plurality of ferromagnetic microstructures configured to generate a static magnetic flux density within the void 106.

At 1110, detecting the regional information associated with the magnetic resonance event includes detecting regional information associated with a magnetic resonance event generated by in vivo target tissue-contained spin ½ nuclei exposed to one or more voids 106 of a plurality of ferromagnetic microstructures c configured to generate a static magnetic flux density within the void 106.

At 1112, detecting the regional information associated with the magnetic resonance event includes exposing target tissue-contained water protons to the static magnetic flux density within the void 106 and detecting a magnetic relaxation associated with the target tissue-contained water protons. At 1114, detecting the regional information associated with the magnetic resonance event includes exposing the target tissue-contained spin ½ nuclei to the static magnetic flux density within the void 106 and detecting a magnetic relaxation associated with the target tissue-contained spin ½ nuclei. At 1116, detecting the regional information associated with the magnetic resonance event includes exposing the target tissue-contained spin ½ nuclei to the static magnetic flux density within the void 106 and detecting at least one of a $T_1$ magnetic relaxation time or a $T_2$ magnetic relaxation time associated with the target tissue-contained spin ½ nuclei. At 1118, detecting the regional information associated with the magnetic resonance event includes acquiring RF information associated with the regional information associated with the magnetic resonance event generated by the target tissue-contained spin ½ nuclei. At 1120, detecting the regional information associated with the magnetic resonance event includes acquiring one or more magnetic resonance signals indicative of nuclear spins associated with the target tissue-contained spin ½ nuclei, via a plurality of RF coils. At 1122, detecting the regional information associated with the magnetic resonance event includes acquiring one or more magnetic resonance signals indicative of an in vivo $T_1$ relaxation parameter associated with the target tissue-contained spin ½ nuclei. At 1124, detecting the regional information associated with the magnetic resonance event includes acquiring one or more magnetic resonance signals indicative of an in vivo $T_2$ relaxation parameter associated with the target tissue-contained spin ½ nuclei. At 1130, the method 1100 includes generating a response based on the detected regional information.

Figure 12:
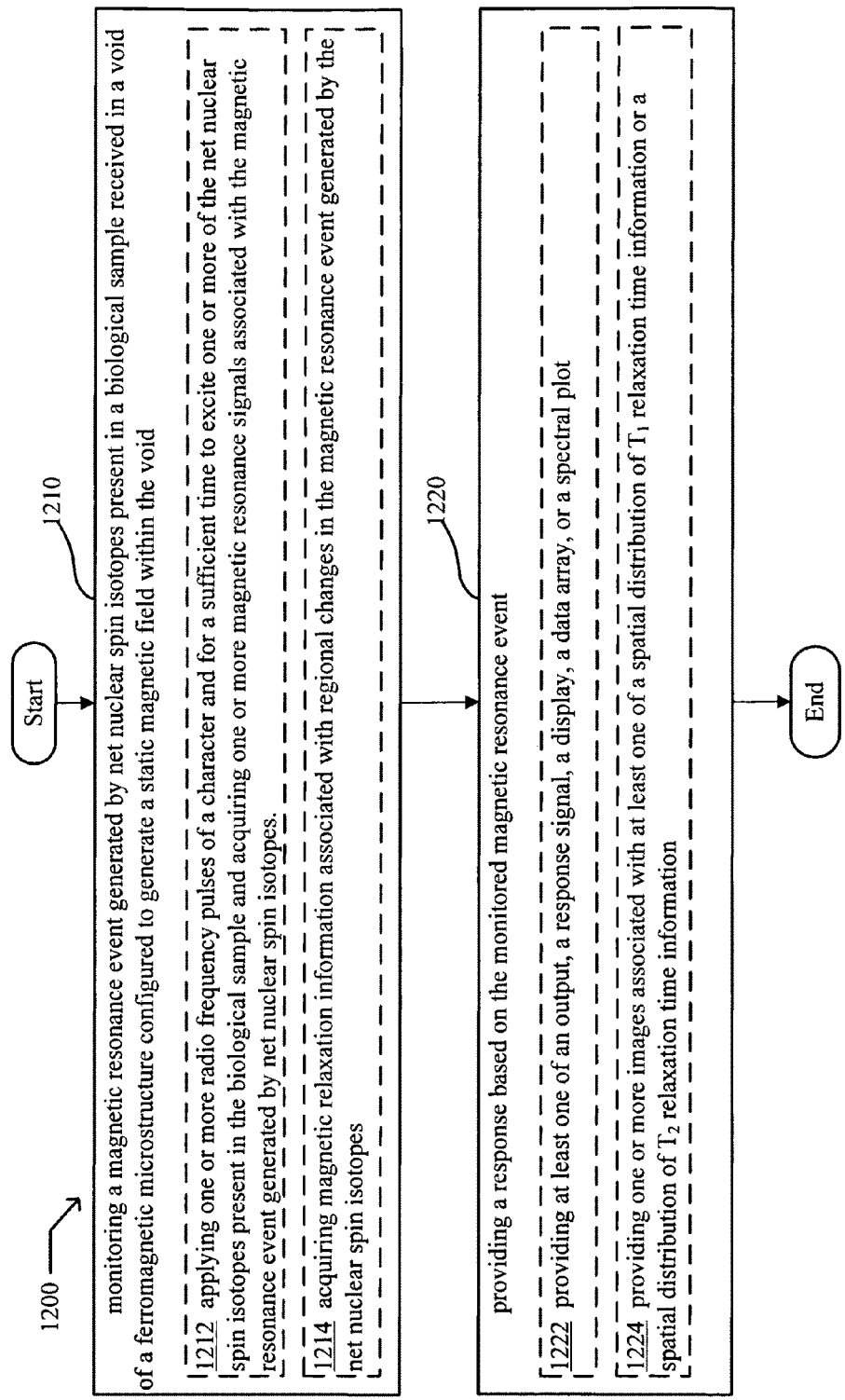
FIG. 12 is a flow diagram of a method according to one illustrated embodiment.

FIG. 12 shows an example of a method 1200 for obtaining a magnetic resonance image of a region within a biological subject in absence of an externally generated magnetic field. At 1210, the method 1200 includes monitoring a magnetic resonance event generated by net nuclear spin isotopes present in a biological sample received in a void 106 of a ferromagnetic microstructure configured to generate a static magnetic field within the void 106. At 1212, monitoring the magnetic resonance event includes applying one or more RF pulses of a character and for a sufficient time to excite one or more of the net nuclear spin isotopes present in the biological sample and acquiring one or more magnetic resonance signals associated with the magnetic resonance event generated by net nuclear spin isotopes. At 1214, monitoring the magnetic resonance event includes acquiring magnetic relaxation information associated with regional changes in the magnetic resonance event generated by the net nuclear spin isotopes. At 1220, the method 1200 includes providing a response based on the monitored magnetic resonance event. At 1222, providing a response includes providing at least one of an output, a response signal, a display, a data array, or a spectral plot. At 1224, providing a response include providing one or more images associated with at least one of a spatial distribution of $T_1$ relaxation time information or a spatial distribution of $T_2$ relaxation time information.

Figure 13:
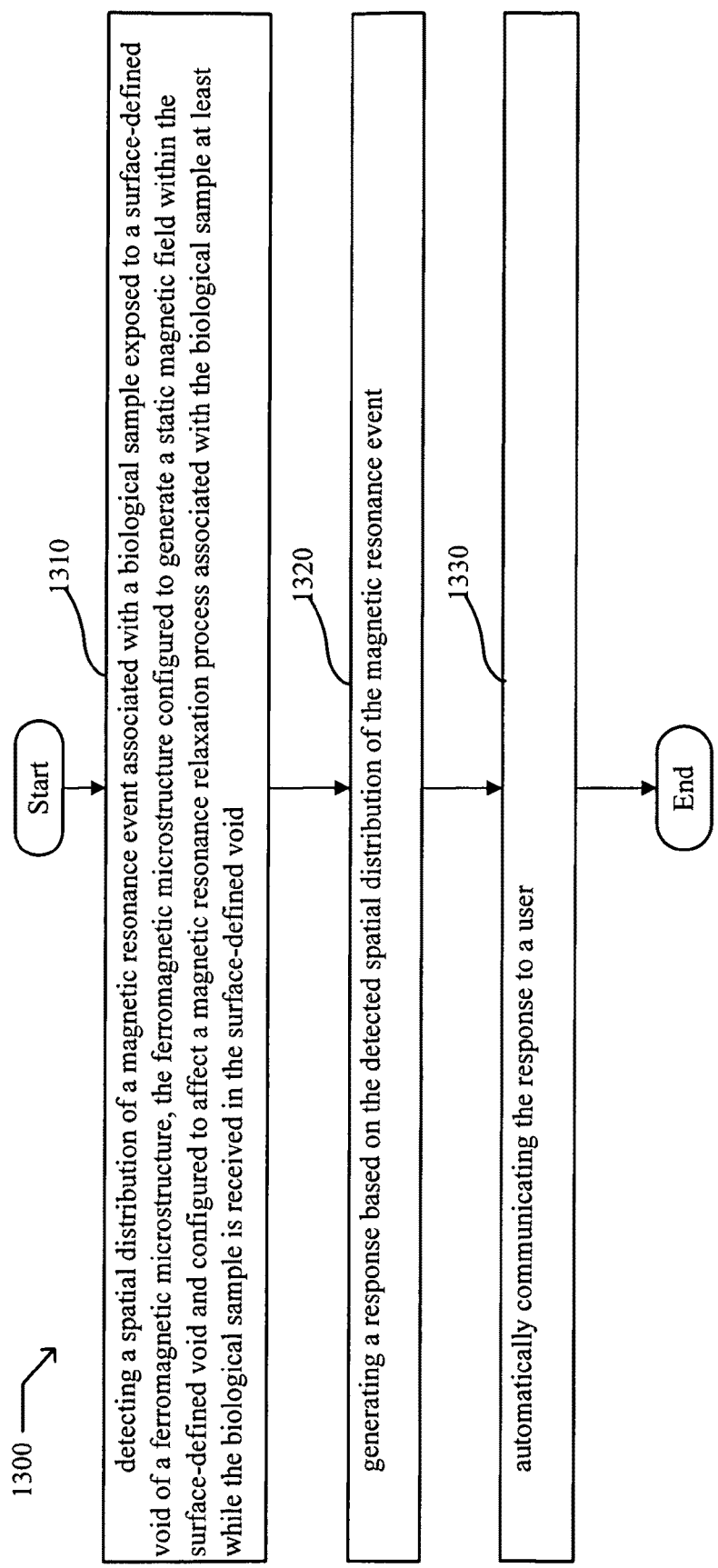
FIG. 13 is a flow diagram of a method according to one illustrated embodiment.

In an embodiment, a computer program product includes one or more signal-bearing media containing computer instructions which, when run on a computing device, cause the computing device to implement a method 1300. As shows in FIG. 13, at 1310, the method 1300 includes detecting a spatial distribution of a magnetic resonance event associated with a biological sample exposed to a surface-defined void 106 of a ferromagnetic microstructure, the ferromagnetic microstructure configured to generate a static magnetic field within the surface-defined void 106 and configured to affect a magnetic resonance relaxation process associated with the biological sample at least while the biological sample is received in the surface-defined void 106. At 1320, the method 1300 includes generating a response based on the detected spatial distribution of the magnetic resonance event. At 1330, the method 1300 includes automatically communicating the response to a user.

Figure 14:
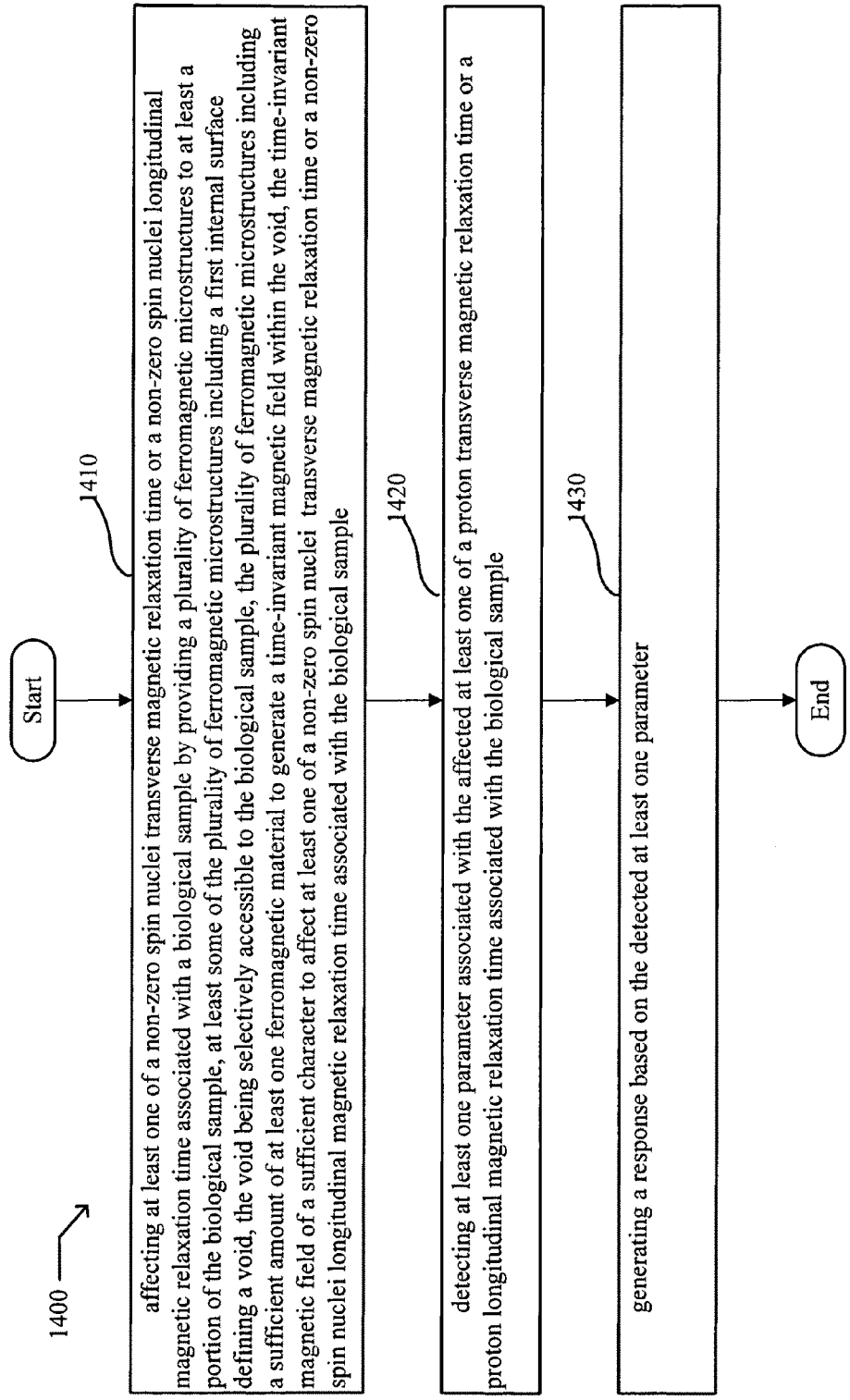
FIG. 14 is a flow diagram of a method according to one illustrated embodiment.
Figure 15B:
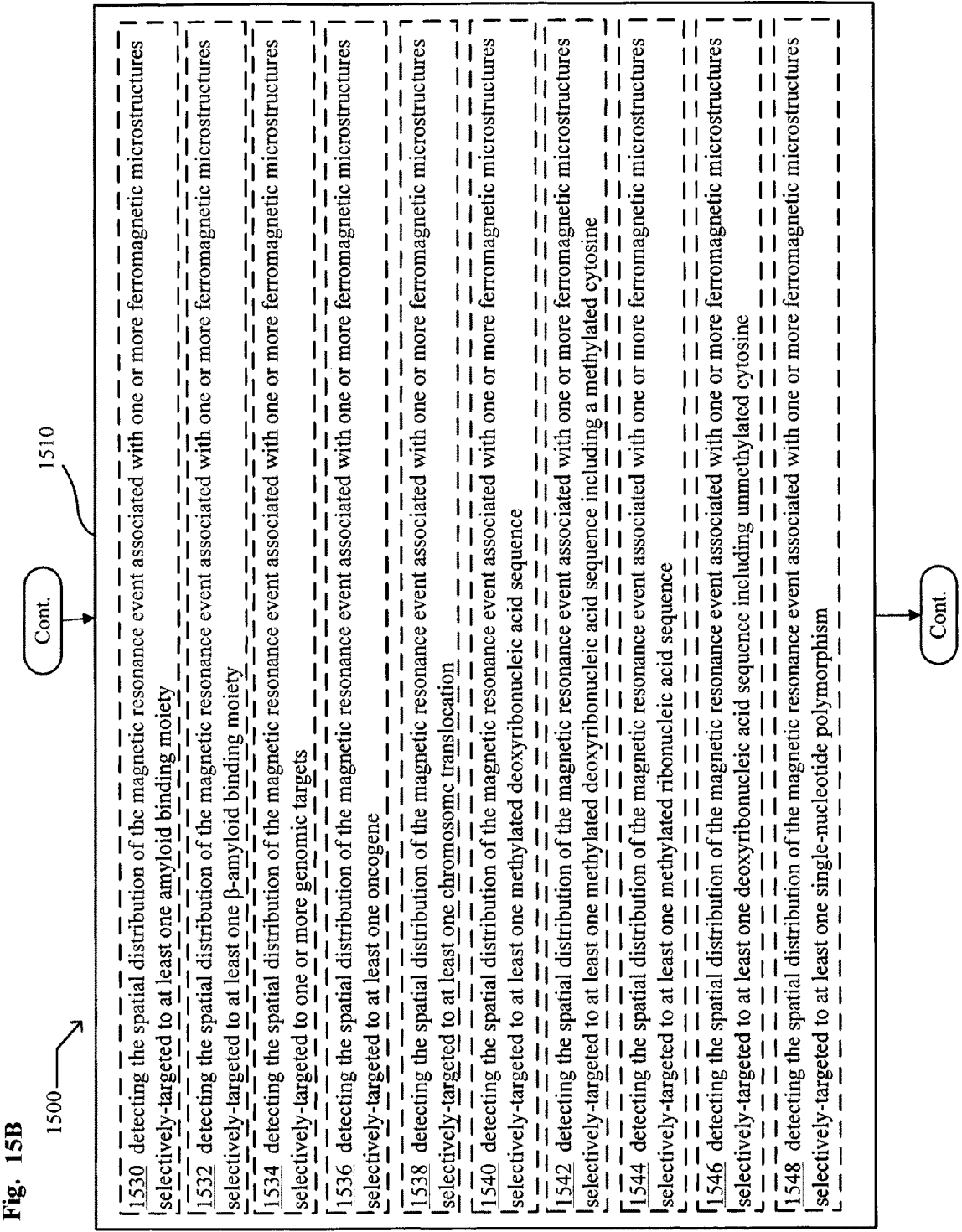
Figure 15C:
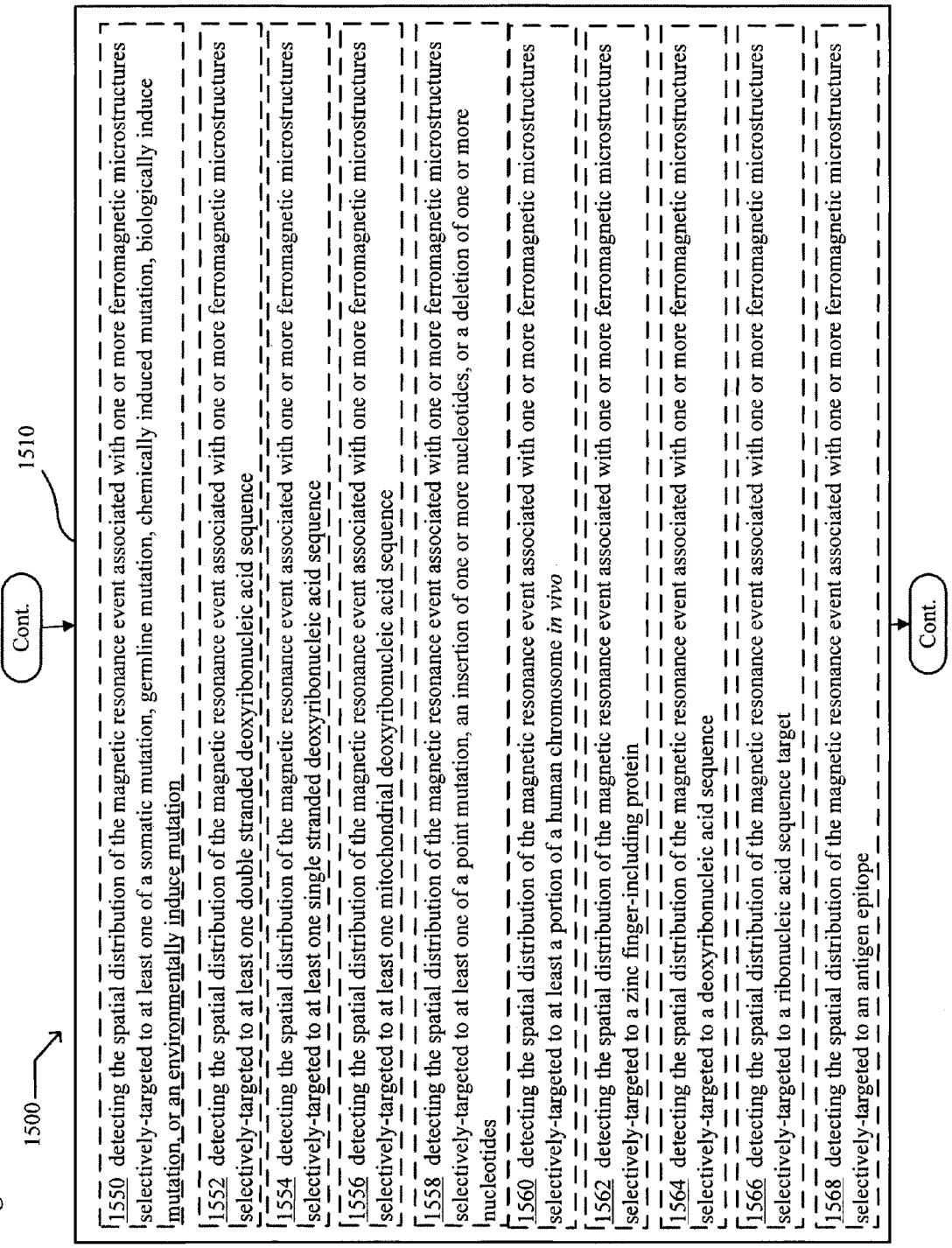
Figure 15D:
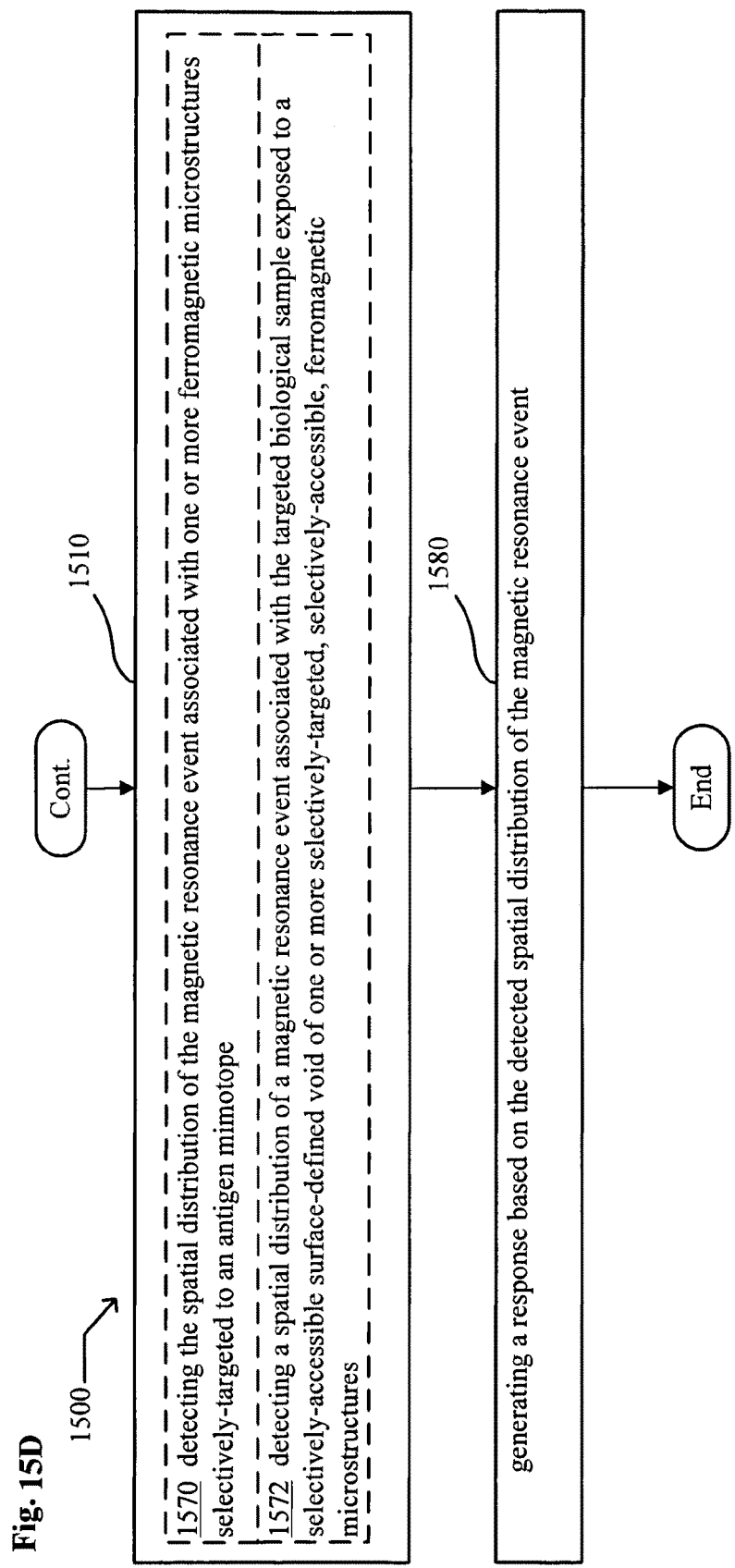

FIG. 14 shows an example of a method 1400. At 1410, the method 1400 includes affecting at least one of a non-zero spin nuclei transverse magnetic relaxation time or a non-zero spin nuclei longitudinal magnetic relaxation time associated with a biological sample by providing a plurality of ferromagnetic microstructures to at least a portion of the biological sample, one or more of the plurality of ferromagnetic microstructures including a first internal surface 104 defining a void 106, the void 106 being selectively accessible to the biological sample, the plurality of ferromagnetic microstructures including a sufficient amount of at least one ferromagnetic material to generate a time-invariant magnetic field 108 within the void 106, the time-invariant magnetic field 108 of a sufficient character to affect at least one of a non-zero spin nuclei transverse magnetic relaxation time or a non-zero spin nuclei longitudinal magnetic relaxation time associated with the biological sample of a sufficient character to affect at least one of a non-zero spin nuclei transverse magnetic relaxation time or a non-zero spin nuclei longitudinal magnetic relaxation time associated with the biological sample of a sufficient character to affect at least one of a non-zero spin nuclei transverse magnetic relaxation time or a non-zero spin nuclei longitudinal magnetic relaxation time associated with the biological sample of a sufficient character to affect at least one of a non-zero spin nuclei transverse magnetic relaxation time or a non-zero spin nuclei longitudinal magnetic relaxation time associated with the biological sample. At 1420, the method 1400 may further include detecting at least one parameter associated with the affected at least one of a proton transverse magnetic relaxation time or a proton longitudinal magnetic relaxation time associated with the biological sample. At 1430, the method 1400 may further include generating a response based on the detected at least one parameter.

FIGS. 15A through 15D show an example of a method 1500. At 1510, the method 1500 includes detecting a spatial distribution of a magnetic resonance event associated with a targeted biological sample exposed to a surface-defined void of one or more selectively-targeted ferromagnetic microstructures, the one or more selectively-targeted ferromagnetic microstructures configured to generate a static magnetic field within the surface-defined void and configured to affect a magnetic resonance relaxation process associated with the biological sample at least while the biological sample is received in the surface-defined void. At 1512, detecting the spatial distribution of the magnetic resonance event includes detecting the spatial distribution of the magnetic resonance event associated with one or more ferromagnetic microstructures selectively-targeted to at least one cell surface receptor targeting moiety. At 1514, detecting the spatial distribution of the magnetic resonance event includes detecting the spatial distribution of the magnetic resonance event associated with one or more ferromagnetic microstructures selectively-targeted to include at least one transmembrane receptor targeting moiety. At 1516, detecting the spatial distribution of the magnetic resonance event includes detecting the spatial distribution of the magnetic resonance event associated with one or more ferromagnetic microstructures selectively-targeted to at least one antigen-targeting moiety. At 1518, detecting the spatial distribution of the magnetic resonance event includes detecting the spatial distribution of the magnetic resonance event associated with one or more ferromagnetic microstructures selectively-targeted to at least one immune-receptor targeting moiety.

At 1520, detecting the spatial distribution of the magnetic resonance event includes detecting the spatial distribution of the magnetic resonance event associated with one or more ferromagnetic microstructures selectively-targeted to at least one folate receptor targeting moiety. At 1522, detecting the spatial distribution of the magnetic resonance event includes detecting the spatial distribution of the magnetic resonance event associated with one or more ferromagnetic microstructures selectively-targeted to at least one nucleotide binding moiety. At 1524, detecting the spatial distribution of the magnetic resonance event includes detecting the spatial distribution of the magnetic resonance event associated with one or more ferromagnetic microstructures selectively-targeted to at least one oligonucleotide binding moiety. At 1526, detecting the spatial distribution of the magnetic resonance event includes detecting the spatial distribution of the magnetic resonance event associated with one or more ferromagnetic microstructures selectively-targeted to at least one oligodeoxyribonucleotide binding moiety. At 1528, detecting the spatial distribution of the magnetic resonance event includes detecting the spatial distribution of the magnetic resonance event associated with one or more ferromagnetic microstructures selectively-targeted to at least one oligoribonucleotide binding moiety.

At 1530, detecting the spatial distribution of the magnetic resonance event includes detecting the spatial distribution of the magnetic resonance event associated with one or more ferromagnetic microstructures selectively-targeted to at least one amyloid binding moiety. At 1532, detecting the spatial distribution of the magnetic resonance event includes detecting the spatial distribution of the magnetic resonance event associated with one or more ferromagnetic microstructures selectively-targeted to at least one β-amyloid binding moiety. At 1534, detecting the spatial distribution of the magnetic resonance event includes detecting the spatial distribution of the magnetic resonance event associated with one or more ferromagnetic microstructures selectively-targeted to one or more genomic targets. At 1536, detecting the spatial distribution of the magnetic resonance event includes detecting the spatial distribution of the magnetic resonance event associated with one or more ferromagnetic microstructures selectively-targeted to at least one oncogene. At 1538, detecting the spatial distribution of the magnetic resonance event includes detecting the spatial distribution of the magnetic resonance event associated with one or more ferromagnetic microstructures selectively-targeted to at least one chromosome translocation.

At 1540, detecting the spatial distribution of the magnetic resonance event includes detecting the spatial distribution of the magnetic resonance event associated with one or more ferromagnetic microstructures selectively-targeted to at least one methylated deoxyribonucleic acid sequence. At 1542, detecting the spatial distribution of the magnetic resonance event includes detecting the spatial distribution of the magnetic resonance event associated with one or more ferromagnetic microstructures selectively-targeted to at least one methylated deoxyribonucleic acid sequence including a methylated cytosine. At 1544, detecting the spatial distribution of the magnetic resonance event includes detecting the spatial distribution of the magnetic resonance event associated with one or more ferromagnetic microstructures selectively-targeted to at least one methylated ribonucleic acid sequence. At 1546, detecting the spatial distribution of the magnetic resonance event includes detecting the spatial distribution of the magnetic resonance event associated with one or more ferromagnetic microstructures selectively-targeted to at least one deoxyribonucleic acid sequence including unmethylated cytosine.

At 1548, detecting the spatial distribution of the magnetic resonance event includes detecting the spatial distribution of the magnetic resonance event associated with one or more ferromagnetic microstructures selectively-targeted to at least one single-nucleotide polymorphism. At 1550, detecting the spatial distribution of the magnetic resonance event includes detecting the spatial distribution of the magnetic resonance event associated with one or more ferromagnetic microstructures selectively-targeted to at least one of a somatic mutation, germline mutation, chemically induced mutation, biologically induce mutation, or an environmentally induce mutation. At 1552, detecting the spatial distribution of the magnetic resonance event includes detecting the spatial distribution of the magnetic resonance event associated with one or more ferromagnetic microstructures selectively-targeted to at least one double stranded deoxyribonucleic acid sequence. At 1554, detecting the spatial distribution of the magnetic resonance event includes detecting the spatial distribution of the magnetic resonance event associated with one or more ferromagnetic microstructures selectively-targeted to at least one single stranded deoxyribonucleic acid sequence. At 1556, detecting the spatial distribution of the magnetic resonance event includes detecting the spatial distribution of the magnetic resonance event associated with one or more ferromagnetic microstructures selectively-targeted to at least one mitochondrial deoxyribonucleic acid sequence. At 1558, detecting the spatial distribution of the magnetic resonance event includes detecting the spatial distribution of the magnetic resonance event associated with one or more ferromagnetic microstructures selectively-targeted to at least one of a point mutation, an insertion of one or more nucleotides, or a deletion of one or more nucleotides.

At 1560, detecting the spatial distribution of the magnetic resonance event includes detecting the spatial distribution of the magnetic resonance event associated with one or more ferromagnetic microstructures selectively-targeted to at least a portion of a human chromosome in vivo. At 1562, detecting the spatial distribution of the magnetic resonance event includes detecting the spatial distribution of the magnetic resonance event associated with one or more ferromagnetic microstructures selectively-targeted to a zinc finger-including protein. At 1564, detecting the spatial distribution of the magnetic resonance event includes detecting the spatial distribution of the magnetic resonance event associated with one or more ferromagnetic microstructures selectively-targeted to a deoxyribonucleic acid sequence. At 1566, detecting the spatial distribution of the magnetic resonance event includes detecting the spatial distribution of the magnetic resonance event associated with one or more ferromagnetic microstructures selectively-targeted to a ribonucleic acid sequence target. At 1568, detecting the spatial distribution of the magnetic resonance event includes detecting the spatial distribution of the magnetic resonance event associated with one or more ferromagnetic microstructures selectively-targeted to an antigen epitope. At 1570, detecting the spatial distribution of the magnetic resonance event includes detecting the spatial distribution of the magnetic resonance event associated with one or more ferromagnetic microstructures selectively-targeted to an antigen mimotope. At 1572, detecting the spatial distribution of the magnetic resonance event includes detecting a spatial distribution of a magnetic resonance event associated with the targeted biological sample exposed to a selectively-accessible surface-defined void of one or more selectively-targeted, selectively-accessible, ferromagnetic microstructures.

At 1580, the method 1500 includes generating a response based on the detected spatial distribution of the magnetic resonance event.

Figure 16:
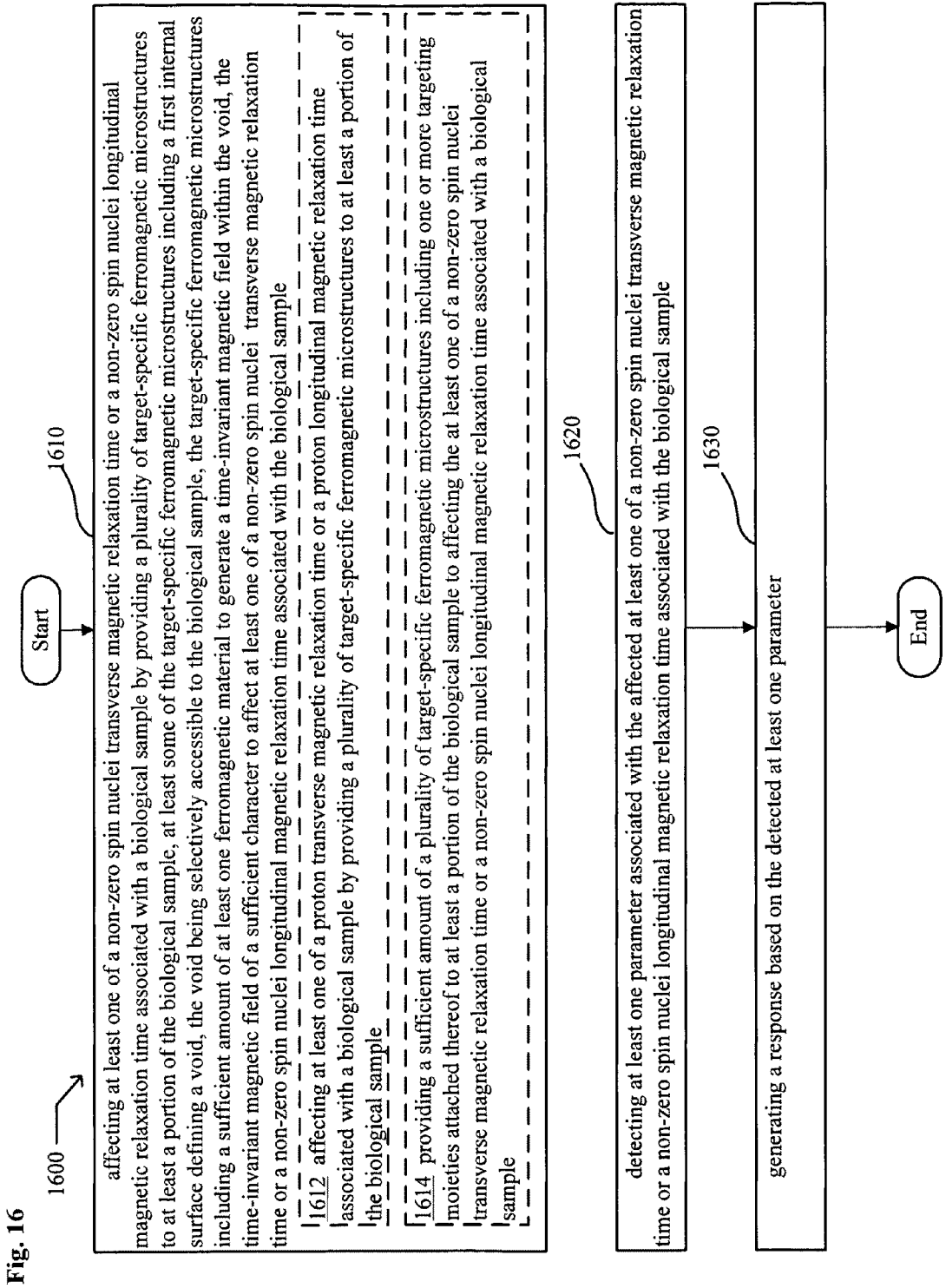
FIG. 16 is a flow diagram of a method according to one illustrated embodiment.

FIG. 16 shows an example of a method 1600.

At 1610, the method 1600 includes affecting at least one of a non-zero spin nuclei transverse magnetic relaxation time or a non-zero spin nuclei longitudinal magnetic relaxation time associated with a biological sample by providing a plurality of target-specific ferromagnetic microstructures to at least a portion of the biological sample, at least some of the target-specific ferromagnetic microstructures including a first internal surface defining a void, the void being selectively accessible to the biological sample, the target-specific ferromagnetic microstructures including a sufficient amount of at least one ferromagnetic material to generate a time-invariant magnetic field within the void, the time-invariant magnetic field of a sufficient character to affect at least one of a non-zero spin nuclei transverse magnetic relaxation time or a non-zero spin nuclei longitudinal magnetic relaxation time associated with the biological sample. At 1612, affecting the at least one of a non-zero spin nuclei transverse magnetic relaxation time or the non-zero spin nuclei longitudinal magnetic relaxation time includes affecting at least one of a proton transverse magnetic relaxation time or a proton longitudinal magnetic relaxation time associated with a biological sample by providing a plurality of target-specific ferromagnetic microstructures to at least a portion of the biological sample. At 1614, affecting the at least one of a non-zero spin nuclei transverse magnetic relaxation time or a non-zero spin nuclei longitudinal magnetic relaxation time includes providing a sufficient amount of a plurality of target-specific ferromagnetic microstructures including one or more targeting moieties attached thereof to at least a portion of the biological sample to affecting the at least one of a non-zero spin nuclei transverse magnetic relaxation time or a non-zero spin nuclei longitudinal magnetic relaxation time associated with a biological sample.

At 1620, the method 1600 includes detecting at least one parameter associated with the affected at least one of a non-zero spin nuclei transverse magnetic relaxation time or a non-zero spin nuclei longitudinal magnetic relaxation time associated with the biological sample. At 1630, the method 1600 includes generating a response based on the detected at least one parameter.

Figure 17A:
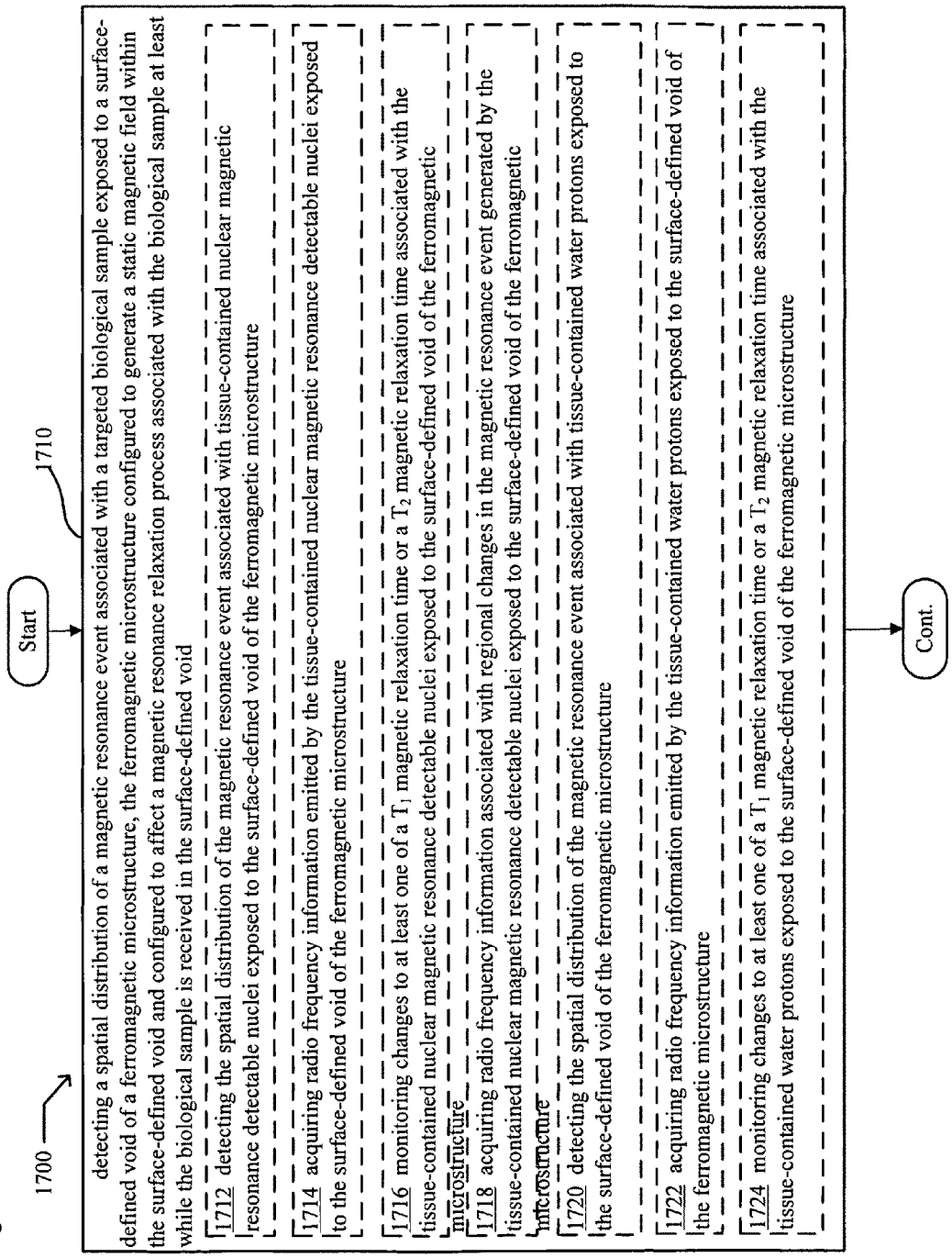
FIGS. 17A-17R are flow diagrams of a method according to one illustrated embodiment.
Figure 17B:
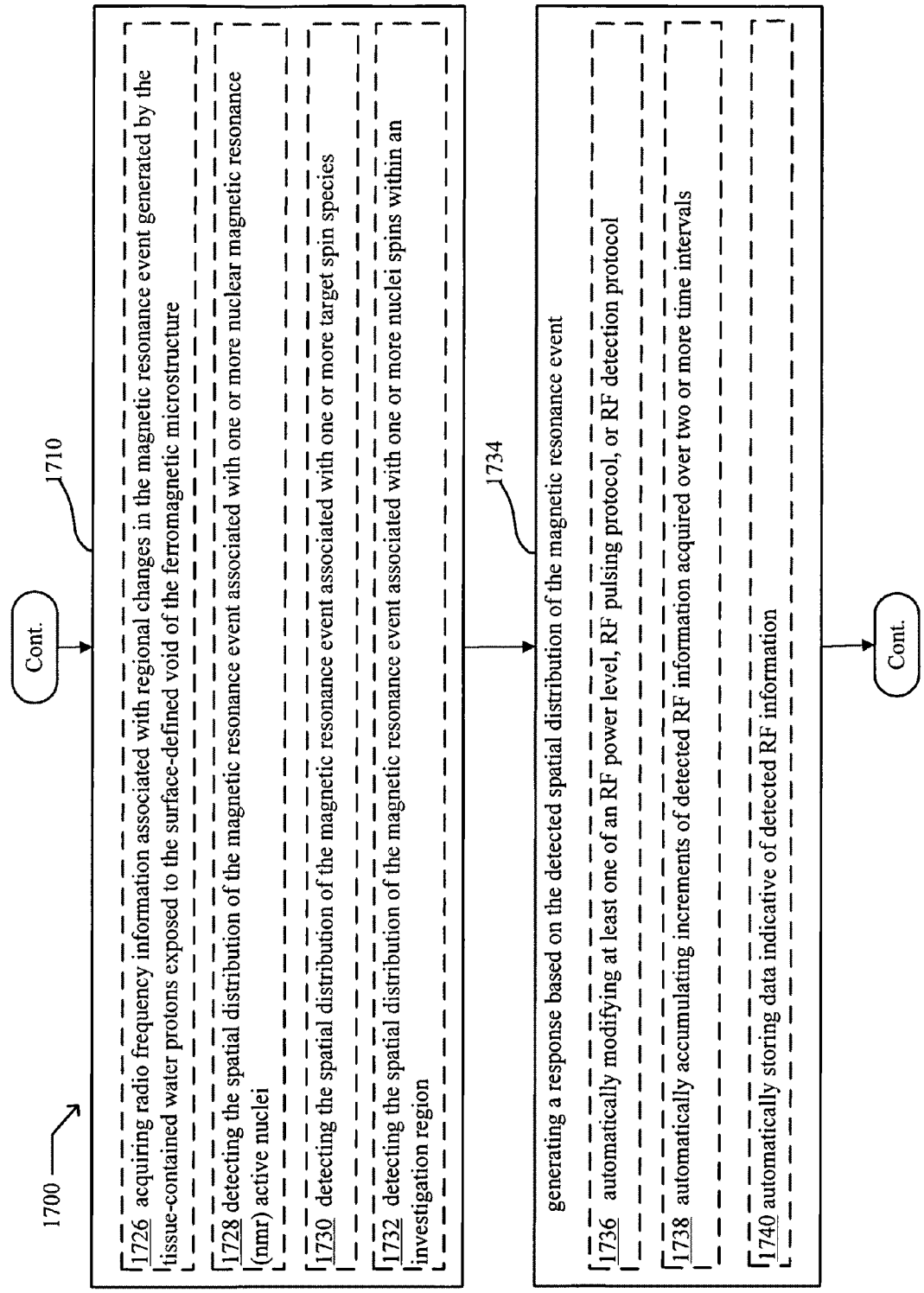
Figure 17C:
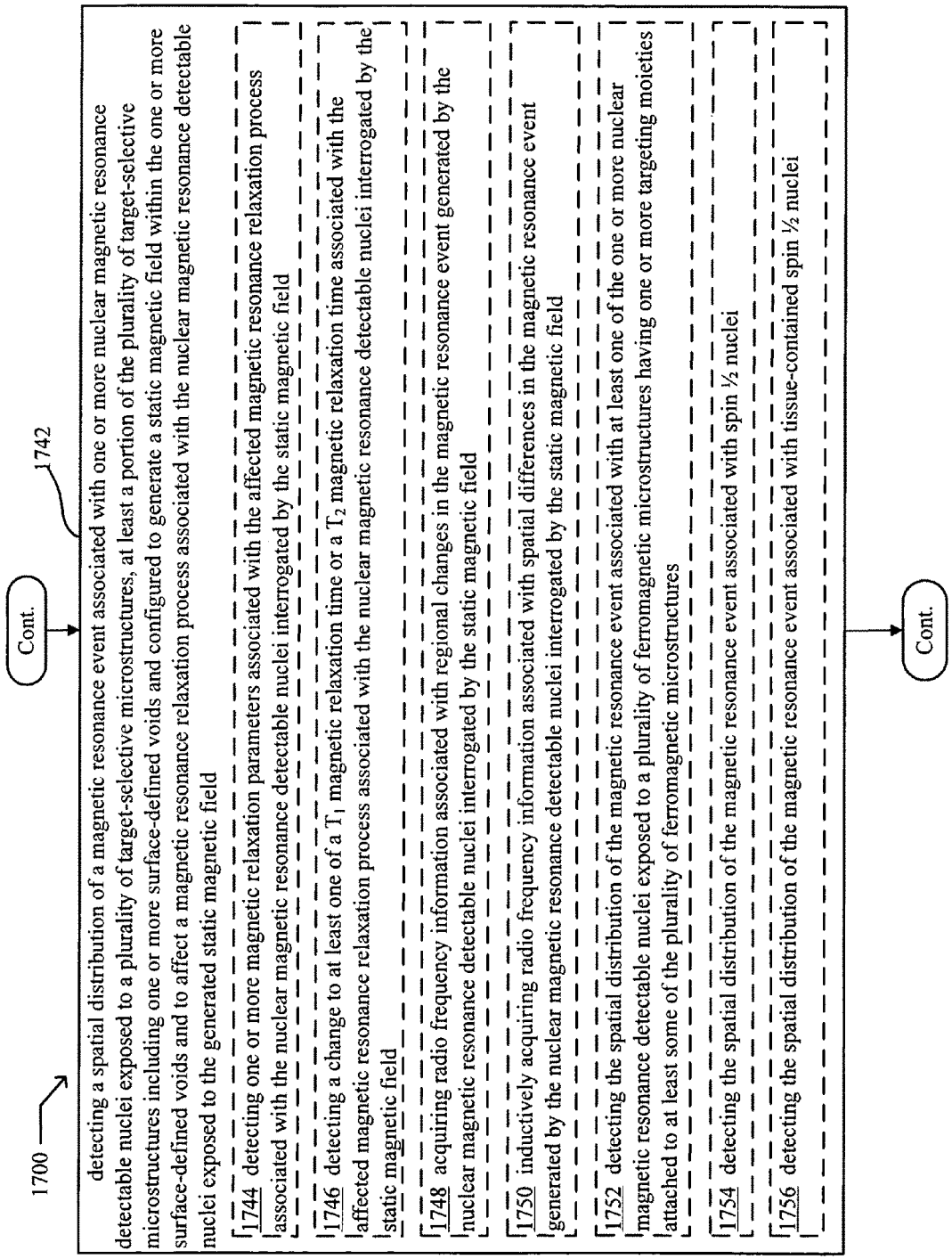
Figure 17F:
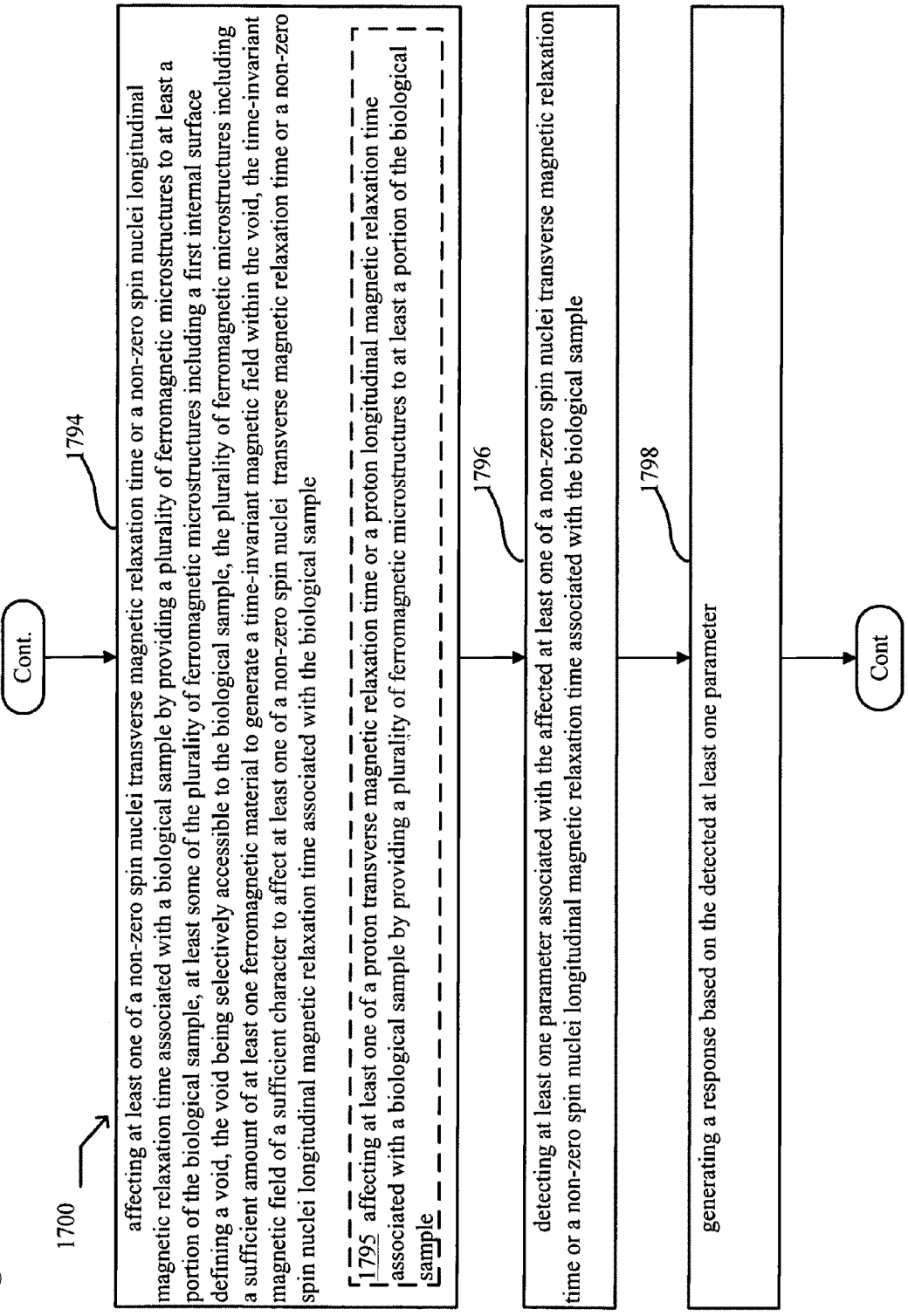
Figure 17G:
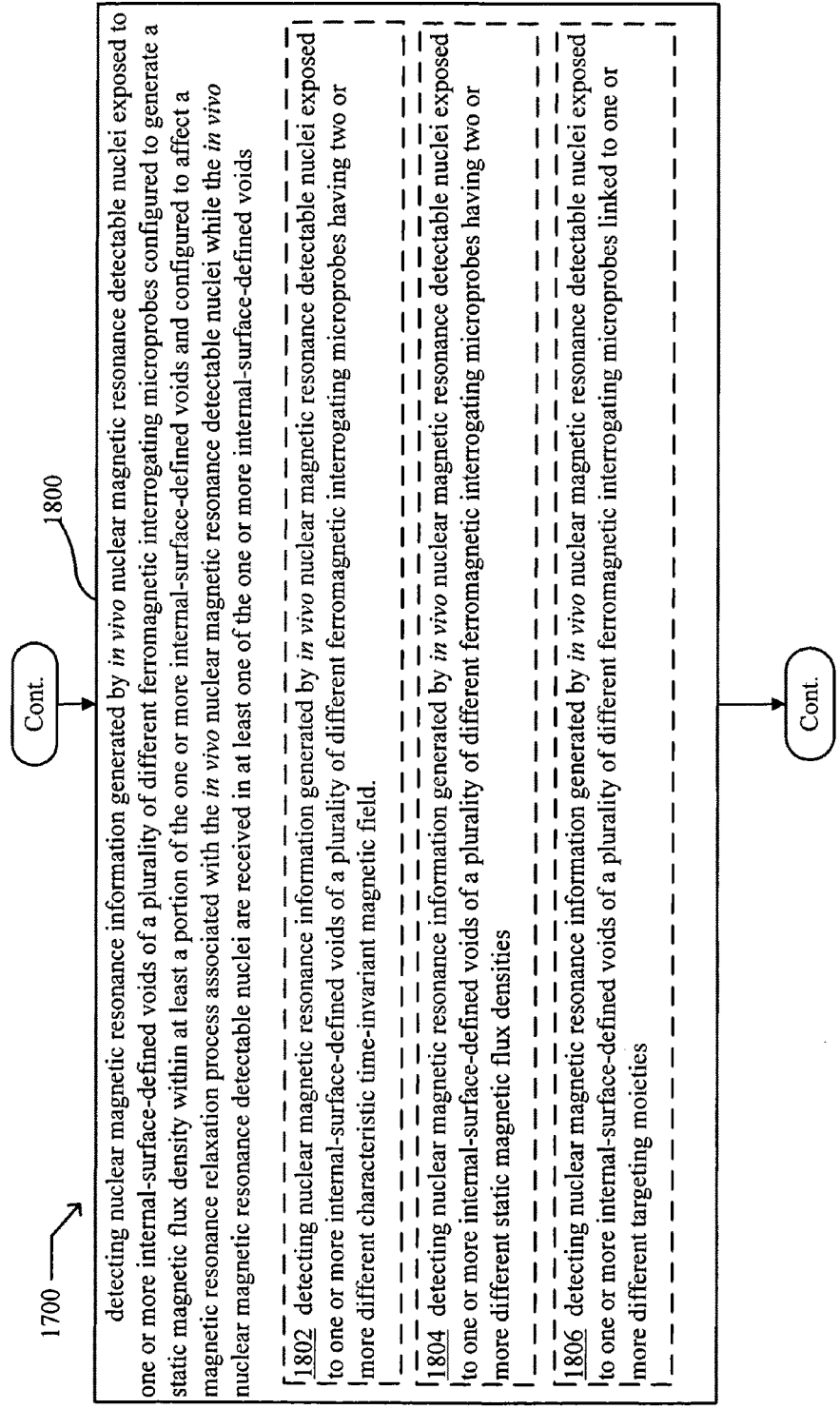
Figure 17H:
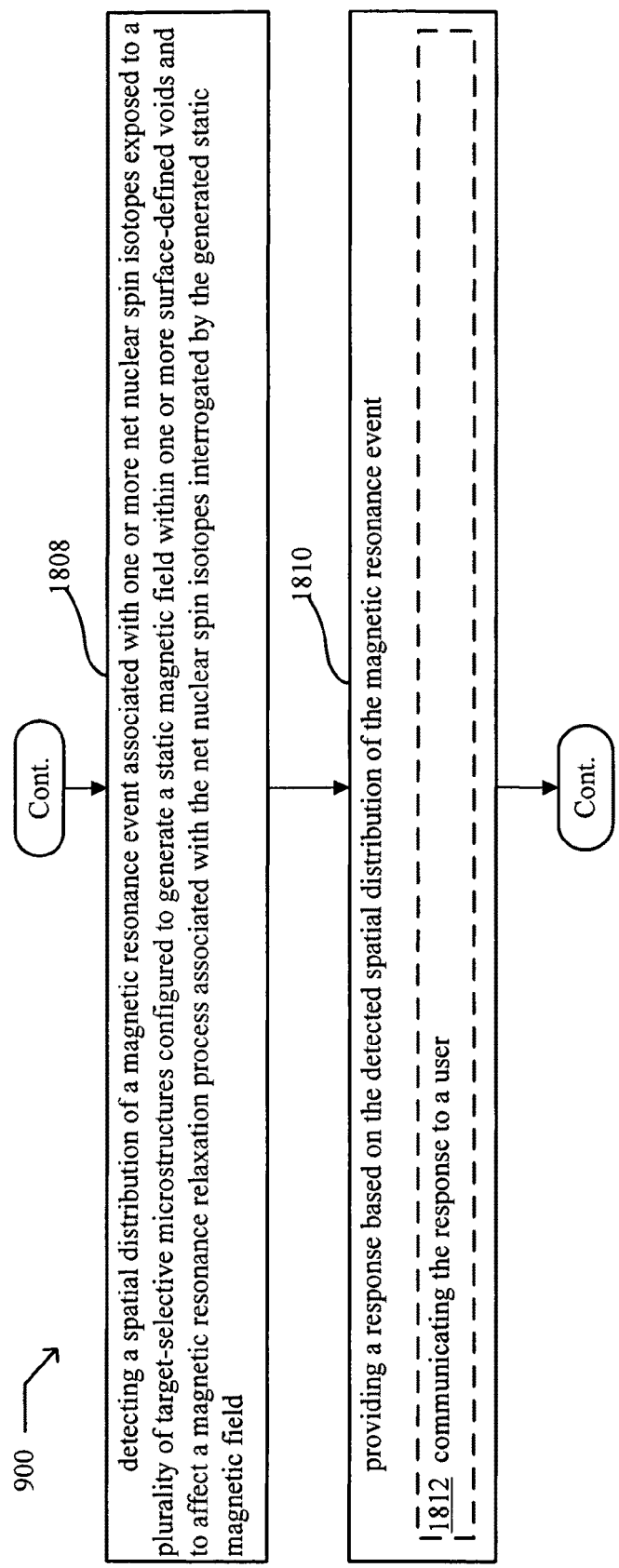
Figure 17I:
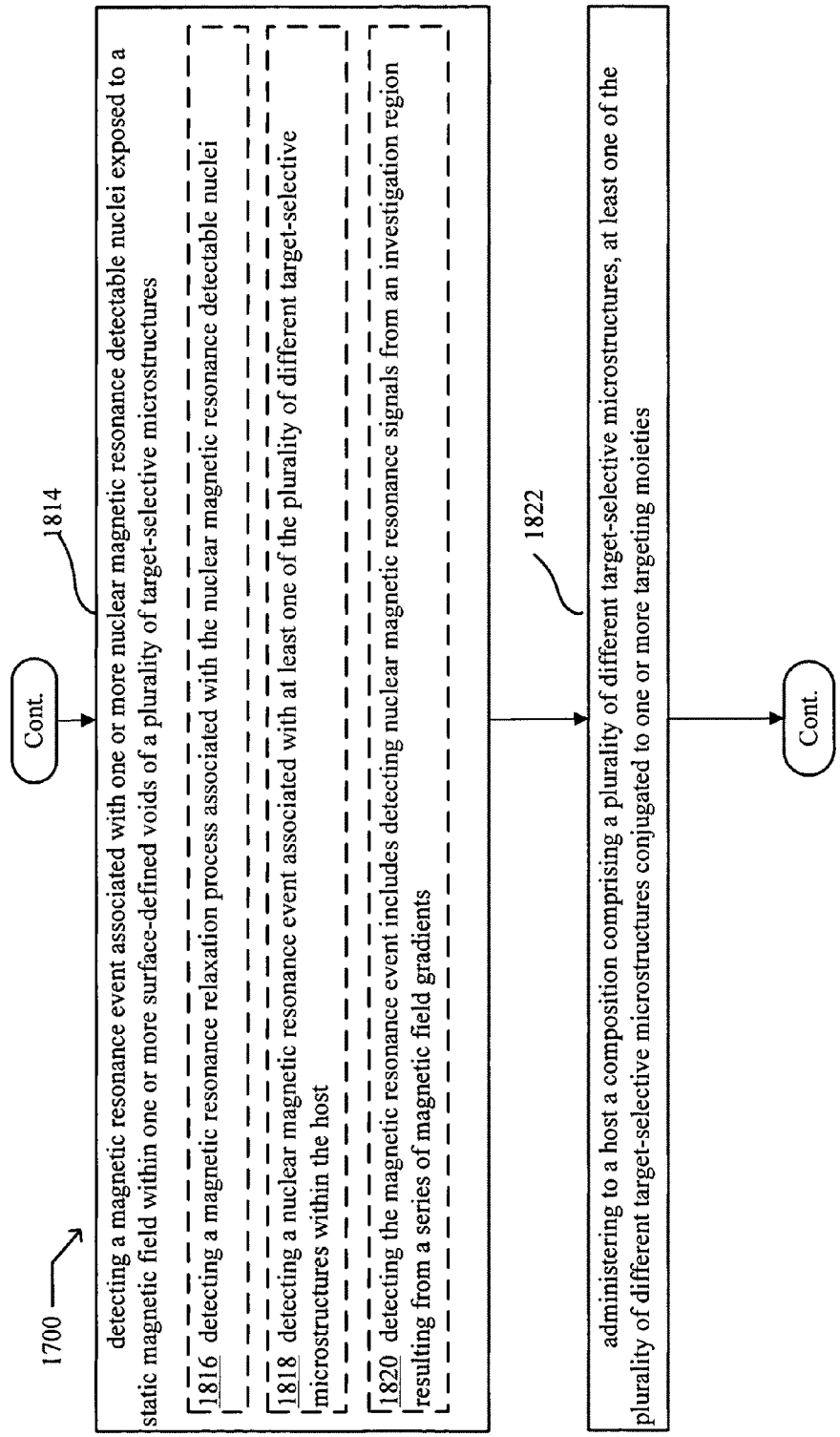
Figure 17J:
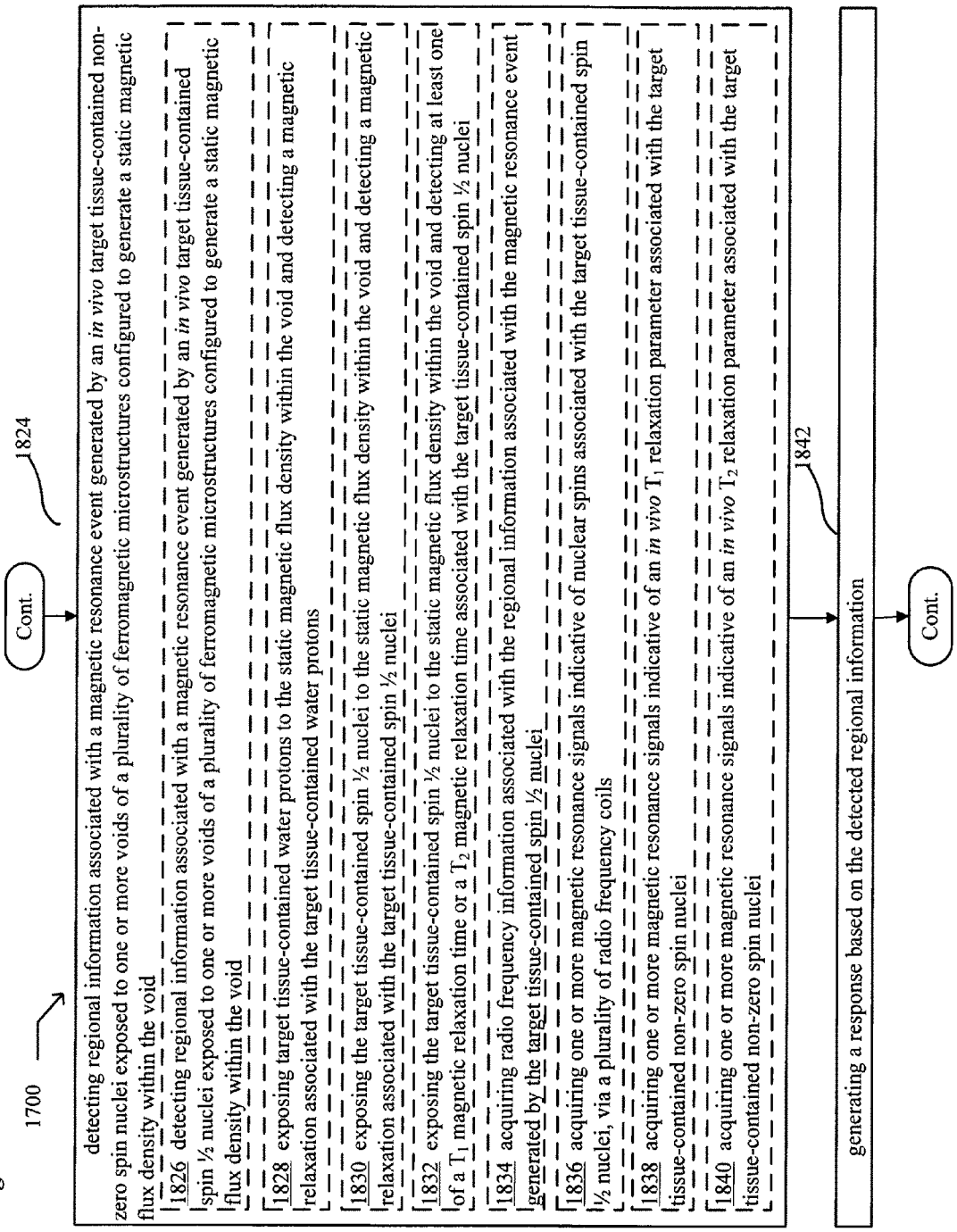
Figure 17K:
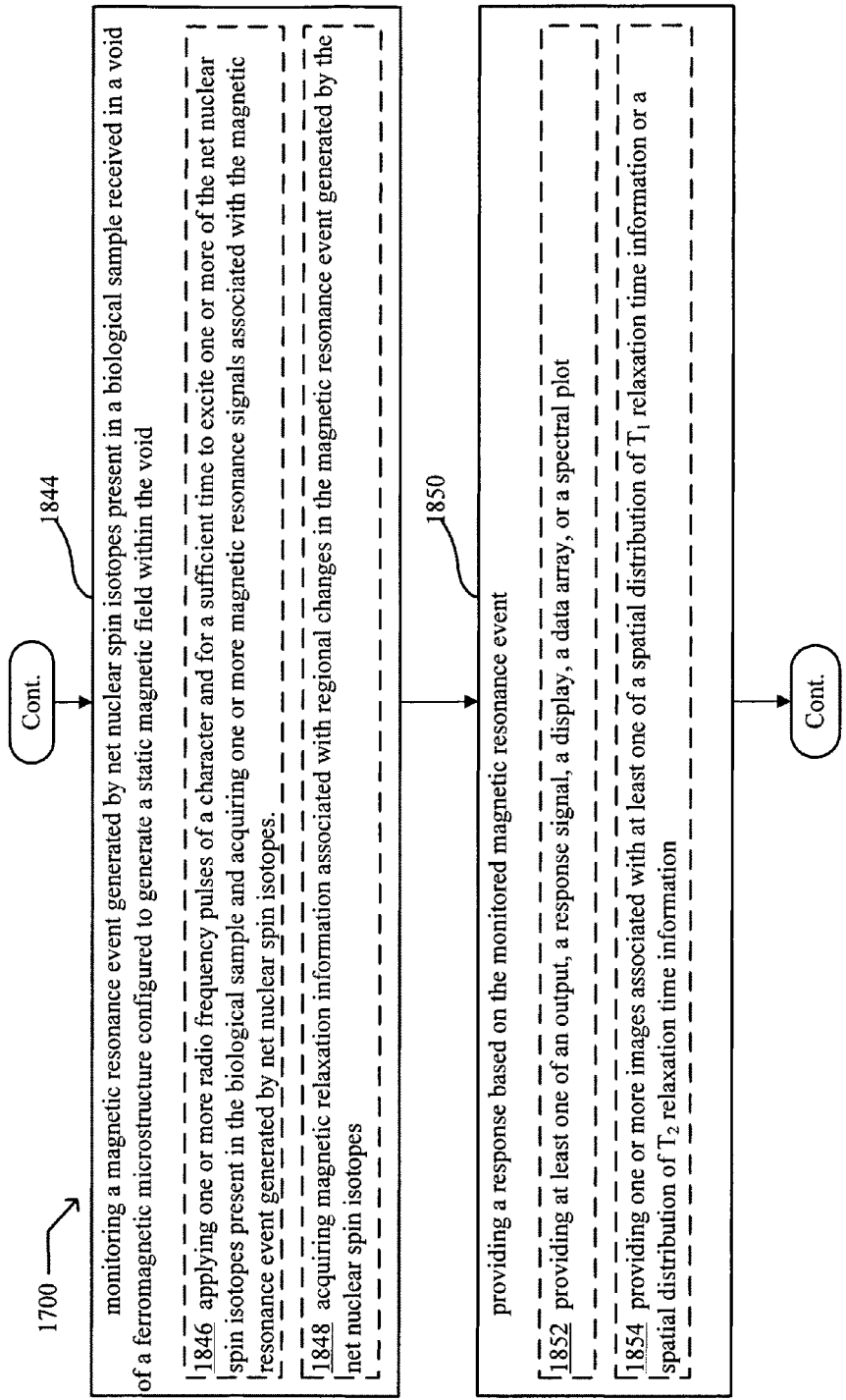
Figure 17M:
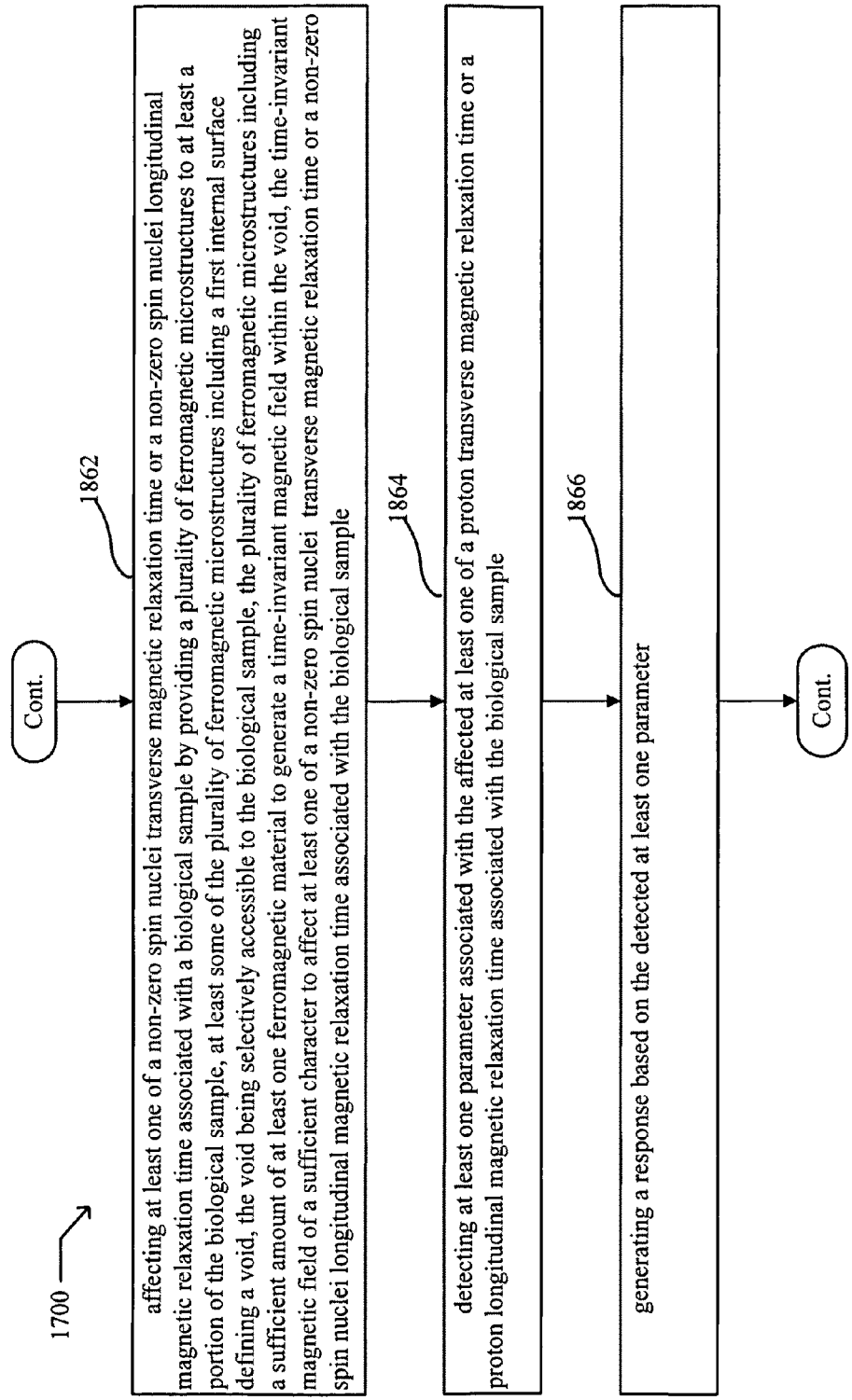
Figure 17O:
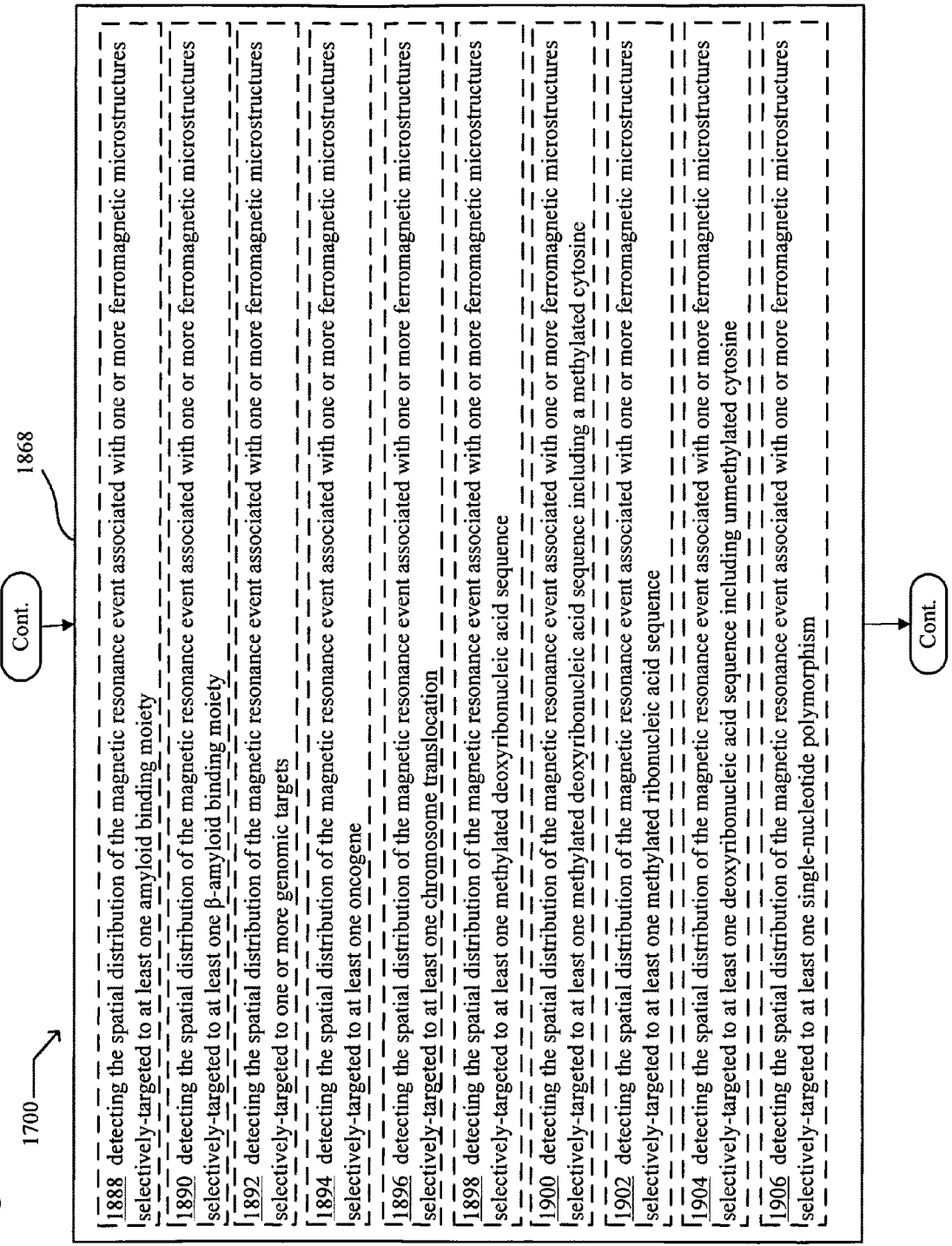
Figure 17P:
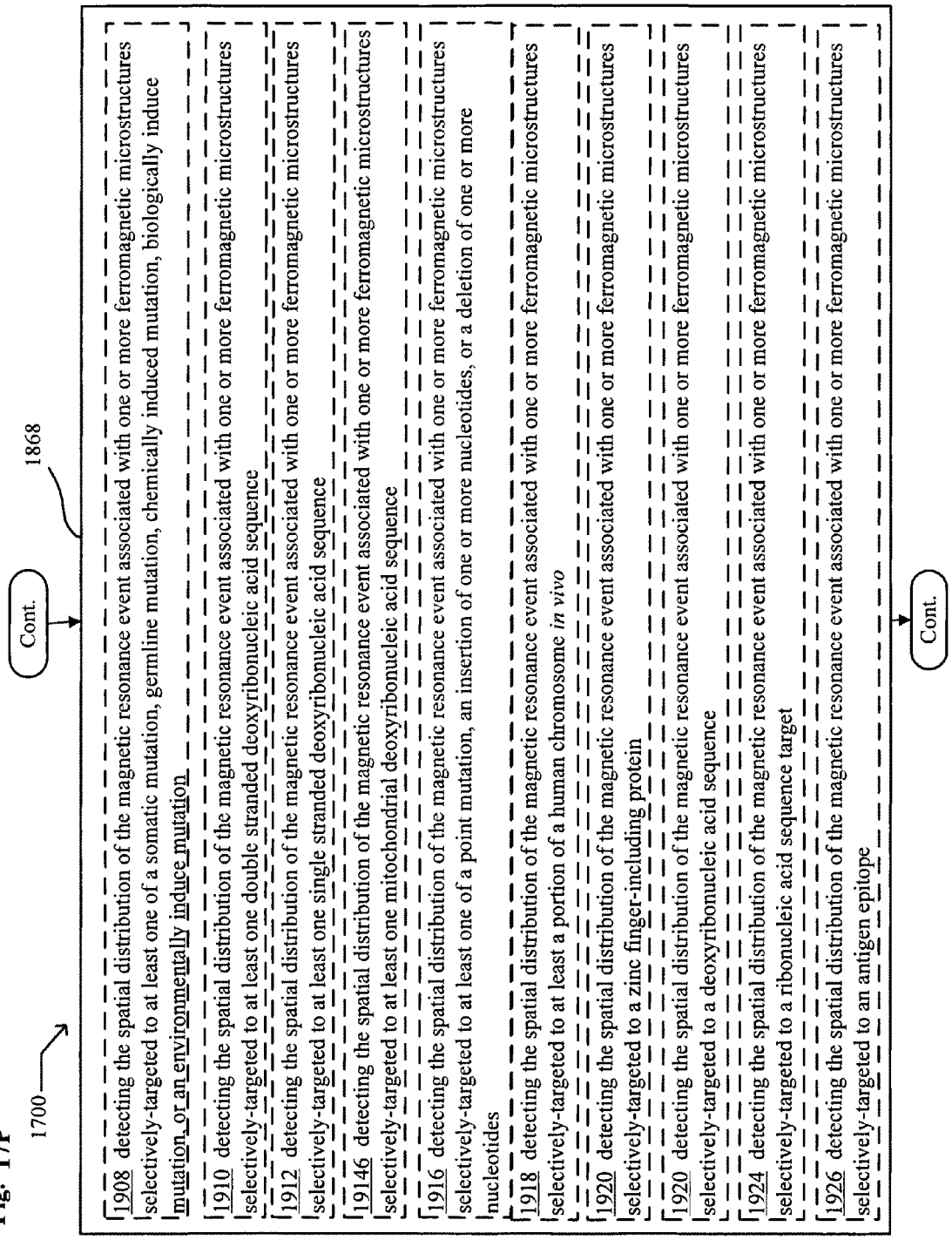
Figure 17Q:
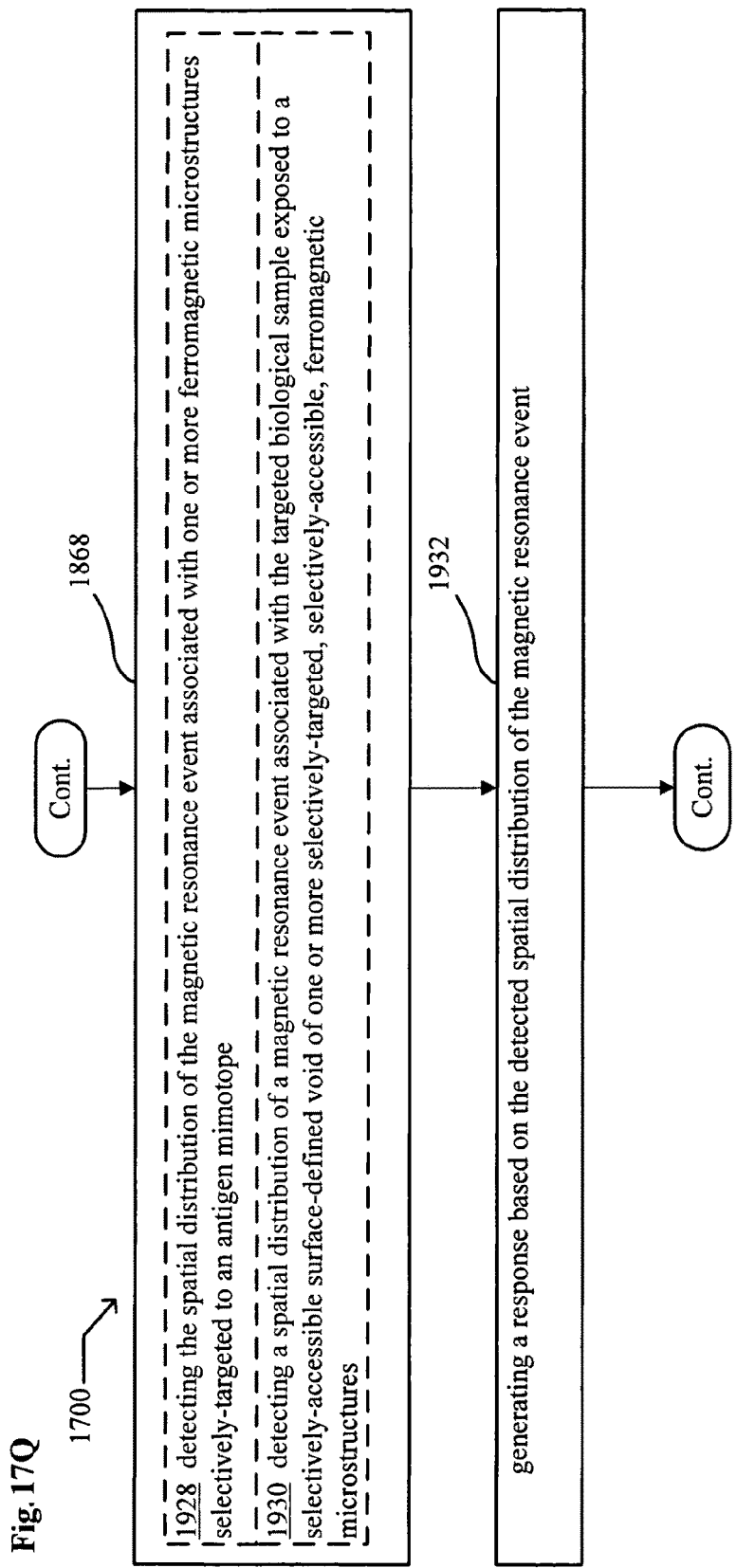

FIGS. 17A through 17R show an example of a method 1700.

At 1710, the method 1700 can include detecting a spatial distribution of a magnetic resonance event associated with a targeted biological sample exposed to a surface-defined void 106 of a ferromagnetic microstructure, the ferromagnetic microstructure configured to generate a static magnetic field within the surface-defined void 106 and configured to affect a magnetic resonance relaxation process associated with the biological sample at least while the biological sample is received in the surface-defined void 106. At 1712, detecting the spatial distribution of a magnetic resonance event can include detecting the spatial distribution of the magnetic resonance event associated with tissue-contained nuclear magnetic resonance detectable nuclei exposed to the surface-defined void 106 of the ferromagnetic microstructure. At 1714, detecting the spatial distribution of a magnetic resonance event can include acquiring RF information emitted by the tissue-contained nuclear magnetic resonance detectable nuclei exposed to the surface-defined void 106 of the ferromagnetic microstructure. At 1716, detecting the spatial distribution of a magnetic resonance event can include monitoring changes to at least one of a $T_1$ magnetic relaxation time or a $T_2$ magnetic relaxation time associated with the tissue-contained nuclear magnetic resonance detectable nuclei exposed to the surface-defined void 106 of the ferromagnetic microstructure. At 1718, detecting the spatial distribution of a magnetic resonance event can include acquiring RF information associated with regional changes in the magnetic resonance event generated by the tissue-contained nuclear magnetic resonance detectable nuclei exposed to the surface-defined void 106 of the ferromagnetic microstructure. At 1720, detecting the spatial distribution of a magnetic resonance event can include detecting the spatial distribution of the magnetic resonance event associated with tissue-contained water protons exposed to the surface-defined void 106 of the ferromagnetic microstructure. At 1722, detecting the spatial distribution of a magnetic resonance event can include acquiring RF information emitted by the tissue-contained water protons exposed to the surface-defined void 106 of the ferromagnetic microstructure. At 1724, detecting the spatial distribution of a magnetic resonance event can include monitoring changes to at least one of a $T_1$ magnetic relaxation time or a $T_2$ magnetic relaxation time associated with the tissue-contained water protons exposed to the surface-defined void 106 of the ferromagnetic microstructure. At 1726, detecting the spatial distribution of a magnetic resonance event can include acquiring RF information associated with regional changes in the magnetic resonance event generated by the tissue-contained water protons exposed to the surface-defined void 106 of the ferromagnetic microstructure. At 1728, detecting the spatial distribution of a magnetic resonance event can include detecting the spatial distribution of the magnetic resonance event associated with one or more NMR active nuclei. At 1730, detecting the spatial distribution of a magnetic resonance event can include detecting the spatial distribution of the magnetic resonance event associated with one or more target spin species. At 1732, detecting the spatial distribution of a magnetic resonance event can include detecting the spatial distribution of the magnetic resonance event associated with one or more nuclei spins within an investigation region.

At 1734, the method 1700 can include generating a response based on the detected spatial distribution of the magnetic resonance event.

At 1736, generating the response can include automatically modifying at least one of an RF power level, an RF pulsing protocol, or an RF detection protocol. At 1738, generating the response can include automatically accumulating increments of detected RF information acquired over two or more time intervals. At 1740, generating the response can include automatically storing data indicative of detected RF information.

At 1742, the method 1700 can include detecting a spatial distribution of a magnetic resonance event associated with one or more nuclear magnetic resonance detectable nuclei exposed to a plurality of target-selective microstructures. In an embodiment, at least a portion of the plurality of target-selective microstructures include one or more surface-defined voids 106, and are configured to generate a static magnetic field within the one or more surface-defined voids 106 and to affect a magnetic resonance relaxation process associated with the nuclear magnetic resonance detectable nuclei exposed to the generated static magnetic field. At 1744, detecting the spatial distribution of the magnetic resonance event can include detecting one or more magnetic relaxation parameters associated with the affected magnetic resonance relaxation process associated with the nuclear magnetic resonance detectable nuclei interrogated by the static magnetic field. At 1746, detecting the spatial distribution of the magnetic resonance event can include detecting a change to at least one of a $T_1$ magnetic relaxation time or a $T_2$ magnetic relaxation time associated with the affected magnetic resonance relaxation process associated with the nuclear magnetic resonance detectable nuclei interrogated by the static magnetic field. At 1748, detecting the spatial distribution of the magnetic resonance event can include acquiring RF information associated with regional changes in the magnetic resonance event generated by the nuclear magnetic resonance detectable nuclei interrogated by the static magnetic field. At 1750, detecting the spatial distribution of the magnetic resonance event can include inductively acquiring RF information associated with spatial differences in the magnetic resonance event generated by the nuclear magnetic resonance detectable nuclei interrogated by the static magnetic field. At 1752, detecting the spatial distribution of the magnetic resonance event can include detecting the spatial distribution of the magnetic resonance event associated with at least one of the one or more nuclear magnetic resonance detectable nuclei exposed to a plurality of target-selective microstructures having one or more targeting moieties 112 attached to one or more of the plurality of target-selective microstructures.

At 1754, detecting the spatial distribution of the magnetic resonance event includes detecting the spatial distribution of the magnetic resonance event associated with spin ½ nuclei. At 1756, detecting the spatial distribution of the magnetic resonance event includes detecting the spatial distribution of the magnetic resonance event associated with tissue-contained spin ½ nuclei. At 1758, detecting the spatial distribution of the magnetic resonance includes detecting the spatial distribution of the magnetic resonance event associated with hydrogen nuclei. At 1760, detecting the spatial distribution of the magnetic resonance event includes detecting the spatial distribution of the magnetic resonance event associated with tissue-contained water protons. At 1762, detecting the spatial distribution of the magnetic resonance event includes detecting one or more magnetic relaxation parameters associated with the affected magnetic resonance relaxation process associated with tissue-contained water protons interrogated by the static magnetic field. At 1764, detecting the spatial distribution of the magnetic resonance event includes detecting the spatial distribution of the magnetic resonance event associated with one or more net nuclear spin isotopes. At 1766, detecting the spatial distribution of the magnetic resonance event includes detecting the spatial distribution of the magnetic resonance event associated with tissue-contained water protons exposed to a plurality of ferromagnetic target-selective microstructures.

At 1768, the method 1700 can include providing a response based on the detected spatial distribution of the magnetic resonance event. At 1770, providing the response includes automatically providing information associated with least one of a transverse magnetic relaxation event or a longitudinal magnetic relaxation event associated with the detected spatial distribution of the magnetic resonance event. At 1772, providing the response includes automatically providing information associated with at least one of a $T_1$ magnetic resonance process or a $T_2$ magnetic resonance process. At 1774, providing the response includes automatically providing information associated with at least one of a water $T_1$ magnetic resonance process or a water $T_2$ magnetic resonance process. At 1776, providing the response includes automatically providing at least one of a tissue-contained water proton $T_1$ relaxation information, or tissue-contained water proton $T_2$ relaxation information. At 1778, providing the response includes providing an image associated with at least one of a spatial distribution of $T_1$ relaxation time information or a spatial distribution of $T_2$ relaxation time information. At 1780, providing the response includes providing one or more $T_1$ maps. At 1782, providing the response includes providing one or more $T_2$ maps. At 1784, providing the response includes providing one or more $T_1$-weighted images. See, e.g., U.S. Pat. No. 7,276,904 (issued Oct. 2, 2007) (the contents of which are incorporated herein by reference). At 1786, providing the response includes providing one or more $T_2$-weighted images. At 1788, providing the response includes providing a cluster-based analysis of at least one of a quantitative $T_1$ relaxation map, or a quantitative $T_2$ relaxation map. At 1790, providing the response includes providing a voxel-based analysis of at least one of $T_1$ relaxation information or a $T_2$ relaxation information. At 1792, providing the response includes providing a voxel-based analysis of at least one of quantitative $T_1$ relaxation maps or quantitative $T_2$ relaxation maps. At 1793, providing the response includes providing one or more magnetic resonance images.

At 1794, the method 1700 can include affecting at least one of a non-zero spin nuclei transverse magnetic relaxation time or a non-zero spin nuclei longitudinal magnetic relaxation time associated with a biological sample by providing a plurality of ferromagnetic microstructures to at least a portion of the biological sample, at least some of the plurality of ferromagnetic microstructures including a first internal surface defining a void, the void being selectively accessible to the biological sample, the plurality of ferromagnetic microstructures including a sufficient amount of at least one ferromagnetic material to generate a time-invariant magnetic field within the void, the time-invariant magnetic field of a sufficient character to affect at least one of a non-zero spin nuclei transverse magnetic relaxation time or a non-zero spin nuclei longitudinal magnetic relaxation time associated with the biological sample. At 1795, affecting at least one of a non-zero spin nuclei transverse magnetic relaxation time or a non-zero spin nuclei longitudinal magnetic relaxation time can include affecting at least one of a proton transverse magnetic relaxation time or a proton longitudinal magnetic relaxation time associated with a biological sample by providing a plurality of ferromagnetic microstructures to at least a portion of the biological sample.

At 1796, the method 1700 can include detecting at least one parameter associated with the affected at least one of a non-zero spin nuclei transverse magnetic relaxation time or a non-zero spin nuclei longitudinal magnetic relaxation time associated with the biological sample.

At 1798, the method 1700 can include generating a response based on the detected at least one parameter.

At 1800, the method 1700 can include detecting nuclear magnetic resonance information generated by in vivo nuclear magnetic resonance detectable nuclei exposed to one or more internal-surface-defined voids 106 of a plurality of different ferromagnetic microstructures configured to generate a static magnetic flux density within at least a portion of the one or more internal-surface-defined voids 106 and configured to affect a magnetic resonance relaxation process associated with the in vivo nuclear magnetic resonance detectable nuclei while the in vivo nuclear magnetic resonance detectable nuclei are received in at least one of the one or more internal-surface-defined voids. At 1802, detecting the nuclear magnetic resonance information includes detecting nuclear magnetic resonance information generated by in vivo nuclear magnetic resonance detectable nuclei exposed to one or more internal-surface-defined voids 106 of a plurality of different ferromagnetic microstructures having two or more different characteristic time-invariant magnetic field 108. At 1804, detecting the nuclear magnetic resonance information includes detecting nuclear magnetic resonance information generated by in vivo nuclear magnetic resonance detectable nuclei exposed to one or more internal-surface-defined voids 106 of a plurality of different ferromagnetic microstructures having two or more different static magnetic flux densities. At 1806, detecting the nuclear magnetic resonance information includes detecting nuclear magnetic resonance information generated by in vivo nuclear magnetic resonance detectable nuclei exposed to one or more internal-surface-defined voids 106 of a plurality of different ferromagnetic microstructures linked to one or more different targeting moieties. At 1808, the method 1700 can include detecting a spatial distribution of a magnetic resonance event associated with one or more net nuclear spin isotopes exposed to a plurality of target-selective microstructures configured to generate a static magnetic field within one or more surface-defined voids 106 and to affect a magnetic resonance relaxation process associated with the net nuclear spin isotopes interrogated by the generated static magnetic field.

At 1810, the method 1700 can include providing a response based on the detected spatial distribution of the magnetic resonance event. At 1812, providing the response can include communicating the response to a user.

At 1814, the method 1700 can include detecting a magnetic resonance event associated with one or more nuclear magnetic resonance detectable nuclei exposed to a static magnetic field within one or more surface-defined voids 106 of a plurality of target-selective microstructures. At 1816, detecting magnetic resonance event can include detecting a magnetic resonance relaxation process associated with the nuclear magnetic resonance detectable nuclei. At 1818, detecting the magnetic resonance event can include detecting a nuclear magnetic resonance event associated with at least one of the plurality of different target-selective microstructures within the host. At 1820, detecting the magnetic resonance event includes detecting nuclear magnetic resonance signals from an investigation region resulting from a series of magnetic field gradients. At 1822, the method 1700 can include administering to a host a composition comprising a plurality of different target-selective microstructures, at least one of the plurality of different target-selective microstructures conjugated to one or more targeting moieties.

At 1824, the method 1700 can include detecting regional information associated with a magnetic resonance event generated by in vivo target tissue-contained non-zero spin nuclei exposed to one or more voids 106 of a plurality of ferromagnetic microstructures 102 configured to generate a static magnetic flux density within the void 106. At 1826, detecting the regional information associated with the magnetic resonance event includes detecting regional information associated with a magnetic resonance event generated by in vivo target tissue-contained spin ½ nuclei exposed to one or more voids 106 of a plurality of ferromagnetic microstructures 102 configured to generate a static magnetic flux density within the void 106. At 1828, detecting the regional information associated with the magnetic resonance event includes exposing target tissue-contained water protons to the static magnetic flux density within the void 106 and detecting a magnetic relaxation associated with the target tissue-contained water protons. At 1830, detecting the regional information associated with the magnetic resonance event includes exposing the target tissue-contained spin ½ nuclei to the static magnetic flux density within the void 106 and detecting a magnetic relaxation associated with the target tissue-contained spin ½ nuclei. At 1832, detecting the regional information associated with the magnetic resonance event includes exposing the target tissue-contained spin ½ nuclei to the static magnetic flux density within the void 106 and detecting at least one of a $T_1$ magnetic relaxation time or a $T_2$ magnetic relaxation time associated with the target tissue-contained spin ½ nuclei. At 1834, detecting the regional information associated with the magnetic resonance event includes acquiring RF information associated with the regional information associated with the magnetic resonance event generated by the target tissue-contained spin ½ nuclei. At 1836, detecting the regional information associated with the magnetic resonance event includes acquiring one or more magnetic resonance signals indicative of nuclear spins associated with the target tissue-contained spin ½ nuclei, via a plurality of RF coils. At 1838, detecting the regional information associated with the magnetic resonance event includes acquiring one or more magnetic resonance signals indicative of an in vivo $T_1$ relaxation parameter associated with the target tissue-contained spin ½ nuclei. At 1840, detecting the regional information associated with the magnetic resonance event includes acquiring one or more magnetic resonance signals indicative of an in vivo $T_2$ relaxation parameter associated with the target tissue-contained spin ½ nuclei.

At 1842, the method 1700 can include generating a response based on the detected regional information.

At 1844, the method 1700 can include monitoring a magnetic resonance event generated by net nuclear spin isotopes present in a biological sample received in a void 106 of a ferromagnetic microstructure configured to generate a static magnetic field within the void 106. At 1846, monitoring the magnetic resonance event includes applying one or more RF pulses of a character and for a sufficient time to excite one or more of the net nuclear spin isotopes present in the biological sample and acquiring one or more magnetic resonance signals associated with the magnetic resonance event generated by net nuclear spin isotopes. At 1848, monitoring the magnetic resonance event includes acquiring magnetic relaxation information associated with regional changes in the magnetic resonance event generated by the net nuclear spin isotopes.

At 1850, the method 1700 can include providing a response based on the monitored magnetic resonance event. At 1852, providing a response includes providing at least one of an output, a response signal, a display, a data array, or a spectral plot. At 1854, providing a response include providing one or more images associated with at least one of a spatial distribution of $T_1$ relaxation time information or a spatial distribution of $T_2$ relaxation time information.

At 1856, the method 1700 can include detecting a spatial distribution of a magnetic resonance event associated with a biological sample exposed to a surface-defined void 106 of a ferromagnetic microstructure, the ferromagnetic microstructure configured to generate a static magnetic field within the surface-defined void 106 and configured to affect a magnetic resonance relaxation process associated with the biological sample at least while the biological sample is received in the surface-defined void 106.

At 1858, the method 1700 includes generating a response based on the detected spatial distribution of the magnetic resonance event.

At 1860, the method 1700 includes automatically communicating the response to a user.

At 1862, the method 1700 can include affecting at least one of a proton transverse magnetic relaxation time or a proton longitudinal magnetic relaxation time associated with a biological sample by providing a plurality of ferromagnetic microstructures to at least a portion of the biological sample, one or more of the plurality of ferromagnetic microstructures including a first internal surface 104 defining a void 106, the void 106 being selectively accessible to the biological sample, the plurality of ferromagnetic microstructures including a sufficient amount of at least one ferromagnetic material to generate a time-invariant magnetic field 108 within the void 106, the time-invariant magnetic field 108 of a sufficient character to affect at least one of a proton transverse magnetic relaxation time or a proton longitudinal magnetic relaxation time associated with the biological sample.

At 1864, the method 1700 can include detecting at least one parameter associated with the affected at least one of a proton transverse magnetic relaxation time or a proton longitudinal magnetic relaxation time associated with the biological sample.

At 1866, the method 1700 can include generating a response based on the detected at least one parameter.

At 1868, the method 1700 can include detecting a spatial distribution of a magnetic resonance event associated with a targeted biological sample exposed to a surface-defined void of one or more selectively-targeted ferromagnetic microstructures, the one or more selectively-targeted ferromagnetic microstructures configured to generate a static magnetic field within the surface-defined void and configured to affect a magnetic resonance relaxation process associated with the biological sample at least while the biological sample is received in the surface-defined void. At 1870, detecting the spatial distribution of the magnetic resonance event includes detecting the spatial distribution of the magnetic resonance event associated with one or more ferromagnetic microstructures selectively-targeted to at least one cell surface receptor targeting moiety. At 1872, detecting the spatial distribution of the magnetic resonance event includes detecting the spatial distribution of the magnetic resonance event associated with one or more ferromagnetic microstructures selectively-targeted to include at least one transmembrane receptor targeting moiety. At 1874, detecting the spatial distribution of the magnetic resonance event includes detecting the spatial distribution of the magnetic resonance event associated with one or more ferromagnetic microstructures selectively-targeted to at least one antigen-targeting moiety. At 1876, detecting the spatial distribution of the magnetic resonance event includes detecting the spatial distribution of the magnetic resonance event associated with one or more ferromagnetic microstructures selectively-targeted to at least one immune-receptor targeting moiety. At 1878, detecting the spatial distribution of the magnetic resonance event includes detecting the spatial distribution of the magnetic resonance event associated with one or more ferromagnetic microstructures selectively-targeted to at least one folate receptor targeting moiety. At 1880, detecting the spatial distribution of the magnetic resonance event includes detecting the spatial distribution of the magnetic resonance event associated with one or more ferromagnetic microstructures selectively-targeted to at least one nucleotide binding moiety. At 1882, detecting the spatial distribution of the magnetic resonance event includes detecting the spatial distribution of the magnetic resonance event associated with one or more ferromagnetic microstructures selectively-targeted to at least one oligonucleotide binding moiety. At 1884, detecting the spatial distribution of the magnetic resonance event includes detecting the spatial distribution of the magnetic resonance event associated with one or more ferromagnetic microstructures selectively-targeted to at least one oligodeoxyribonucleotide binding moiety. At 1886, detecting the spatial distribution of the magnetic resonance event includes detecting the spatial distribution of the magnetic resonance event associated with one or more ferromagnetic microstructures selectively-targeted to at least one oligoribonucleotide binding moiety. At 1888, detecting the spatial distribution of the magnetic resonance event includes detecting the spatial distribution of the magnetic resonance event associated with one or more ferromagnetic microstructures selectively-targeted to at least one amyloid binding moiety. At 1890, detecting the spatial distribution of the magnetic resonance event includes detecting the spatial distribution of the magnetic resonance event associated with one or more ferromagnetic microstructures selectively-targeted to at least one β-amyloid binding moiety. At 1892, detecting the spatial distribution of the magnetic resonance event associated includes detecting the spatial distribution of the magnetic resonance event associated with one or more ferromagnetic microstructures selectively-targeted to one or more genomic targets. At 1894, detecting the spatial distribution of the magnetic resonance event includes detecting the spatial distribution of the magnetic resonance event associated with one or more ferromagnetic microstructures selectively-targeted to at least one oncogene. At 1896, detecting the spatial distribution of the magnetic resonance event includes detecting the spatial distribution of the magnetic resonance event associated with one or more ferromagnetic microstructures selectively-targeted to at least one chromosome translocation. At 1898, detecting the spatial distribution of the magnetic resonance event includes detecting the spatial distribution of the magnetic resonance event associated with one or more ferromagnetic microstructures selectively-targeted to at least one methylated deoxyribonucleic acid sequence. At 1900, detecting the spatial distribution of the magnetic resonance event includes detecting the spatial distribution of the magnetic resonance event associated with one or more ferromagnetic microstructures selectively-targeted to at least one methylated deoxyribonucleic acid sequence including a methylated cytosine. At 1902, detecting the spatial distribution of the magnetic resonance event includes detecting the spatial distribution of the magnetic resonance event associated with one or more ferromagnetic microstructures selectively-targeted to at least one methylated ribonucleic acid sequence. At 1904, detecting the spatial distribution of the magnetic resonance event includes detecting the spatial distribution of the magnetic resonance event associated with one or more ferromagnetic microstructures selectively-targeted to at least one deoxyribonucleic acid sequence including unmethylated cytosine. At 1906, detecting the spatial distribution of the magnetic resonance event includes detecting the spatial distribution of the magnetic resonance event associated with one or more ferromagnetic microstructures selectively-targeted to at least one single-nucleotide polymorphism. At 1908, detecting the spatial distribution of the magnetic resonance event includes detecting the spatial distribution of the magnetic resonance event associated with one or more ferromagnetic microstructures selectively-targeted to at least one of a somatic mutation, germline mutation, chemically induced mutation, biologically induced mutation, or an environmentally induced mutation. At 1910, detecting the spatial distribution of the magnetic resonance event includes detecting the spatial distribution of the magnetic resonance event associated with one or more ferromagnetic microstructures selectively-targeted to at least one double stranded deoxyribonucleic acid sequence. At 1912, detecting the spatial distribution of the magnetic resonance event includes detecting the spatial distribution of the magnetic resonance event associated with one or more ferromagnetic microstructures selectively-targeted to at least one single stranded deoxyribonucleic acid sequence. At 1914, detecting the spatial distribution of the magnetic resonance event includes detecting the spatial distribution of the magnetic resonance event associated with one or more ferromagnetic microstructures selectively-targeted to at least one mitochondrial deoxyribonucleic acid sequence. At 1916, detecting the spatial distribution of the magnetic resonance event includes detecting the spatial distribution of the magnetic resonance event associated with one or more ferromagnetic microstructures selectively-targeted to at least one of a point mutation, an insertion of one or more nucleotides, or a deletion of one or more nucleotides. At 1918, detecting the spatial distribution of the magnetic resonance event includes detecting the spatial distribution of the magnetic resonance event associated with one or more ferromagnetic microstructures selectively-targeted to at least a portion of a human chromosome in vivo. At 1920, detecting the spatial distribution of the magnetic resonance event includes detecting the spatial distribution of the magnetic resonance event associated with one or more ferromagnetic microstructures selectively-targeted to a zinc finger-including protein. At 1922, detecting the spatial distribution of the magnetic resonance event includes detecting the spatial distribution of the magnetic resonance event associated with one or more ferromagnetic microstructures selectively-targeted to a deoxyribonucleic acid sequence. At 1924, detecting the spatial distribution of the magnetic resonance event includes detecting the spatial distribution of the magnetic resonance event associated with one or more ferromagnetic microstructures selectively-targeted to a ribonucleic acid sequence target. At 1926, detecting the spatial distribution of the magnetic resonance event includes detecting the spatial distribution of the magnetic resonance event associated with one or more ferromagnetic microstructures selectively-targeted to an antigen epitope. At 1928, detecting the spatial distribution of the magnetic resonance event includes detecting the spatial distribution of the magnetic resonance event associated with one or more ferromagnetic microstructures selectively-targeted to an antigen mimotope. At 1930, detecting the spatial distribution of the magnetic resonance event includes detecting a spatial distribution of a magnetic resonance event associated with the targeted biological sample exposed to a selectively-accessible surface-defined void of one or more selectively-targeted, selectively-accessible, ferromagnetic microstructures. At 1932, the method 1700 includes generating a response based on the detected spatial distribution of the magnetic resonance event.

At 1934, the method 1700 includes affecting at least one of a non-zero spin nuclei transverse magnetic relaxation time or a non-zero spin nuclei longitudinal magnetic relaxation time associated with a biological sample by providing a plurality of target-specific ferromagnetic microstructures to at least a portion of the biological sample, at least some of the target-specific ferromagnetic microstructures including a first internal surface defining a void, the void being selectively accessible to the biological sample, the target-specific ferromagnetic microstructures including a sufficient amount of at least one ferromagnetic material to generate a time-invariant magnetic field within the void, the time-invariant magnetic field of a sufficient character to affect at least one of a non-zero spin nuclei transverse magnetic relaxation time or a non-zero spin nuclei longitudinal magnetic relaxation time associated with the biological sample. At 1936, affecting the at least one of a non-zero spin nuclei transverse magnetic relaxation time or the non-zero spin nuclei longitudinal magnetic relaxation time includes affecting at least one of a proton transverse magnetic relaxation time or a proton longitudinal magnetic relaxation time associated with a biological sample by providing a plurality of target-specific ferromagnetic microstructures to at least a portion of the biological sample.

At 1938, affecting the at least one of a non-zero spin nuclei transverse magnetic relaxation time or a non-zero spin nuclei longitudinal magnetic relaxation time associated with a biological sample includes providing a sufficient amount of a plurality of target-specific ferromagnetic microstructures including one or more targeting moieties attached thereof to at least a portion of the biological sample to affecting the at least one of a non-zero spin nuclei transverse magnetic relaxation time or a non-zero spin nuclei longitudinal magnetic relaxation time associated with a biological sample. At 1940, the method 1700 includes detecting at least one parameter associated with the affected at least one of a non-zero spin nuclei transverse magnetic relaxation time or a non-zero spin nuclei longitudinal magnetic relaxation time associated with the biological sample. At 1942, the method 1700 includes generating a response based on the detected at least one parameter.

Example 1

Ferromagnetic Microstructures that Target Human Chromosomes In Vivo

Ferromagnetic microstructures 102 are constructed with a void 106 accessible to biological samples and a static magnetic field within the void 106 are targeted to chromosomes in the nucleus of animal cells. Ferromagnetic microstructures 102 that are constructed of iron oxide are modified by coating with dextran or siloxane and targeting molecules, which promote cellular internalization of the ferromagnetic microstructures 102, transport to the nucleus, and binding to histones comprising the chromosomes (see, e.g., U.S. Patent Application No. 2008/0206146 (published Aug. 28, 2008, the contents of which is incorporated herein by reference). Ferromagnetic microstructures 102 configured to target chromosomes are administered to humans or animals and then are detected in situ by circuitry systems that detect and report magnetic resonance relaxation processes. Chromosome-targeted ferromagnetic microstructures 102 and associated circuitry systems constitute a nuclear magnetic resonance imaging system that can image chromosomes, nuclei, cells, and tissues in vivo.

Nanoparticles are constructed of iron oxide by adding a solution of $FeCl_3$ and $FeCl_2$ in hydrochloric acid dropwise to a solution of sodium hydroxide under nitrogen gas at 80° C. The reaction is cooled to room temperature and the particles are recovered with an external magnet. For example, iron oxide nanoparticles with a diameter of 10±3 nm are produced. See, e.g., Zhang et al, Cancer Research, vol. 67, pp. 1555-1562, (2007) (the contents of which are incorporated herein by reference). Hollow ferromagnetic microstructures 102 with a void 106 are fabricated using colloids as template and electrostatic layer by layer self assembly of inorganic nanoparticles (e.g., $Fe_3O_4$) and polymer multilayers, followed by removal of the templated core. For example, polystryrene (PS) latex particles 640 nm in diameter are used as templates and $SiO_2$ particles (or $Fe_3O_4$ particles) approximately 25 nm in diameter are used as coating nanoparticles. The nanoparticles electrostatically self-assemble onto the linear cationic polymer, poly (diallyldimethylammoniumchloride) (PDADMAC, Sigma-Aldrich, St. Louis, Mo.). Repeated cycles layering PDADMAC and $SiO_2$ results in PS latex cores with multiple layers of PDADMAC and $SiO_2$ adsorbed. The organic matter is decomposed by heating to 500° C. and a hollow sphere composed of $SiO_2$ remains. See, e.g., Caruso et al, Science, vol. 282, pp. 1111-1114 (1998) (the contents of which are incorporated herein by reference). Scanning electron microscopy (SEM) and transmission electron microscopy (TEM) are used to characterize the spheres.

In an embodiment, hollow ferromagnetic microstructures 102 are synthesized in one step by using calcium carbonate $CaCO_3$ as a removable core. $CaCO_3$ nanoparticles (25-60 nm) are combined with $Fe_3O_4$ nanoparticles (5 nm) and tetraethoxysilane under alkaline conditions. The ferromagnetic microstructures 102 are immersed in weak acetic acid to remove the $CaCO_3$. See, e.g., Wu et al, J. Appl. Physics, vol. 99, pp. 08H104-08H104-3 (2006) (the contents of which are incorporated herein by reference). To coat the ferromagnetic microstructures 102, they are combined with 3-aminopropyltrimethoxy-siloxane (APTMS) after being transferred to an organic solvent (e.g., toluene) and then refluxed under nitrogen gas for 10 hours. Modified ferromagnetic microstructures 102 with reactive amino groups are transferred to water and characterized (See, e.g., Zhang et al, Ibid.). The APTMS-coated ferromagnetic microstructures 102 are characterized with transmission electron microscopy and an image analysis program (for example JEOL-100CX transmission electron microscope, JEOL USA, Inc., Peabody, Mass.). Surface charges of the ferromagnetic microstructures 102 are determined by measuring the zeta potentials as a function of pH values using a particle charge detector (e.g., PCD 03, Muetec, Herrsching, Germany). Validation of the APTMS coating is determined by energy dispersive X-ray analysis and organic elementary analysis (See, e.g., Zhang et al, Ibid.). A vibrating sample magnetometer (Digital Measurement System, Inc., model 155) is employed to measure the magnetization of the ferromagnetic microstructures 102 at room temperature. See, e.g., Selim et al, Biomaterials, vol. 28, pp. 710-716 (2007) (the contents of which are incorporated herein by reference). Alternatively, the mass magnetization value is determined with a super conducting quantum interference device (SQUID) magnetometer to establish the electromagnetic units (emu) per gram of magnetic atom. See, e.g., Lee et al, Nature Medicine, vol. 13, pp. 95-99 (2007) (the contents of which are incorporated herein by reference). Ferromagnetic microstructures 102 with different magnetic fields are constructed by varying the metal composition and the size of the iron oxide particles. For example, 12 nm diameter $MFe_2O_4$ (M=Mn, Fe, Co and Ni) nanoparticles display different mass magnetization values as measured by a SQUID. Also, the magnetic moments of the $MFe_2O_4$ nanoparticles vary with their metal composition. See Table 1. The mass magnetization of $MFe_2O_4$ nanoparticles is varied by altering the size of the nanoparticles. For example, $MnFe_2O_4$ nanoparticles of 6, 9 and 12 nm diameter display magnetization values of 68, 98 and 110 emu/gm respectively (see, e.g., Lee et al, Ibid.)

TABLE 1

Metal oxide nanoparticles variation in magnetization and magnetic moment with metal composition (Adapted from Lee et al, Ibid.).

| | Metal Oxide | | | |
|---|---|---|---|---|
| | $Mn Fe_2O_4$ | $Fe Fe_2O_4$ | $Co Fe_2O_4$ | $Ni Fe_2O_4$ |
| Mass magnetization (emu/g) | 110 | 101 | 99 | 85 |
| Magnetic moment | $5 \mu_B$ | $4 \mu_B$ | $3 \mu_B$ | $2 \mu_B$ |

In an embodiment, ferromagnetic microstructures 102 with a void 106 and an opening to allow access of biomolecules (e.g., $H_2O$) to the void 106 and its associated magnetic field are constructed using microfabrication methods. For example, magnetic microstructures with two disks of metal (e.g., iron) held at a fixed distance by an internal nonmagnetic metal post or by external biocompatible photo-epoxy posts are fabricated. Microstructures are micromachined through a combination of metal evaporation and electroplating depositions followed by lithographically defined ion-milling and selective wet etching. See, e.g., Zabow et al, Nature, vol. 453, pp. 1058-1062 (2008) (the contents of which are incorporated herein by reference). Microfabrication of double disk microstructures is scalable and suited to parallel wafer-level techniques. Microstructures with diameters between about one mm to about 1 μm are constructed, and smaller sub-micrometer structures are constructed using techniques such as deep-ultraviolet or electron beam lithography. Alternatively, one or more of the microstructures are chemically synthesized. See, e.g., Osaka et al., *Chemical Synthesis of Magnetic nanoparticles and their Applications to Recording Media & Biomedical Materials*, 214th ECS Meeting, Abstract No. 2592 (2008) (the contents of which are incorporated herein by reference).

Targeting molecules are conjugated to the coated ferromagnetic microstructures 102 (e.g., APTMS-coated) to promote cellular internalization and to specifically target histone proteins in chromosomes. For example reactive amines present on APTMS-coated ferromagnetic microstructures 102 are derivatized with N-succinimidyl-3-(2-pyridyldithio) propionate (SPDP) (Molecular Biosciences, Boulder, Colo.), and a peptide derived from HIV-1 tat protein (amino acids 48-57) is added to the derivatized ferromagnetic microstructures 102 and allowed to react leading to covalent attachment of tat peptide (48-57) to the ferromagnetic microstructures 102. See, e.g., Josephson et al, Bioconjugate Chem., vol. 10, pp. 186-191 (1999) (the contents of which are incorporated herein by reference). Ferromagnetic microstructures 102 conjugated with TAT peptide are efficiently internalized into the cellular cytoplasm and nuclei of mammalian cells. In vitro ferromagnetic microstructures 102/TAT peptide conjugates are taken up 100-fold more efficiently than unmodified ferromagnetic microstructures 102 and lymphocytes can take up $1.27 \times 10^7$ particles per cell (Josephson et al, Ibid.)

To target ferromagnetic microstructures 102 to chromosomes, a second targeting molecule is attached. Ferromagnetic microstructures 102 derivatized with SPDP are reacted with anti-histone antibodies, for example, anti-histone H3 antibody (Abeam ab1791; Cambridge, Mass.). Derivatized ferromagnetic microstructures 102 are incubated with an equimolar mixture of TAT peptide and anti-histone H3 antibody to attach both targeting molecules and to promote both cellular internalization and chromatin binding. Alternatively, anti-histone antibodies can target modified histones, such as methylated histones or acetylated histones. For example, antibodies specific for histone H3 methylated at lysine 79 (H3K79Me) (Abeam ab3594, Cambridge, Mass.) are used to target ferromagnetic microstructures 102 to chromatin sites that are marked by modified histones.

Alternatively, a fusion protein comprising TAT peptide and an anti-histone antibody is engineered using recombinant DNA techniques and expressed in mammalian or microbial expression systems (see, e.g., Sambrook et al, Molecular Cloning: A Laboratory Manual, 3$^{rd}$ Edition, Cold Spring Harbor Laboratory Press, 2001). The TAT peptide-anti-histone antibody fusion protein is attached to ferromagnetic microstructures 102 derivatized with SPDP as described above (see, also Josephson et al, Ibid.)

Ferromagnetic microstructures 102 with conjugated targeting molecules are used to image tumor cells in vivo. For example, $Fe_3O_4$ ferromagnetic microstructures 102 with an anti-HER2 (human epidermal growth factor receptor-2) antibody (e.g., Herceptin, Genentech, South San Francisco, Calif.) conjugated to their surface are injected intravenously into nude mice bearing tumors expressing HER2 (e.g., NIH3T6.7) the ferromagnetic microstructures 102 are detected via radio frequency (RF) coils (e.g., surface coils, bird cage coils, or volume coils; available from Bruker Bio-Spin Corp., Billerica, Mass.).

For example, magnetic nanoparticles with targeting molecules attached, (e.g., Herceptin) are injected intravenously in tumor bearing animals and detected 2 hours later using a 1.5-T clinical MRI instrument with a micro-47 surface coil (Intera; Philips Medical Systems). Using optimized ferromagnetic microstructures 102 with an accessible void 106 it may be possible to detect small tumors in vivo that weigh approximately 50 mg (Lee et al, Ibid.).

To image a region within a biological subject, in vivo, and in the absence of external magnetic fields, ferromagnetic microstructures 102 with voids 106 and known magnetic fields (e.g., magnetic moments) are pulsed with radiowaves at the Larmor frequency for the non-zero spin nuclei of interest in a magnetic field as determined by the equation: $\omega_L = \gamma H$ where $\omega_L$ is the Larmor frequency and $\gamma$ is the gyromagnetic ratio for the non-zero spin nuclei of interest and H is the magnetic field strength. Absorption of radiowaves at $\omega_L$ by the non-zero spin nuclei in the void 106 leads to higher energy state transitions and subsequent emission of radiowaves following stoppage of the radiowave pulse. The relaxation or radiowave emission is characterized by a time constant, $T_2$ that depends on the molecular environment of the non-zero spin nuclei in the magnetic field of the void 106. Radiowaves emitted at the Larmor frequency induce currents in receiver RF coils and the induced currents are amplified by RF preamplifiers and then transmitted to a receiver unit responsible for digitizing and storing the data prior to transfer to a host computer. See, e.g., Silva et al, Concepts in Magnetic. Resonance Part A, vol. 16A, pp. 35-49 (2003) (the contents of which are incorporated herein by reference). Hardware and instrumentation for magnetic resonance imaging are available at Bruker BioSpin, Corp., Billerica, Mass. Moreover, by tuning the ferromagnetic microstructures 102 magnetic field strength and the corresponding receiver RF coil resonance frequency it is possible to specifically detect different ferromagnetic microstructures 102 in multiplex. For example, ferromagnetic microstructures 102 with different magnetic moments of $5\mu_B$ and $2\mu_B$ are detected via RF coils that differ in their resonance frequency by a factor of 2.5. Thus, control ferromagnetic microstructures 102, without targeting molecules attached can be detected simultaneously with targeted ferromagnetic microstructures 102 by using distinct ferromagnetic microstructures 102 and RF coils with different magnetic field strengths and resonance frequencies respectively.

Example 2

Ferromagnetic Microstructures for Magnetic Resonance Imaging of Beta-Amyloid Plaque Ferromagnetic microstructures 102 can be targeted to aggregated beta amyloid associated with Alzheimer's disease and they can be used for noninvasive detection of beta amyloid plaques. Conjugation of peptides, antibodies or small molecules to the surface of derivatized ferromagnetic microstructures 102 can mediate specific binding and localization of the ferromagnetic microstructures 102 to aggregated beta amyloid and beta amyloid plaques. In addition, coating or conjugation of apolipoproteins, peptides, small molecules, and surfactants to the ferromagnetic microstructures 102 surface can promote their transit of the blood brain barrier (BBB). See, e.g., Fenart et al., *Evaluation of Effect of Charge and Lipid Coating on Ability of 60-nm Nanoparticles to Cross an In Vitro Model of the Blood-Brain Barrier,* 291(3): 1017-1022, (1999) (the contents of which are incorporated herein by reference).

Ferromagnetic microstructures 102 modified to promote transit of the BBB are administered intravenously or intra-arterially to detect beta amyloid plaque in the brain. Modified ferromagnetic microstructures 102 with a void 106 and localized to beta amyloid plaque are detected by magnetic resonance imaging without the need for a strong external magnetic field. Thus, ferromagnetic microstructures 102 targeted to beta amyloid plaque can represent a relatively low cost, noninvasive method to detect beta amyloid plaque and to help diagnose Alzheimer's disease.

Ferromagnetic microstructures 102 containing an accessible void 106 are modified by coating or conjugation of proteins and surfactants to promote transit across the BBB. For example, coupling apolipoprotein E to the surface of nanoparticles via an avidin/biotin linkage can promote transit across the BBB. See, e.g., Michaelis et al, Journal Pharmacology and Experimental Therapeutics, vol. 317, pp. 1246-1253 (2006) (the contents of which are incorporated herein by reference). Iron oxide ferromagnetic microstructures 102 are coated with APTMS, a siloxane with functional amino groups, using methods detailed in Zhang et al, Ibid. APTMS-coated ferromagnetic microstructures 102 can then be reacted with a polyethylene glycol crosslinker, NHS-PEG3400-Mal (Nektar, Huntsville, Ala.) to derive sulfhydryl-reactive ferromagnetic microstructures 102. Avidin (NeutrAvidin, Pierce, Rockford, Ill.) is derivatized with 2-iminothiolane/HCL (Pierce, Rockford, Ill.) to create avidin with sulfhydryl groups which are combined with the sulfhydryl-reactive ferromagnetic microstructures 102 to yield ferromagnetic microstructures 102 with avidin on their surface. Apolipoprotein E (recombinant human apolipoprotein E3; Leinco Technologies, Inc., St. Louis, Mo.) is biotinylated using standard protocols accompanying biotinylation reagents (PFP-Biotin, Pierce, Rockford, Ill.) and then added to avidin-coupled ferromagnetic microstructures 102 to create ferromagnetic microstructures 102 with apolipoprotein E on their surface (Michaelis et al, Ibid.). Alternatively, ferromagnetic microstructures 102 are coated with surfactants to promote transit across the BBB. For example, coating ferromagnetic microstructures 102 with polysorbate 80 (Mallinckrodt Baker, Inc., Phillipsburg, N.J. 08865) using described methods (see, e.g., Michaelis et al, Ibid.) may promote their transport across the BBB.

To target ferromagnetic microstructures 102 for beta amyloid plaques, peptides, antibodies or small molecules with affinity for beta amyloid aggregates are attached to the surface of the ferromagnetic microstructures 102. For example, a peptide, Aβ1-40, derived from amyloid precursor protein (APP) binds with high affinity to beta amyloid plaques and can be used to target ferromagnetic microstructures 102 to beta amyloid plaque. See, e.g., Wadghiri et al, Magnetic Resonance Medicine, vol. 50, pp. 293-302 (2003) (the contents of which are incorporated herein by reference). Ferromagnetic microstructures 102 are coated with dextran and then Aβ1-40 peptide is adsorbed onto the ferromagnetic microstructures 102 using standard methods (see, e.g., Wadghiri et al Ibid.). To deliver Aβ1-40-ferromagnetic microstructures 102 to brain tissues in animals (e.g., transgenic mice overexpressing APP) they are co-injected into the carotid artery with mannitol (to promote transit across the BBB) as described (see, e.g., Wadghiri et al, Ibid.). Alternatively, ferromagnetic microstructures 102 with avidin covalently coupled on their surface may be mixed with an equimolar mixture of biotinylated Aβ1-40 and biotinylated apolipoprotein E (see, e.g., Michaelis et al, Ibid.) to produce ferromagnetic microstructures 102 suitable for injection in the carotid artery that may cross the BBB and distribute in the brain.

One can detect ferromagnetic microstructures 102 localized to beta amyloid plaques in animal brains ex vivo by magnetic resonance imaging, histochemistry and immunohistochemistry. For example ex vivo magnetic resonance imaging of fixed whole mouse brains following intra-arterial injection of magnetic Aβ1-40-nanoparticles is done using a SMIS console interfaced to a 7 Tesla horizontal bore magnet equipped with 250 mT/m actively shielded gradients (Magnex Scientific, Abdingdon, UK). Magnetic resonance imaging methods using $T_2$-weighted spin echo pulsing can accurately detect beta amyloid plaque numerical density in correlation with immunohistochemistry techniques (see, e.g., Wadghiri et al, Ibid.).

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity, control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

The invention claimed is:

1. A composition, comprising:
   a plurality of ferromagnetic microstructures having an average size ranging from 10 nanometers to about 1 millimeter,
   one or more of the plurality of ferromagnetic microstructures having an external surface and an internal surface, the internal surface defining a void, the void configured to receive a biological sample within a patient,
      the one or more of the plurality of ferromagnetic microstructures configured to generate a time-invariant magnetic field within at least a portion of the void to affect a nuclear magnetic resonance relaxation process associated with the biological sample at least while the biological sample is received within the void,
      at least one of the external surface or the internal surface modified with one or more functional chemical groups.

2. The composition of claim 1, further comprising:
   one or more targeting moieties attached to at least one of the one or more of the plurality of ferromagnetic microstructures.

3. The composition of claim 1, wherein the one or more functional groups include at least one of a bio-compatible functional group, a charge functional group, a chemically reactive functional group, a hydrophilic functional group, a hydrophobic functional group, or an organofunctional group.

4. An imaging system, comprising:
   a plurality of ferromagnetic microstructures, one or more of the plurality of ferromagnetic microstructures having an external surface and an internal surface, the internal surface defining a void, the void configured to receive to a biological sample within the patient, the one or more of the plurality of ferromagnetic microstructures configured to generate a time-invariant magnetic field within at least a portion of the void to affect a nuclear magnetic resonance event associated with the biological sample received within the void, at least one of the external surface or the internal surface modified with one or more functional chemical groups; and circuitry for acquiring information associated with the magnetic resonance event.

5. The imaging system of claim 4, wherein the one or more functional groups include at least one bio-compatible functional group.

6. The imaging system of claim 4, wherein the one or more functional groups include at least one charge functional group.

7. The imaging system of claim 4, wherein the one or more functional groups include at least one chemically reactive functional group.

8. The imaging system of claim 4, wherein the one or more functional groups include at least one hydrophilic functional group.

9. The imaging system of claim 4, wherein the one or more functional groups include at least one hydrophobic functional group.

10. The imaging system of claim 4, wherein the one or more functional groups include at least one organofunctional group.

11. The imaging system of claim 4, wherein the external surface and the internal surface include one or more functional groups.

12. The imaging system of claim 4, wherein the external surface and the internal surface include one or more functional groups, at least one of the one or more targeting moieties groups on the internal surface different from at least one of the one or more targeting moieties groups on the outer surface.

13. The imaging system of claim 4, wherein the external surface includes a bio-compatible functional group, a charge functional group, a chemically reactive functional group, a hydrophilic functional group, a hydrophobic functional group, or an organofunctional group, and the internal surface includes a different one of a bio-compatible functional group, a charge functional group, a chemically reactive functional group, a hydrophilic functional group, a hydrophobic functional group, or an organofunctional group.

14. The imaging system of claim 4, wherein at least one of the external surface or the internal surface includes a functional group configured to immobilize one or more targeting moieties to the at least one of the external surface or the internal surface.

15. The imaging system of claim 4, wherein at least one of the external surface or the internal surface includes a siloxane-scaffold.

16. The imaging system of claim 4, wherein at least one of the external surface or the internal surface includes a siloxane-scaffold configured to immobilize one or more targeting moieties to the at least one of the external surface or the internal surface.

17. The imaging system of claim 4, further comprising:
a radio frequency transmitter configured to generate a radio frequency signal.

18. The imaging system of claim 4, further comprising:
one or more coils configured to generate one or more radio frequency pulses.

19. The imaging system of claim 4, further comprising:
a radio frequency receiver configured to acquire radio frequency information emitted by the biological sample.

20. The imaging system of claim 4, further comprising:
means for acquiring at least one spatial distribution parameter of a magnetic resonance event associated with one or more non-zero spin nuclei of a biological sample present within the void.

* * * * *

UNITED STATES PATENT AND TRADEMARK OFFICE
CERTIFICATE OF CORRECTION

| | | |
|---|---|---|
| PATENT NO. | : 8,058,872 B2 | Page 1 of 1 |
| APPLICATION NO. | : 12/455298 | |
| DATED | : November 15, 2011 | |
| INVENTOR(S) | : Roderick A. Hyde, Jordin T. Kare and Wayne R. Kindsvogel | |

It is certified that error appears in the above-identified patent and that said Letters Patent is hereby corrected as shown below:

Column 71, line 58: "average sizing range from 10 nanometers" should read --average size ranging from about 10 nanometers--

Column 72, line 21: "the void configured to receive to" should read --the void configured to receive--

Column 72, line 25: "the void to affect a nuclear magnetic" should read --the void to affect a magnetic--

Signed and Sealed this
Tenth Day of January, 2012

David J. Kappos
*Director of the United States Patent and Trademark Office*